(12) United States Patent
Nir et al.

(10) Patent No.: US 11,638,615 B2
(45) Date of Patent: May 2, 2023

(54) INTELLIGENT SURGICAL TOOL CONTROL SYSTEM FOR LAPAROSCOPIC SURGERIES

(71) Applicant: Asensus Surgical Europe S.à.R.L., Lugano (CH)

(72) Inventors: Tal Nir, Haifa (IL); Gal Atarot, Kfar Saba (IL); Motti Frimer, Zichron Yaakov (IL)

(73) Assignee: Asensus Surgical US, Inc., Durham, NC (US)

( * ) Notice: Subject to any disclaimer, the term of this patent is extended or adjusted under 35 U.S.C. 154(b) by 361 days.

(21) Appl. No.: 15/756,118

(22) PCT Filed: Aug. 30, 2016

(86) PCT No.: PCT/IL2016/050947
§ 371 (c)(1),
(2) Date: Feb. 28, 2018

(87) PCT Pub. No.: WO2017/037705
PCT Pub. Date: Mar. 9, 2017

(65) Prior Publication Data
US 2018/0271603 A1 Sep. 27, 2018

Related U.S. Application Data

(60) Provisional application No. 62/211,787, filed on Aug. 30, 2015.

(51) Int. Cl.
*A61B 34/00* (2016.01)
*A61B 34/20* (2016.01)
(Continued)

(52) U.S. Cl.
CPC ............ *A61B 34/25* (2016.02); *A61B 1/3132* (2013.01); *A61B 17/00234* (2013.01);
(Continued)

(58) Field of Classification Search
CPC combination set(s) only.
See application file for complete search history.

(56) References Cited

U.S. PATENT DOCUMENTS

| 6,425,858 B1 * | 7/2002 | Minami | ................. | A61B 1/045 |
| | | | | 348/240.99 |
| 7,794,396 B2 * | 9/2010 | Gattani | .................. | H04N 23/69 |
| | | | | 600/173 |

(Continued)

FOREIGN PATENT DOCUMENTS

| WO | WO-9625882 A1 * | 8/1996 | ............... A61B 8/12 |
| WO | WO-2013042107 A1 * | 3/2013 | ............. A61B 34/30 |

(Continued)

*Primary Examiner* — Anh Tuan T Nguyen
*Assistant Examiner* — Shankar Raj Ghimire

(57) ABSTRACT

An intelligent surgical tool control system, comprising a tool management system; an indicating means to indicate at least one surgical event; a communicable database for storing, for each item of interest, its identity, its present 3D position and at least one previous 3D position; and at least one processor to identify, from a surgical event, an output surgical procedure. The tool management system can comprise a maneuvering mechanism to maneuver a surgical tool in at least two dimensions; and a controller to control at least one of activation and deactivation of a surgical tool and articulation of a surgical tool. The indicating means can indicate a surgical event selected from movement of a moving element and presence of an item of interest, where movement is determinable if the current 3D position of the moving element is substantially different from a previous 3D position of the same.

20 Claims, 32 Drawing Sheets

(51) Int. Cl.
  *A61B 1/313* (2006.01)
  *A61B 17/00* (2006.01)
  *A61B 17/29* (2006.01)
  *A61B 5/00* (2006.01)
  *A61B 5/055* (2006.01)
  *A61B 5/06* (2006.01)
  *A61B 5/369* (2021.01)
  *A61B 5/389* (2021.01)
  *A61B 34/30* (2016.01)
  *A61B 90/00* (2016.01)

(52) U.S. Cl.
  CPC .............. *A61B 34/20* (2016.02); *A61B 34/75* (2016.02); *A61B 5/055* (2013.01); *A61B 5/061* (2013.01); *A61B 5/369* (2021.01); *A61B 5/389* (2021.01); *A61B 5/4244* (2013.01); *A61B 5/6824* (2013.01); *A61B 5/7275* (2013.01); *A61B 2017/00119* (2013.01); *A61B 2017/00207* (2013.01); *A61B 2017/00216* (2013.01); *A61B 2017/00221* (2013.01); *A61B 2017/2906* (2013.01); *A61B 2034/2048* (2016.02); *A61B 2034/2055* (2016.02); *A61B 2034/2072* (2016.02); *A61B 2034/252* (2016.02); *A61B 2034/256* (2016.02); *A61B 2034/302* (2016.02); *A61B 2090/374* (2016.02); *A61B 2503/20* (2013.01); *A61B 2505/05* (2013.01); *A61B 2562/0219* (2013.01)

(56) References Cited

U.S. PATENT DOCUMENTS

| | | | | |
|---|---|---|---|---|
| 9,204,939 B2* | 12/2015 | Frimer | ............... | A61B 90/361 |
| 10,152,789 B2* | 12/2018 | Carnes | ............... | G06T 7/0012 |
| 2006/0258938 A1* | 11/2006 | Hoffman | ............... | A61B 5/061 |
| | | | | 600/424 |
| 2007/0053068 A1* | 3/2007 | Yamamoto | ............ | H04N 23/69 |
| | | | | 348/E5.042 |
| 2009/0192524 A1* | 7/2009 | Itkowitz | ............... | B25J 9/1666 |
| | | | | 606/130 |
| 2010/0073150 A1* | 3/2010 | Olson | ............... | A61B 34/30 |
| | | | | 340/407.1 |
| 2010/0318099 A1* | 12/2010 | Itkowitz | ................ | A61B 34/30 |
| | | | | 606/130 |
| 2012/0071893 A1* | 3/2012 | Smith | .................. | A61B 90/11 |
| | | | | 606/130 |
| 2013/0096575 A1* | 4/2013 | Olson | .................. | A61B 34/25 |
| | | | | 606/130 |
| 2013/0211244 A1* | 8/2013 | Nathaniel | ............. | A61B 5/055 |
| | | | | 600/424 |
| 2013/0211590 A1* | 8/2013 | Diolaiti | ................ | A61B 90/361 |
| | | | | 700/257 |
| 2013/0229502 A1* | 9/2013 | Kutsuma | ............ | G02B 23/2438 |
| | | | | 348/65 |
| 2014/0081659 A1* | 3/2014 | Nawana | ................ | A61B 5/1118 |
| | | | | 705/3 |
| 2014/0161331 A1* | 6/2014 | Cohen | ................... | A61M 25/09 |
| | | | | 382/128 |
| 2014/0163359 A1* | 6/2014 | Sholev | .................... | A61B 1/04 |
| | | | | 600/424 |
| 2014/0194896 A1* | 7/2014 | Frimer | .................... | A61B 34/32 |
| | | | | 606/130 |
| 2016/0015473 A1* | 1/2016 | Frimer | ............... | A61B 1/00149 |
| | | | | 606/130 |
| 2016/0067007 A1* | 3/2016 | Piron | .................... | A61B 34/20 |
| | | | | 705/3 |
| 2016/0314716 A1* | 10/2016 | Grubbs | ................... | G16H 40/67 |
| 2016/0331474 A1* | 11/2016 | Lacal | ..................... | G16H 20/40 |
| 2017/0049517 A1* | 2/2017 | Felder | .................... | A61B 34/30 |
| 2017/0161893 A1* | 6/2017 | Carnes | ................... | A61B 90/37 |
| 2017/0172382 A1* | 6/2017 | Nir | ...................... | A61B 1/00045 |
| 2017/0196437 A1* | 7/2017 | Dejima | ............... | A61B 17/3415 |
| 2017/0202624 A1* | 7/2017 | Atarot | ............... | A61B 17/00234 |
| 2017/0367771 A1* | 12/2017 | Tako | ..................... | G06T 19/003 |
| 2018/0129187 A1* | 5/2018 | Spieker | ............... | G05B 19/4061 |
| 2018/0250078 A1* | 9/2018 | Shochat | ................ | A61B 5/6848 |
| 2018/0310997 A1* | 11/2018 | Peine | ..................... | A61B 17/00 |
| 2018/0325604 A1* | 11/2018 | Atarot | ................... | A61B 5/1114 |
| 2019/0239725 A1* | 8/2019 | Ogasawara | ........ | A61B 1/00163 |
| 2019/0290297 A1* | 9/2019 | Haider | .................... | A61B 34/20 |
| 2020/0205922 A1* | 7/2020 | Cone | ..................... | A61B 34/25 |
| 2020/0273575 A1* | 8/2020 | Wolf | ..................... | G16H 40/20 |
| 2020/0289220 A1* | 9/2020 | Denlinger | ............. | A61B 34/77 |

FOREIGN PATENT DOCUMENTS

| | | | | |
|---|---|---|---|---|
| WO | WO-2013128457 A1 * | 9/2013 | ............. | A61B 34/30 |
| WO | WO-2014049598 A1 * | 4/2014 | ............. | A61B 5/066 |

* cited by examiner

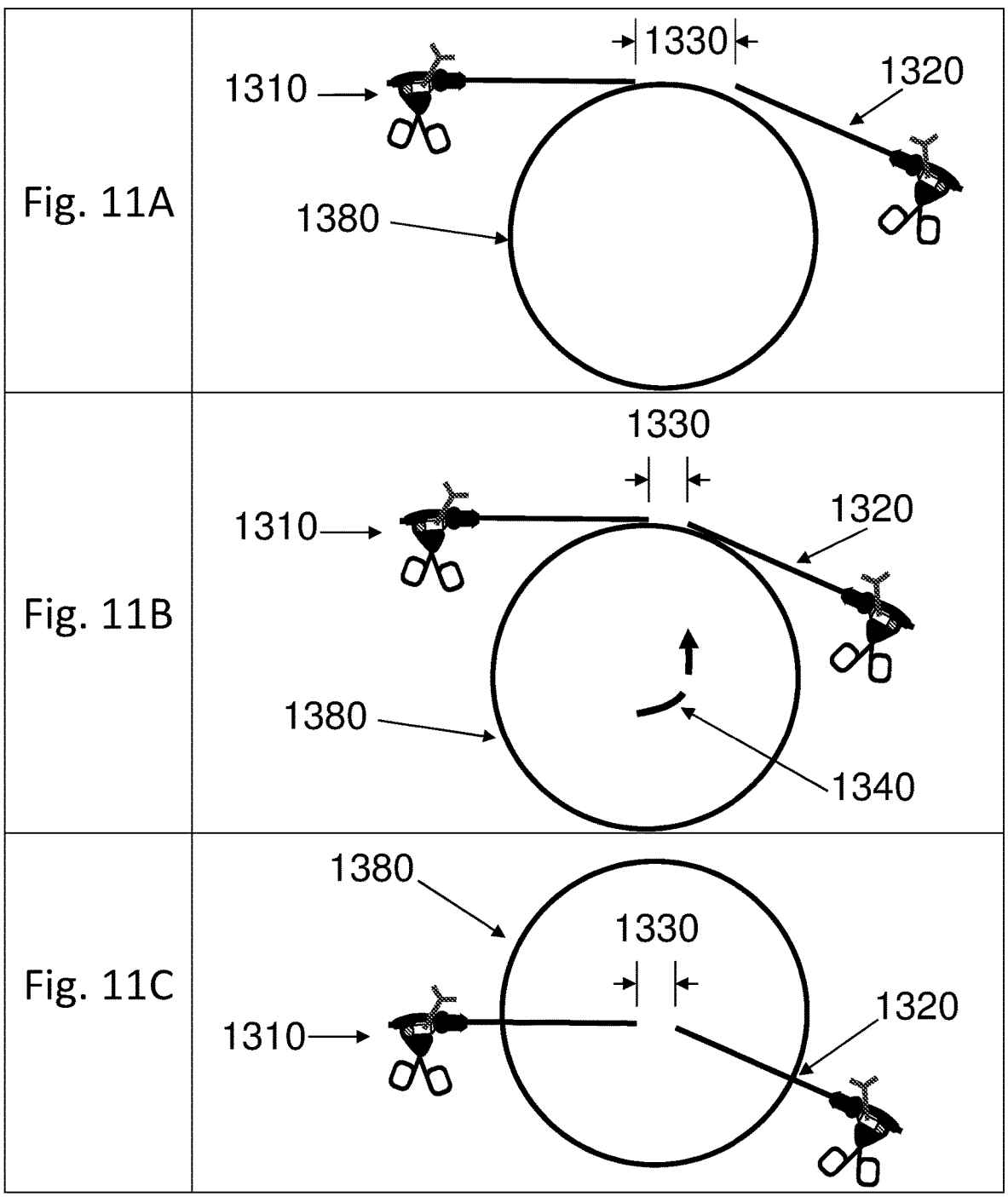

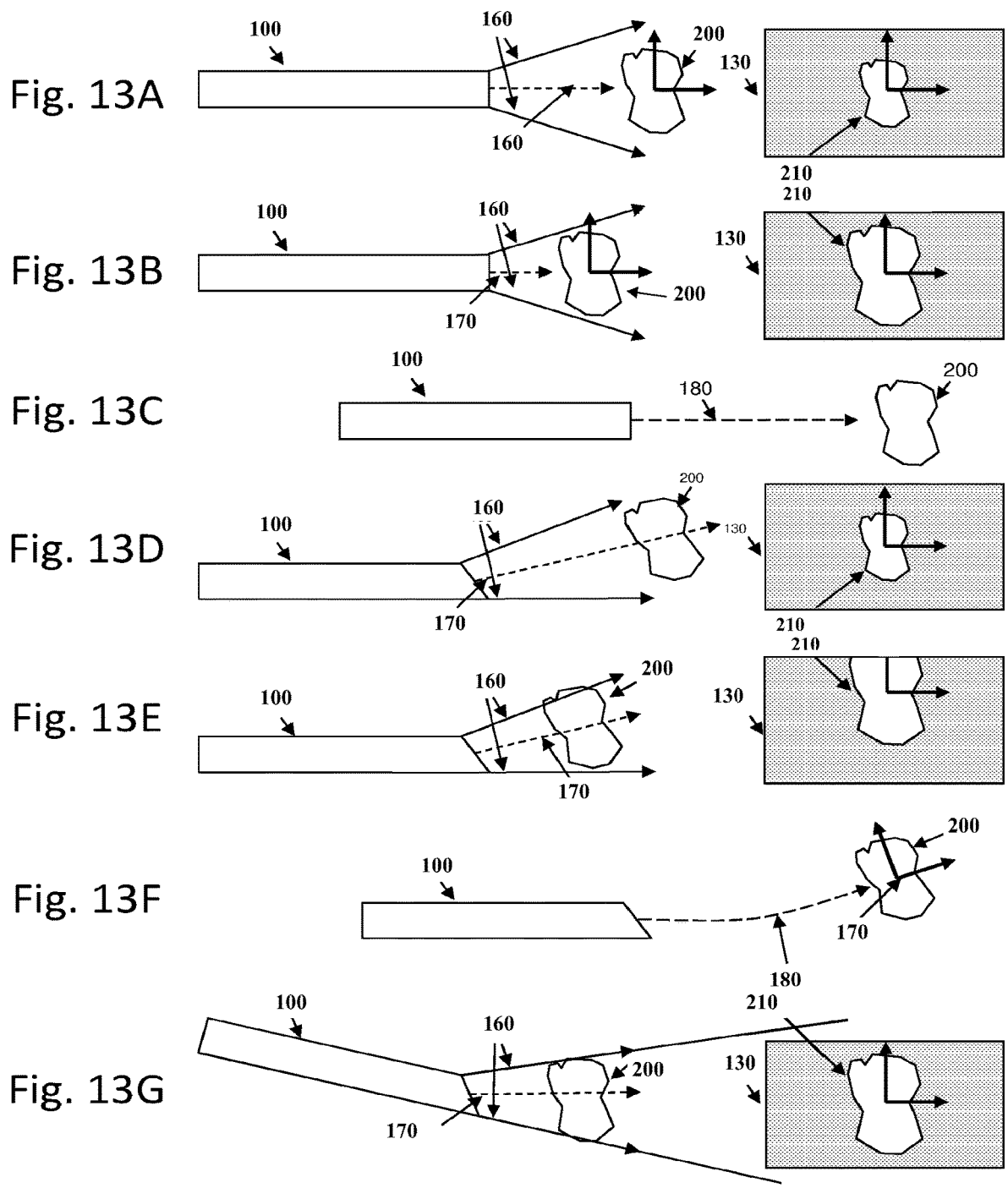

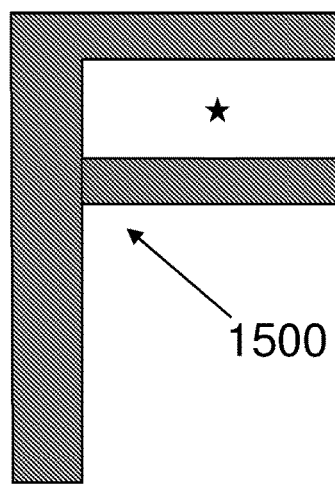
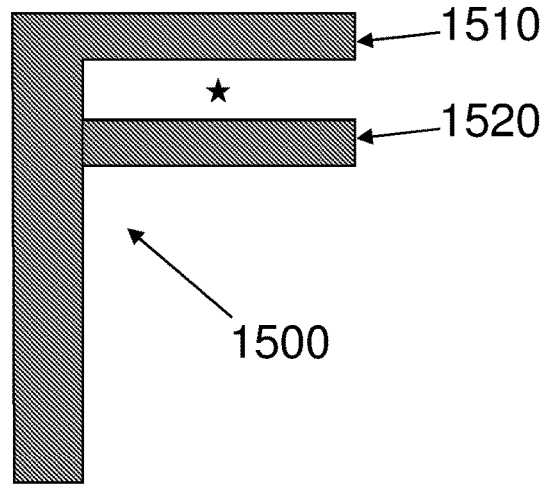
Fig. 15A        Fig. 15B
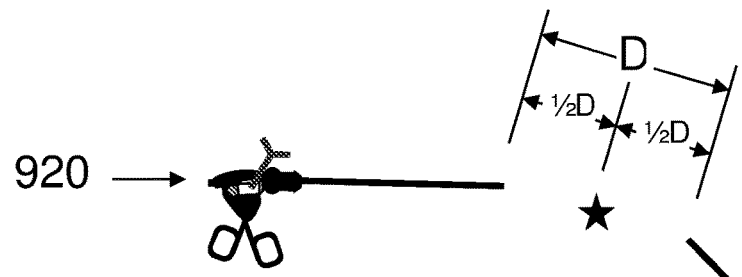
Fig. 16A
Fig. 16B Fig. 17A
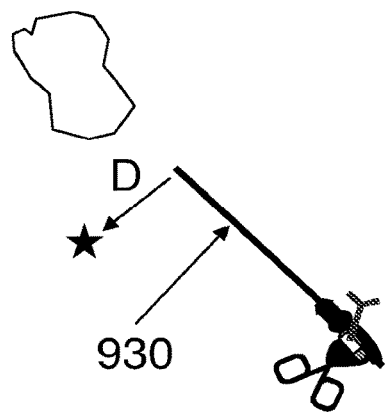
Fig. 17B
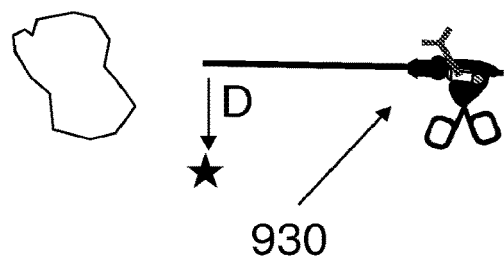
Fig. 18A
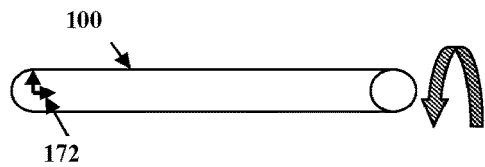
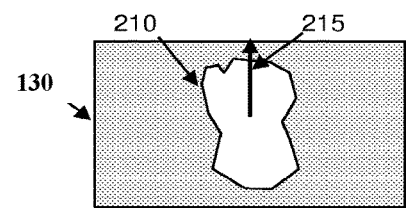
Fig. 18B
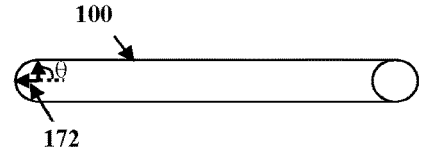
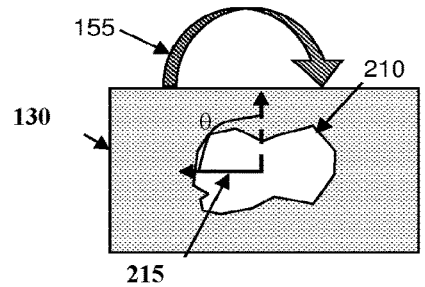
Fig. 18C
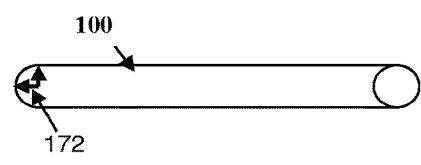
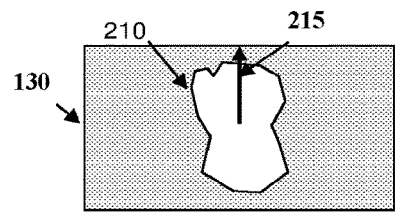

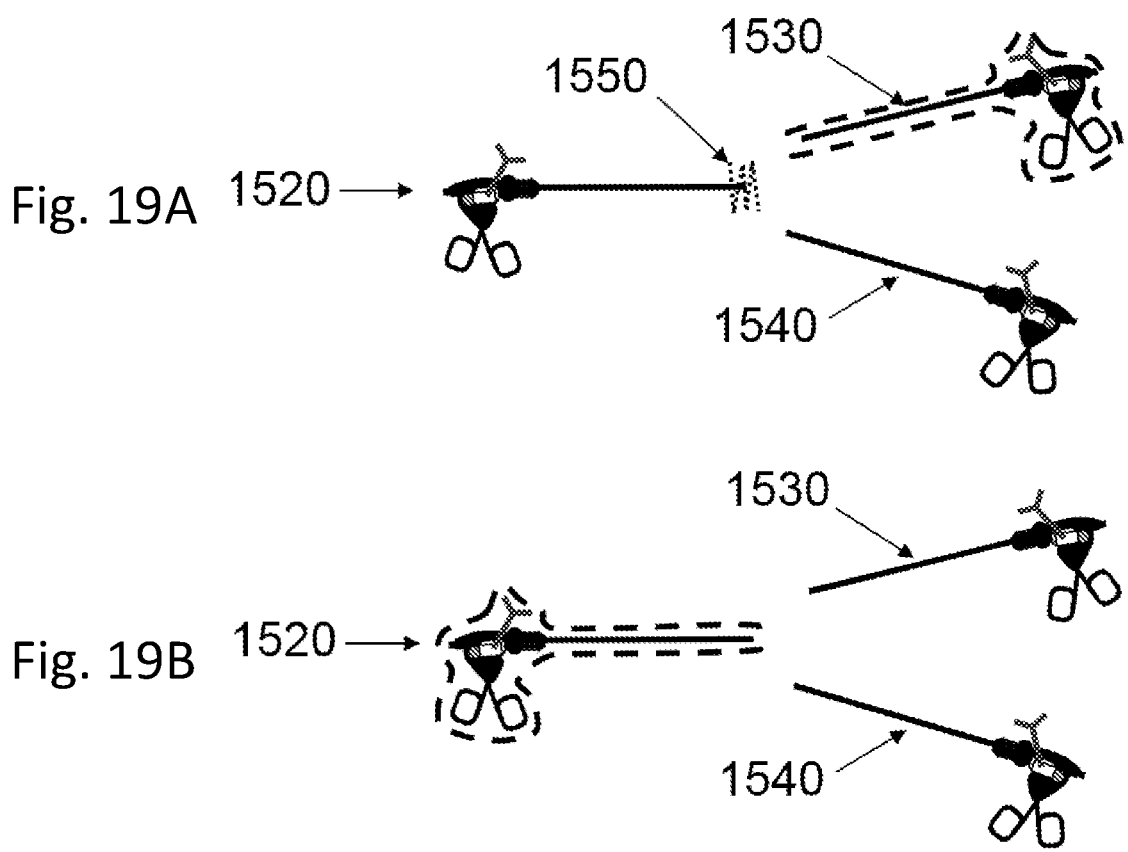

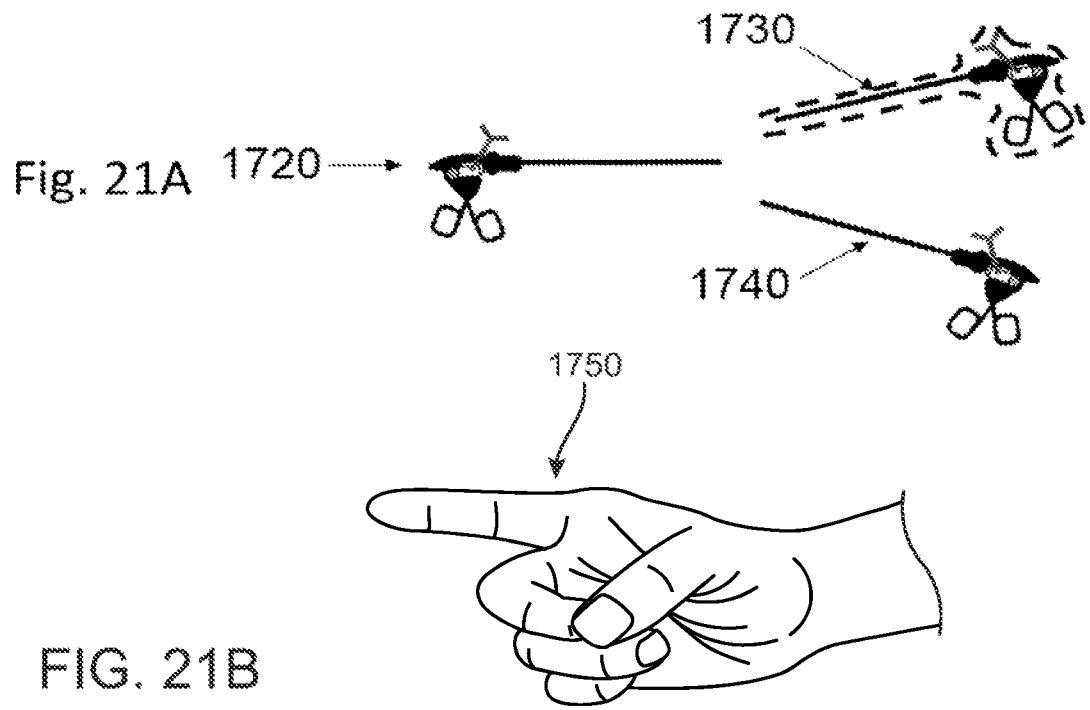
Fig. 21A
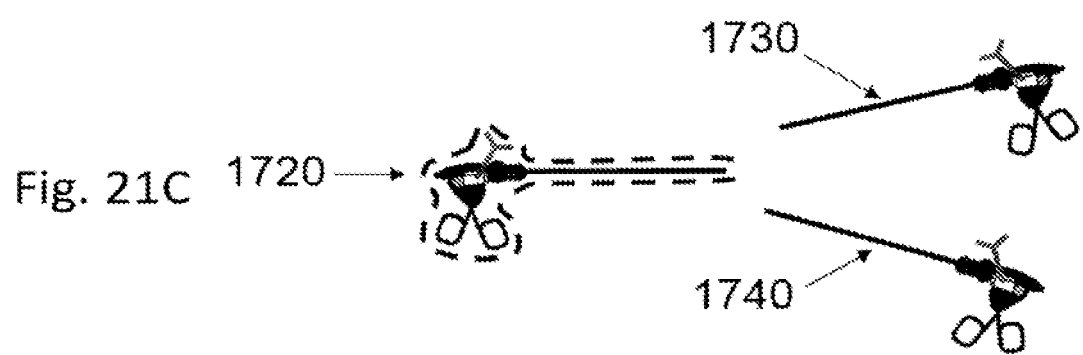
FIG. 21B
Fig. 21C

INTELLIGENT SURGICAL TOOL CONTROL SYSTEM FOR LAPAROSCOPIC SURGERIES

FIELD OF THE INVENTION

The present invention generally pertains to a system and method for providing an improved interface for laparoscopic surgeries

BACKGROUND OF THE INVENTION

Laparoscopic surgery is becoming increasingly popular with patients because the scars are smaller and their period of recovery is shorter. Laparoscopic surgery requires special training for the surgeon or gynecologist and for the theatre staff. The equipment is often expensive and is not available in all hospitals. During laparoscopic surgery, it is often required to shift the spatial placement of the endoscope in order to present the surgeon with an optimal view. Conventional laparoscopic surgery makes use of either human assistants that manually shift the instrumentation or robotic automated assistants (such as JP patent No. 06063003).

In laparoscopic surgery, the surgeon performs the operation through small holes using long instruments and observes the internal anatomy with an endoscope camera. The surgeon's performance is largely dependent on the camera's position relative to the instruments and on a stable image being shown on a monitor. In general, the surgeon needs a close-up view of the area in which he wants to work. However, there are times when an overview of a large portion of the working area, such as an overall view of the interior of the abdomen, is desirable.

U.S. patent application US2006/0281971 discloses a method and apparatus for presenting three-dimensional data to a physician to facilitate the flexible navigation of an endoscope and surgical instruments with respect to anatomical structures. In accordance with a first embodiment, a first set of data corresponding to a three dimensional model of a patient's anatomy is received. This three-dimensional model may be rendered from images taken in CT or MRI scanning. In accordance with this embodiment, this model is then combined with a second set of data corresponding to a view obtained from an endoscope. In another embodiment, the view from the endoscope is displayed as an inset image on a display of the three-dimensional image. In yet another embodiment, the three-dimensional image comprises a graphical representation of at least a first surgical instrument, such as said endoscope. The surgeon may select among various combinations of views and may zoom in or out from any particular view.

However, U.S. patent application US2006/0281971 does not disclose a means of controlling the endoscope.

U.S. Pat. No. 6,714,841 discloses an automated camera endoscope in which the surgeon is fitted with a head-mounted light source that transmits the head movements to a sensor, forming an interface that converts the movements to directions for the mechanical movement of an automated assistant. Alternatively, the automated assistant can incorporate a voice operated interface, a directional key interface, or other navigational interfaces. The above interfaces share the following drawbacks:

a. A single directional interface that provides limited feedback to the surgeon
b. A cumbersome serial operation for starting and stopping movement directions that requires the surgeon's constant attention, preventing the surgeon from keeping the flow of the surgical procedure.

Research has suggested that these systems divert the surgeon's focus from the major task at hand. Therefore, technologies assisted by magnets and image processing have been developed to simplify interfacing control. However, these improved technologies still fail to address another complicating interface aspect of laparoscopic surgery, in that they do not allow the surgeon to signal to automated assistants, to human assistants or to surgical colleagues which instrument his attention is focused on.

Hence there is still a long felt need for improving the interface between the surgeon, his surgical colleagues or human assistants and an endoscope system, for laparoscopic surgery

SUMMARY OF THE INVENTION

It is an object of the present invention to disclose a system for providing improved interface for laparoscopic surgeries.

It is another object of the present invention to provide an intelligent surgical tool control system, comprising:

a. at least one surgical tool;
b. at least one tool management system comprising at least one of the following:
   i. at least one maneuvering mechanism configured to maneuver said surgical tool in at least two dimensions,
   ii. at least one controller configured to control a member selected from a group consisting of: activation of at least a portion of at least one said surgical tool; deactivation of at least a portion of at least one said surgical tool; articulation of at least a portion of at least one said surgical tool; and any combination thereof; and
   iii. any combination thereof;
c. at least one indicating means configured to indicate at least one surgical event, said at least one surgical event is selected from a group consisting of: at least one movement of at least one moving element; presence of at least one item of interest, at least a portion of said item of interest having a location $3D_{current}$; and any combination thereof;
   said at least one movement is determinable if a current 3D position of said moving element, $3D_{current}$, is substantially different from a previous 3D position of the same, $3D_{previous}$;
d. either a wired or wireless communicable database for storing at least one member selected from a group consisting of: said $3D_{current}$; upon indication of said movement, consecutively storing said $3D_{current}$ and said $3D_{previous}$ of each of said moving element for any given time; said item of interest, and any combination thereof; and
e. at least one processor comprising a computer program in communication with said database and said at least one tool management system;
   wherein said computer program, when executed, is configured to identify, from said at least one surgical event, an output surgical procedure.

It is another object of the present invention to provide the system as defined above, wherein said output surgical procedure is identifiable as a predictable response to said at least one surgical event.

It is another object of the present invention to provide the system as defined above, wherein, upon said identification of said output surgical procedure, said system is configured to automatically perform said output surgical procedure.

It is another object of the present invention to provide the system as defined above, wherein, upon said identification of said output surgical procedure, said system is configured to provide a suggestion to perform said output surgical procedure.

It is another object of the present invention to provide the system as defined above, wherein at least two said surgical events result in a movement pattern, said movement pattern identifiable as an input surgical procedure.

It is another object of the present invention to provide the system as defined above, wherein said at least one surgical event is selected from a group consisting of: suturing, introducing a second at least one surgical tool to a surgical environment, removing at least one said surgical tool from a surgical environment, retraction of tissue, ligation, cauterizing, undermining, ablating tissue, incising tissue, blunt dissection, sharp dissection, removing tissue from the surgical environment, applying a clip, applying a clamp, applying a grasper, lavaging, swabbing, placing a swab, placing a sponge placing an absorbing medium, emplacing a stent, emplacing a drain, emplacing graft tissue, taking graft tissue, emplacing an artificial replacement item, identification of blood, identification of smoke, and any combination thereof.

It is another object of the present invention to provide the system as defined above, wherein said output surgical procedure is selected from a group consisting of: responsively maneuvering at least one said surgical tool, interactively activating at least one said surgical tool, interactively deactivating at least one said surgical tool, interactively articulating at least a portion of at least one said surgical tool, responsively maneuvering at least one second surgical tool, interactively activating at least one second surgical tool, interactively deactivating at least one second surgical tool, interactively articulating at least a portion of at least one second surgical tool, zooming in, zooming out, displaying a message, and any combination thereof.

It is another object of the present invention to provide the system as defined above, wherein said message is selected from a group consisting of: information about a patient, information about at least one said surgical tool, information about a procedure, suggestion of a procedure; a warning; display of said item of interest; and any combination thereof.

It is another object of the present invention to provide the system as defined above, wherein said item of interest is selected from a group consisting of: an article entering a field of view of a lens, an article moving, a likely collision between two articles, a collision between two articles, the occurrence of bleeding, smoke, the edges of an incision moving, activation or deactivation of at least one said surgical tool, articulation of at least one said surgical tool, contact between tissue and at least one said surgical tool, contact between at least two said surgical tools, contact between tissues, and any combination thereof.

It is another object of the present invention to provide the system as defined above, wherein at least one said surgical tool is an endoscope.

It is another object of the present invention to provide the system as defined above, wherein said endoscope is maneuverable.

It is another object of the present invention to provide the system as defined above, additionally configured to identify said output surgical procedure by detection of at least one input protocol, said input protocol comprising at least one predetermined movement wherein said predetermined movement is selected from a group consisting of operating at least one said surgical tool, orienting at least one said surgical tool at a predetermined angle within a field of view, shaking at least one said surgical tool, rotating at least one said surgical tool in a predetermined manner, translating at least one said surgical tool in a predetermined manner, positioning at least one said surgical tool at a predetermined position within said field of view, and any combination thereof.

It is another object of the present invention to provide the system as defined above, wherein said indicating means is selected from a group consisting of: a sensor; said at least one maneuvering mechanism, said at least one controller, imaging means, processing means to analyze an image of a field of view, processing means to calculate a 3D position of said at least one surgical tool; and any combination thereof.

It is another object of the present invention to provide the system as defined above, wherein said sensor is configured to indicate said current position of said moving element, $3D_{current}$.

It is another object of the present invention to provide the system as defined above, wherein said imaging means comprises an imaging system configured to real-time image said field of view.

It is another object of the present invention to provide the system as defined above, wherein said indicating computer program, when executed by a data processor, is configured to (i) real time image process said at least one image, and (ii) at least one of a group consisting of: detect said movement of said moving element; detect at least one said item of interest, and any combination thereof.

It is another object of the present invention to provide the system as defined above, wherein said moving element is selected from a group consisting of: movement of at least a portion of said at least one surgical tool, movement of the distal end of said at least one surgical tool, movement of a portion of a body of at least one operator, intended movement of said portion of said body of said operator, a thought of said operator, sound, and any combination thereof.

It is another object of the present invention to provide the system as defined above, wherein said body portion is selected from a group consisting of: at least a portion of an arm; at least a portion of a hand; at least a portion of a finger; at least a portion of a trunk; at least a portion of a head, an eye, and any combination thereof.

It is another object of the present invention to provide the system as defined above, wherein said maneuvering mechanism is configured to maneuver said surgical tool in at least 3 dimensions.

It is another object of the present invention to provide the system as defined above, wherein said at least one movement of said at least one moving element is an unwanted movement of said moving element.

It is another object of the present invention to provide the system as defined above, wherein said output surgical procedure for movement of said surgical tool, upon detection of said at least one said unwanted movement of said moving element, is that, for said moving element being said surgical tool, said unwanted movement is removed from said movement of said surgical tool; or, for said moving element not being said surgical tool, movement of said surgical tool is unaffected by said detection of said at least one unwanted movement.

It is another object of the present invention to provide the system as defined above, wherein said unwanted movement is selected from a group consisting of: involuntary movement of a body part, saccadic movement of an eye, vestibulo-ocular movement of an eye, winking an eye, blinking an eye, tremor of a body part, a tic in a body part, myoclonus of a body part, dystonia, and any combination thereof.

It is another object of the present invention to provide the system as defined above, wherein said output surgical procedure is configured to determine at least one allowed movement and at least one restricted movement of said at least one surgical tool from at least one historical movement of said at least one surgical tool according with at least one historical movement of said at least one surgical tool in at least one previous surgery.

It is another object of the present invention to provide the system as defined above, wherein said output surgical procedure comprises a communicable database storing n 3D spatial positions of a first at least one said surgical tool, where n is greater than or equal to 1, each of said n 3D spatial positions of said first at least one surgical tool according with at least two 3D spatial positions of at least one second surgical tool, a movement of said second surgical tool defined by said at least two 3D spatial positions of said at least one surgical tool; said output surgical procedure is configured to determine, from said stored at least n movements of said at least one second surgical tool and said stored n 3D spatial positions of said at least one said first surgical tool, a member selected from a group consisting of: at least one said allowed movement of said at least one first surgical tool and at least one said restricted movement of said at least one first surgical tool, such that said at least one allowed movement of said at least one first surgical tool is a movement in which said at least one first surgical tool is located substantially in at least one of said n first surgical tool 3D spatial positions according with said at least n movements of said at least one second surgical tool, and said at least one restricted movement is a movement in which said 3D spatial position of said least one first surgical tool is substantially different from all of said at least one first surgical tool n 3D spatial positions according with said at least n movements of said at least one second surgical tool.

It is another object of the present invention to provide the system as defined above, wherein said output surgical procedure comprises at least one rule according to which a member of a movement group consisting of at least one said allowed movement of said at least one surgical tool and at least one said restricted movement of said at least one surgical tool is determinable, such that each detected movement of said at least one surgical tool is determined as either one of said at least one allowed movements or one of said at least one restricted movements.

It is another object of the present invention to provide the system as defined above, wherein said at least one allowed movement is permitted by said surgical tool control system and said at least one restricted movement is denied by said surgical tool control system.

It is another object of the present invention to provide the system as defined above, wherein said at least one rule is selected from a predetermined set of rules consisting of: most used tool rule, right tool rule, left tool rule, field of view rule, no fly zone rule, route rule, environmental rule, operator input rule, proximity rule; collision prevention rule, history-based rule, tool-dependent allowed and restricted movement rule, preferred volume zone rule, preferred tool rule, movement detection rule, tagged tool rule, change of speed rule and any combination thereof.

It is another object of the present invention to provide the system as defined above, wherein said route rule comprises a communicable database storing predefined route in which said at least one surgical tool is configured to move within said surgical environment; said predefined route comprises n 3D spatial positions of said at least one surgical tool; n is an integer greater than or equal to 2; said at least one allowed movement is a movement in which said at least one surgical tool is located substantially in at least one of said n 3D spatial positions of said predefined route, and said at least one restricted movement is a movement in which said location of said at least one surgical tool is substantially different from said n 3D spatial positions of said predefined route.

It is another object of the present invention to provide the system as defined above, wherein said environmental rule comprises a communicable database; said communicable database configured to receive at least one real-time image of said surgical environment and is configured to perform real-time image processing of the same and to determine the 3D spatial position of a member of a hazard group consisting of: a hazard in said surgical environment, an obstacle in said surgical environment and any combination thereof; said environmental rule is configured to determine said member of said movement group according to said member of said hazard group, such that said at least one restricted movement is a movement in which said at least one surgical tool is located substantially in at least one of said 3D spatial positions, and said at least one allowed movement is a movement in which the location of said at least one surgical tool is substantially different from said 3D spatial positions.

It is another object of the present invention to provide the system as defined above, wherein said member of said hazard group is selected from a group consisting of tissue, a surgical tool, an organ, and any combination thereof.

It is another object of the present invention to provide the system as defined above, wherein said operator input rule comprises a communicable database; said communicable database is configured to receive an input from an operator of said system regarding said at least one allowed movement and said at least one restricted movement of said at least one surgical tool.

It is another object of the present invention to provide the system as defined above, wherein said input comprises n 3D spatial positions; n is an integer greater than or equal to 2; wherein at least one of which is defined as allowed location and at least one of which is defined as restricted location, such that said at least one allowed movement is a movement in which said at least one surgical tool is located substantially in at least one of said n 3D spatial positions, and said at least one restricted movement is a are movement in which the location of said at least one surgical tool is substantially different from said n 3D spatial positions.

It is another object of the present invention to provide the system as defined above, wherein said input comprises at least one input rule according to which said member of said movement group is determined, such that a spatial position of said at least one surgical tool is controlled by said surgical tool control system according to said member of said movement group.

It is another object of the present invention to provide the system as defined above, wherein said at least one input rule is selected from said predetermined set of rules.

It is another object of the present invention to provide the system as defined above, wherein said operator input rule converts at least one said allowed movement to at least one said restricted movement and at least one said restricted movement to at least one said allowed movement.

It is another object of the present invention to provide the system as defined above, wherein said proximity rule is configured to define a predetermined distance between at least two articles; said at least one allowed movement is a movement which is within a range or out of a range of said predetermined distance, and said at least one restricted movement is a movement which is out of a range or within a range of said predetermined distance.

It is another object of the present invention to provide the system as defined above, wherein said proximity rule is configured to define a predetermined angle between at least three articles; said at least one allowed movement is a movement which is within a range or out of a range of said predetermined angle, and said at least one restricted movement is a movement which is out of a range or within a range of said predetermined angle.

It is another object of the present invention to provide the system as defined above, wherein said collision prevention rule is configured to define a predetermined distance between said at least one surgical tool and an anatomical element within said surgical environment; said at least one allowed movement is a movement which is in a range that is larger than said predetermined distance, and said at least one restricted movement is a movement which is in a range that is smaller than said predetermined distance.

It is another object of the present invention to provide the system as defined above, wherein said anatomical element is selected from a group consisting of tissue, organ, another surgical tool and any combination thereof.

It is another object of the present invention to provide the system as defined above, wherein said right tool rule is configured to determine said at least one allowed movement of said at least one first surgical tool according to movement of said at least one second surgical tool positioned to right of said at least one first surgical tool; further wherein said left tool rule is configured to determine said at least one allowed movement of said at least one first surgical tool according to movement of said at least one second surgical tool positioned to left of at least one said first surgical tool.

It is another object of the present invention to provide the system as defined above, wherein said tagged tool rule comprises means configured to tag at least one said surgical tool within said surgical environment and to determine said at least one allowed movement of said endoscope to constantly track the movement of said at least one tagged surgical tool.

It is another object of the present invention to provide the system as defined above, wherein said field of view rule comprises a communicable database comprising n 3D spatial positions; n is an integer greater than or equal to 2; the combination of all of said n 3D spatial positions provides a predetermined field of view; said field of view rule is configured to determine said at least one allowed movement of said endoscope within said n 3D spatial positions so as to maintain a constant field of view, such that said at least one allowed movement is a movement in which said endoscope is located substantially in at least one of said n 3D spatial positions, and said at least one restricted movement is a movement in which the location of said endoscope is substantially different from said n 3D spatial positions.

It is another object of the present invention to provide the system as defined above, wherein said preferred volume zone rule comprises a communicable database comprising n 3D spatial positions; n is an integer greater than or equal to 2; said n 3D spatial positions provides said preferred volume zone; said preferred volume zone rule is configured to determine at least one said allowed movement of said surgical tool within said n 3D spatial positions and at least one said restricted movement of said surgical tool outside said n 3D spatial positions, such that said allowed movement is a movement in which said surgical tool is located substantially in at least one of said n 3D spatial positions, and said at least one restricted movement is a movement in which the location of said surgical tool is substantially different from said n 3D spatial positions.

It is another object of the present invention to provide the system as defined above, wherein said preferred tool rule comprises a communicable database, said database stores a preferred tool; said preferred tool rule is configured to determine said at least one allowed movement of said endoscope to constantly track movement of said preferred tool.

It is another object of the present invention to provide the system as defined above, wherein said no fly zone rule comprises a communicable database comprising n 3D spatial positions; n is an integer greater than or equal to 2; said n 3D spatial positions define a predetermined volume within said surgical environment; said no fly zone rule is configured to determine said at least one restricted movement if said movement is within said no fly zone and said at least one allowed movement if said movement is outside said no fly zone, such that said restricted movement is a movement in which said at least one surgical tool is located substantially in at least one of said n 3D spatial positions, and said at least one allowed movement is a movement in which the location of said at least one surgical tool is substantially different from said n 3D spatial positions.

It is another object of the present invention to provide the system as defined above, wherein said most used tool rule comprises a communicable database counting the amount of movement of each of said surgical tools; said most used tool rule is configured to constantly position said endoscope to track the movement of a most moved surgical tool.

It is another object of the present invention to provide the system as defined above, wherein said system is configured to provide an alert of said at least one restricted movement of said at least one surgical tool.

It is another object of the present invention to provide the system as defined above, wherein said alert is selected from a group consisting of audio signaling, voice signaling, light signaling, flashing signaling and any combination thereof.

It is another object of the present invention to provide the system as defined above, wherein said history-based rule comprises a communicable database storing each 3D spatial position of each of said surgical tool, such that each movement of each surgical tool is stored; said history-based rule is configured to determine said member of said movement group according to at least one historical movement of said at least one surgical tool, such that said at least one allowed movement is a movement in which said at least one surgical tool is located substantially in at least one of said 3D spatial positions, and said at least one restricted movement is a movements in which a location of said at least one surgical tool is substantially different from said n 3D spatial positions.

It is another object of the present invention to provide the system as defined above, wherein said tool-dependent allowed and restricted movement rule comprises a communicable database; said communicable database is configured to store at least one predetermined characteristic of at least one said surgical tool; said tool-dependent allowed and restricted movement rule is configured to determine said member of said movement group according to said at least one predetermined characteristic of said surgical tool; such that said at least one allowed movement is a movement of said endoscope which tracks said surgical tool having said at least one predetermined characteristic.

It is another object of the present invention to provide the system as defined above, wherein said at least one predetermined characteristic of said surgical tool is selected from a group consisting of: physical dimensions, structure, weight, sharpness, and any combination thereof.

It is another object of the present invention to provide the system as defined above, wherein said movement detection rule comprises a communicable database comprising at least one real-time 3D spatial position of each of said at least one surgical tool; said movement detection rule is configured to detect movement of said at least one surgical tool when a change in at least one said real-time 3D spatial position at least one is received, such that at least one said allowed movement is a movement in which said endoscope is re-directed to focus on said moving surgical tool.

It is another object of the present invention to provide the system as defined above, wherein said moving element is selected from a group consisting of: movement of at least a portion of at surgical tool, movement of at least a portion of the body of at least one operator, intended movement of at least a portion of the body of at least one operator, a brain signal from at least one operator, a sound signal and any combination thereof.

It is another object of the present invention to provide a method for intelligent control of a surgical tool control system, comprising steps of:
a. providing an intelligent surgical tool control system, comprising:
  i. at least one surgical tool;
  ii. at least one tool management system comprising at least one of the following:
    (a) at least one maneuvering mechanism configured to maneuver said surgical tool in at least two dimensions,
    (b) at least one controller configured to control a member selected from a group consisting of: activation of at least a portion of at least one said surgical tool; deactivation of at least a portion of at least one said surgical tool; articulation of at least a portion of at least one said surgical tool; and any combination thereof; and
    (c) any combination thereof;
  iii. at least one indicating means configured to indicate at least one surgical event, said at least one surgical event is selected from a group consisting of: at least one movement of at least one moving element; presence of at least one item of interest, at least a portion of said item of interest having a location $3D_{current}$; and any combination thereof;
    said at least one movement is determinable if a current 3D position of said moving element, $3D_{current}$, is substantially different from a previous 3D position of the same, $3D_{previous}$;
  iv. either a wired or wireless communicable database for storing at least one member selected from a group consisting of: said $3D_{current}$; upon indication of said movement, consecutively storing said $3D_{current}$ and said $3D_{previous}$ of each of said moving element; said item of interest, and any combination thereof; and
  v. at least one processor comprising a computer program in communication with said database and said at least one tool management system;
b. indicating said at least one surgical event;
c. storing said at least one member selected from said group consisting of: (i) said $3D_{current}$; (ii) upon indication of said movement, consecutively storing said $3D_{current}$ and said $3D_{previous}$ of each of said moving element; (iii) said item of interest, and any combination thereof; and
d. real-time processing said at least one member selected from a group consisting of: (i) said $3D_{current}$; (ii) said $3D_{current}$ and said $3D_{previous}$ of each of said moving element; (iii) said item of interest, and any combination thereof;
thereby identifying said output surgical procedure.

It is another object of the present invention to provide the method as defined above, wherein said output surgical procedure is identifiable as a predictable response to said at least one surgical event.

It is another object of the present invention to provide the method as defined above, additionally comprising step of, upon said identifying of said output surgical procedure, automatically performing said output surgical procedure.

It is another object of the present invention to provide the method as defined above, additionally comprising step of, upon said identifying of said output surgical procedure, providing a suggestion to perform said output surgical procedure.

It is another object of the present invention to provide the method as defined above, additionally comprising steps of identifying a movement pattern from two said surgical events and of identifying, from said movement pattern, identifiable an input surgical procedure.

It is another object of the present invention to provide the method as defined above, additionally comprising step of selecting said at least one surgical event from a group consisting of: suturing, introducing a second at least one surgical tool to a surgical environment, removing at least one said surgical tool from a surgical environment, retraction of tissue, ligation, cauterizing, undermining, ablating tissue, incising tissue, blunt dissection, sharp dissection, removing tissue from the surgical environment, applying a clip, applying a clamp, applying a grasper, lavaging, swabbing, placing a swab, placing a sponge placing an absorbing medium, emplacing a stent, emplacing a drain, emplacing graft tissue, taking graft tissue, emplacing an artificial replacement item, identification of blood, identification of smoke, and any combination thereof.

It is another object of the present invention to provide the method as defined above, additionally comprising step of selecting said output surgical procedure from a group consisting of: responsively maneuvering at least one said surgical tool, interactively activating at least one said surgical tool, interactively deactivating at least one said surgical tool, interactively articulating at least a portion of at least one said surgical tool, responsively maneuvering at least one second surgical tool, interactively activating at least one second surgical tool, interactively deactivating at least one second surgical tool, interactively articulating at least a portion of at least one second surgical tool, zooming in, zooming out, displaying a message, and any combination thereof.

It is another object of the present invention to provide the method as defined above, additionally comprising step of selecting said message from a group consisting of: information about a patient, information about at least one said surgical tool, information about a procedure, suggestion of a procedure; a warning; display of said item of interest; and any combination thereof.

It is another object of the present invention to provide the method as defined above, additionally comprising step of selecting said item of interest from a group consisting of: an article entering a field of view of a lens, an article moving, a likely collision between two articles, a collision between two articles, the occurrence of bleeding, smoke, the edges of an incision moving, activation or deactivation of at least one said surgical tool, articulation of at least one said surgical tool, contact between tissue and at least one said surgical tool, contact between at least two said surgical tools, contact between tissues, and any combination thereof.

It is another object of the present invention to provide the method as defined above, additionally comprising step of selecting said surgical tool to be an endoscope.

It is another object of the present invention to provide the method as defined above, additionally comprising step of maneuvering said endoscope.

It is another object of the present invention to provide the method as defined above, additionally comprising steps of identifying said output surgical procedure by detecting at least one input protocol, said input protocol comprising at least one predetermined movement, and selecting said predetermined movement from a group consisting of: operating at least one said surgical tool, orienting at least one said surgical tool at a predetermined angle within a field of view, shaking at least one said surgical tool, rotating at least one said surgical tool in a predetermined manner, translating at least one said surgical tool in a predetermined manner, positioning at least one said surgical tool at a predetermined position within said field of view, and any combination thereof.

It is another object of the present invention to provide the method as defined above, additionally comprising step of selecting said identifying means from a group consisting of: a sensor; said at least one controller, imaging means, processing means to analyze an image of a field of view, processing means to calculate a 3D position of said at least one surgical tool; and any combination thereof.

It is another object of the present invention to provide the method as defined above, additionally comprising step of indicating said current position of said moving element, $3D_{current}$ by means of said sensor.

It is another object of the present invention to provide the method as defined above, additionally comprising step of providing said imaging means via an imaging system configured to real-time image said field of view.

It is another object of the present invention to provide the method as defined above, additionally comprising step of executing said indicating computer program, thereby (i) real time image processing said at least one image, and (ii) at least one of a group consisting of: detecting said movement of said moving element; detecting at least one said item of interest, and any combination thereof.

It is another object of the present invention to provide the method as defined above, additionally comprising step of selecting said moving element from a group consisting of: a movement of at least a portion of said at least one surgical tool, a movement of the distal end of said at least one surgical tool, a movement of a portion of a body of at least one operator, intended movement of said portion of said body of said operator, a thought of said operator, sound, and any combination thereof.

It is another object of the present invention to provide the method as defined above, additionally comprising step of selecting said body portion from a group consisting of: at least a portion of an arm; at least a portion of a hand; at least a portion of a finger; at least a portion of a trunk; at least a portion of a head, an eye, and any combination thereof.

It is another object of the present invention to provide the method as defined above, additionally comprising step of maneuvering said surgical tool in at least 3 dimensions.

It is another object of the present invention to provide the method as defined above, additionally comprising step of selecting at least one said identifiable movement to be an unwanted movement of said moving element.

It is another object of the present invention to provide the method as defined above, additionally comprising step of selecting said output surgical procedure for movement of said surgical tool, upon detection of at least one said unwanted movement of said moving element, to be that, for said moving element being said surgical tool, said unwanted movement is removed from said movement of said surgical tool; or, for said moving element not being said surgical tool, movement of said surgical tool is unaffected by said detection of said at least one unwanted movement.

It is another object of the present invention to provide the method as defined above, additionally comprising step of selecting said unwanted movement from a group consisting of: involuntary movement of a body part, saccadic movement of an eye, vestibulo-ocular movement of an eye, winking an eye, blinking an eye, tremor of a body part, a tic in a body part, myoclonus of a body part, dystonia, and any combination thereof.

It is another object of the present invention to provide the method as defined above, additionally comprising step of said output surgical procedure determining at least one allowed movement and at least one restricted movement of said at least one surgical tool from at least one historical movement of said at least one surgical tool according with at least one historical movement of said at least one surgical tool in at least one previous surgery.

It is another object of the present invention to provide the method as defined above, wherein said output surgical procedure comprises a communicable database storing n 3D spatial positions of a first at least one said surgical tool, where n is greater than or equal to 1, each of said n 3D spatial positions of said first at least one surgical tool according with at least two 3D spatial positions of at least one second surgical tool, a movement of said second surgical tool is defined by said at least two 3D spatial positions of said at least one second surgical tool; said output surgical procedure is configured to determine, from said stored at least n movements of said at least one second surgical tool and said stored n 3D spatial positions of said at least one said first surgical tool, a member selected from a group consisting of: at least one said allowed movement of said at least one said first surgical tool and at least one said restricted movement of said at least one said first surgical tool; such that said allowed movement of said at least one first surgical tool is a movement in which said at least one first surgical tool is located substantially in one of said at least one first surgical tool n 3D spatial positions according with said at least n movements of said second surgical tool, and said at least one restricted movement is a movement in which said 3D spatial position of said at least one first surgical tool is substantially different from all of said at least one first surgical tool n 3D spatial positions according with said at least n movements of said at least one second surgical tool.

It is another object of the present invention to provide the method as defined above, additionally comprising step of providing said output surgical procedure with at least one rule according to which a member of a movement group consisting of: said at least one allowed movement of said at least one surgical tool and said at least one restricted movement of said at least one surgical tool is determinable, such that each detected movement of said at least one surgical tool is determinable as either an allowed movement or as a restricted movement s.

It is another object of the present invention to provide the method as defined above, wherein said at least one allowed movement is permitted by said surgical tool control system and said at least one restricted movement is denied by said surgical tool control system.

It is another object of the present invention to provide the method as defined above, additionally comprising step of selecting said at least one rule from a predetermined set of rules consisting of: most used tool, right tool rule, left tool rule, field of view rule, no fly zone rule, route rule, an environmental rule, an operator input rule, a proximity rule; a collision prevention rule, preferred volume zone rule, preferred tool rule, movement detection rule, a history-based rule, a tool-dependent allowed and restricted movement rule, tagged tool rule, change of speed rule and any combination thereof.

It is another object of the present invention to provide the method as defined above, wherein said route rule comprises a communicable database storing predefined route in which said at least one surgical tool is configured to move within said surgical environment; said predefined route comprises n 3D spatial positions of said at least one surgical tool; n is an integer greater than or equal to 2; said at least one allowed movement is a movement in which said at least one surgical tool is located substantially in at least one of said n 3D spatial positions of said predefined route, and said at least one restricted movement is a movement in which the location of said at least one surgical tool is substantially different from said n 3D spatial positions of said predefined route.

It is another object of the present invention to provide the method as defined above, wherein said environmental rule comprises a communicable database; said communicable database is configured to receive at least one real-time image of said surgical environment and is configured to perform real-time image processing of the same and to determine the 3D spatial position of a member of a hazard group consisting of: a hazard in said surgical environment, an obstacle in said surgical environment and any combination thereof; said environmental rule is configured to determine said member of said movement group according to said member of said hazard group, such that said at least one restricted movement is a movement in which said at least one surgical tool is located substantially in at least one of said 3D spatial positions, and said at least one allowed movement is a movement in which the location of said at least one surgical tool is substantially different from said 3D spatial positions.

It is another object of the present invention to provide the method as defined above, wherein said member of said hazard group is selected from a group consisting of tissue, a surgical tool, an organ, and any combination thereof.

It is another object of the present invention to provide the method as defined above, wherein said operator input rule comprises a communicable database; said communicable database is configured to receive an input from an operator of said system regarding said at least one allowed movement and said at least one restricted movement of said at least one surgical tool.

It is another object of the present invention to provide the method as defined above, wherein said input comprises n 3D spatial positions; n is an integer greater than or equal to 2; wherein at least one of which is defined as allowed location and at least one of which is defined as restricted location, such that said at least one allowed movement is a movement in which said at least one surgical tool is located substantially in at least one of said n 3D spatial positions, and said at least one restricted movement is a movement in which the location of said at least one surgical tool is substantially different from said n 3D spatial positions.

It is another object of the present invention to provide the method as defined above, wherein said input comprises at least one rule according to which said member of said movement group is determined, such that the spatial position of said at least one surgical tool is controlled by said surgical tool control system according to said member of said movement group.

It is another object of the present invention to provide the method as defined above, additionally comprising step of selecting said rule from said predetermined set of rules.

It is another object of the present invention to provide the method as defined above, wherein said operator input rule converts at least one said allowed movement to at least one said restricted movement and at least one said restricted movement to at least one said allowed movement.

It is another object of the present invention to provide the method as defined above, wherein said proximity rule is configured to define a predetermined distance between at least two articles; at least one said allowed movement is a movement which is within a range or out of a range of said predetermined distance, and at least one said restricted movement is a movement which is out of a range or within a range of said predetermined distance.

It is another object of the present invention to provide the method as defined above, wherein said proximity rule is configured to define a predetermined angle between at least articles; said at least one allowed movement is a movement which is within a range or out of a range of said predetermined angle, and said at least one restricted movement is a movement which is out of a range or within a range of said predetermined angle It is another object of the present invention to provide the method as defined above, wherein said collision prevention rule is configured to define a predetermined distance between said at least one surgical tool and an anatomical element within said surgical environment; said at least one allowed movement is a movement which is in a range that is larger than said predetermined distance, and said at least one restricted movement is a movement which is in a range that is smaller than said predetermined distance.

It is another object of the present invention to provide the method as defined above, wherein said anatomical element is selected from a group consisting of tissue, organ, another surgical tool and any combination thereof.

It is another object of the present invention to provide the method as defined above, wherein said right tool rule is configured to determine said at least one allowed movement of a first said surgical tool according to the movement of a second said surgical tool positioned to right of said first said surgical tool; further wherein said left tool rule is configured to determine said at least one allowed movement of said first said surgical tool according to the movement of said second said surgical tool positioned to left of said first said surgical tool.

It is another object of the present invention to provide the method as defined above, wherein said tagged tool rule comprises means configured to tag at least one said surgical tool within said surgical environment and to determine said at least one allowed movement of said endoscope to constantly track the movement of at least one said tagged surgical tool.

It is another object of the present invention to provide the method as defined above, wherein said field of view rule comprises n 3D spatial positions; n is an integer greater than or equal to 2; the combination of all of said n 3D spatial positions provides a predetermined field of view; said field of view rule is configured to determine said at least one allowed movement of said endoscope within said n 3D spatial positions so as to maintain a constant field of view, such that said at least one allowed movement is a movement in which said endoscope is located substantially in at least one of said n 3D spatial positions, and said at least one restricted movement is a movement in which the location of said endoscope is substantially different from said n 3D spatial positions.

It is another object of the present invention to provide the method as defined above, wherein said preferred volume zone rule comprises a communicable database comprising n 3D spatial positions; n is an integer greater than or equal to 2; said n 3D spatial positions provides said preferred volume zone; said preferred volume zone rule is configured to determine at least one said allowed movement of said at least one surgical tool within said n 3D spatial positions and at least one said restricted movement of said endoscope outside said n 3D spatial positions, such that said at least one allowed movement is a movements in which said at least one said surgical tool is located substantially in at least one of said n 3D spatial positions, and said at least one restricted movement is a movement in which the location of said at least one surgical tool is substantially different from said n 3D spatial positions.

It is another object of the present invention to provide the method as defined above, wherein said preferred tool rule comprises a communicable database, said database stores a preferred tool; said preferred tool rule is configured to determine said at least one allowed movement of said endoscope to constantly track the movement of said preferred tool.

It is another object of the present invention to provide the method as defined above, wherein said no fly zone rule comprises n 3D spatial positions; n is an integer greater than or equal to 2; said n 3D spatial positions define a predetermined volume within said surgical environment; said no fly zone rule is configured to determine said at least one restricted movement if said movement is within said no fly zone and said at least one allowed movement if said movement is outside said no fly zone, such that said at least one restricted movement is a movement in which said at least one surgical tool is located substantially in at least one of said n 3D spatial positions, and said at least one allowed movement is a movement in which the location of said at least one surgical tool is substantially different from said n 3D spatial positions.

It is another object of the present invention to provide the method as defined above, wherein said most used tool rule comprises a database counting the amount of movement of each of said surgical tools; said most used tool rule is configured to constantly position said endoscope to track the movement of a most moved surgical tool.

It is another object of the present invention to provide the method as defined above, additionally comprising step of providing an alert of at least one restricted movement of said at least one surgical tool.

It is another object of the present invention to provide the method as defined above, wherein said step of providing an alert is performed by at least one selected from a group consisting of audio signaling, voice signaling, light signaling, flashing signaling and any combination thereof.

It is another object of the present invention to provide the method as defined above, wherein said history-based rule comprises a communicable database storing each 3D spatial position of each of said surgical tool, such that each movement of each surgical tool is stored; said history-based rule is configured to determine said member of said movement group according to at least one historical movement of said at least one surgical tool, such that said at least one allowed movement is a movement in which said at least one surgical tool is located substantially in at least one of said 3D spatial positions, and said at least one restricted movement is a movement in which the location of said at least one surgical tool is substantially different from said n 3D spatial positions.

It is another object of the present invention to provide the method as defined above, wherein said tool-dependent allowed and restricted movement rule comprises a communicable database; said communicable database is configured to store at least one predetermined characteristic of at least one said surgical tool; said tool-dependent allowed and restricted movement rule is configured to determine said member of said movement group according to said at least one predetermined characteristic of said surgical tool such that said at least one allowed movement as is a movement of said endoscope which tracks said surgical tool having said at least one predetermined characteristics.

It is another object of the present invention to provide the method as defined above, wherein said at least one predetermined characteristic of said surgical tool is selected from a group consisting of: physical dimensions, structure, weight, sharpness, and any combination thereof.

It is another object of the present invention to provide the method as defined above, wherein said movement detection rule comprises a communicable database comprising at least one real-time 3D spatial position of each of said at least one surgical tool; said movement detection rule is configured to detect movement of said at least one surgical tool when a change in at least one said real-time 3D spatial position is received, such that at least one said allowed movement is a movement in which said endoscope is directed to focus on said moving surgical tool.

It is another object of the present invention to provide the method as defined above, additionally comprising step of selecting said moving element from a group consisting of: movement of at least a portion of at surgical tool, movement of at least a portion of the body of at least one operator, intended movement of at least a portion of the body of at least one operator, a brain signal from at least one operator, a sound signal and any combination thereof.

at least one

BRIEF DESCRIPTION OF THE FIGURES

In order to understand the invention and to see how it may be implemented in practice, and by way of non-limiting example only, with reference to the accompanying drawing, in which FIG. 1A-D schematically illustrates operation of an embodiment of a tracking system with collision avoidance system;

FIG. 11A-C schematically illustrates operation of an embodiment of the proximity function/rule;

FIGS. 13A-G schematically illustrates an embodiment of a tracking system with a constant field of view rule/function;

FIGS. 15A-B, FIGS. 16A-B and FIGS. 17A-B schematically illustrate embodiments of a tracking system with a fixed point rule/function;

FIGS. 18A-C schematically illustrate an embodiment of a tracking system with a virtual rotation of scene rule/function;

FIGS. 19A-B and 20 A-B schematically illustrate an embodiment of a tracking system with an input protocol in which a tool is moved;

FIGS. 21A-C, 22A-C, 23A-C and 24A-C schematically illustrate an embodiment of a tracking system with an input protocol in which a portion of the body of an operator is moved;

DETAILED DESCRIPTION OF THE PREFERRED EMBODIMENTS

Figure 1A:
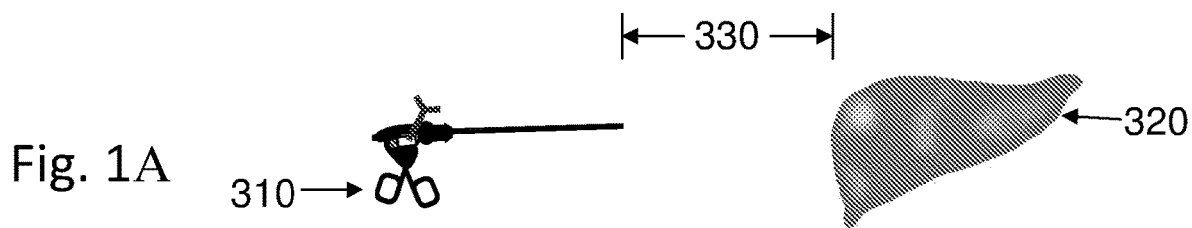
Figure 1B:
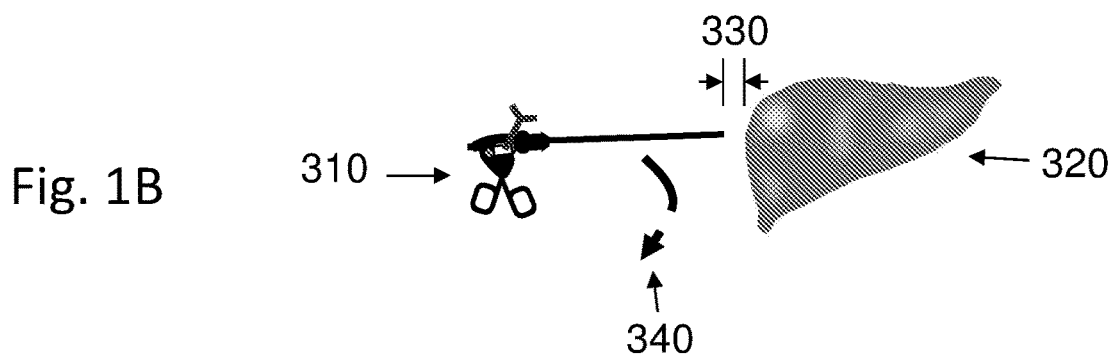

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a means and method for providing augmented reality endoscopic image.

The term 'camera' hereinafter refers to an image acquiring element. Examples of a camera include, but are not limited to, a CCD array and an electromagnetic system such as a TV camera.

The term 'endoscope distal end' hereinafter refers to the end of the endoscope that is inside the patient. The camera is attached to the other side of the endoscope, the proximal end, which is outside of the patient's abdomen.

The term 'field of view' (FOV) hereinafter refers to the scene visible to the camera.

The term 'display view' hereinafter refers to the scene displayable to the viewer.

The term 'structured light' hereinafter refers to a method of producing 3D images using a single 2D camera. In the structured light method, the object is illuminated by at least one set of rays of light, each ray emitted from a known position and a known direction, and each ray emitted at a known time. For each known time, a 2D camera image is created from light reflected from spots created by rays existing at that time. Initially, a known calibration object is illuminated. From the known shape, size and position of the calibration object and from the locations in the camera images of the reflected light, mathematical matrices can be calculated. These matrices enable calculation of the 3D location of the surface of an unknown object, when the unknown object is illuminated by the same set of rays as illuminated the calibration object.

The term 'virtual marker' hereinafter refers to a computer-generated mark, label or other identifier attached to a point or region on the display image. A virtual marker has no physical existence, unlike a tag, wire, or chemical such as luminescent paint physically associated with a portion of the patient.

The term 'toggle' refers hereinafter to switching between one tagged surgical tool and another.

The term 'surgical environment' refers hereinafter to any anatomical part within the human body which may be in the surroundings of a surgical instrument. The environment may comprise: organs, body parts, walls of organs, arteries, veins, nerves, a region of interest, or any other anatomical part of the human body.

The term 'region of interest' refers hereinafter to any region within the human body which may be of interest to the operator of the system of the present invention. The region of interest may be, for example, an organ to be operated on, a restricted area, a surgical instrument, or any other region within the human body.

The term 'spatial position' refers hereinafter to a predetermined spatial location and/or orientation of an object (e.g., the spatial location of the endoscope, the angular orientation of the endoscope, and any combination thereof).

The term 'restricted area' refers hereinafter to a predetermined volume within which a surgical tool (e.g., an endoscope) is prohibited to be spatially positioned.

The term 'preferred area' refers hereinafter to predetermined volume within which a surgical tool (e.g., an endoscope) is allowed and/or preferred to be spatially positioned.

The term 'automated assistant' refers hereinafter to any mechanical device (including but not limited to a robotic device) that can maneuver a surgical or endoscopic instrument and control the position of a surgical or endoscopic instrument, and that can in addition be configured to receive commands from a remote source.

The term 'tool', 'surgical tool' or 'surgical instrument' refers hereinafter to any instrument or device introducible into the human body. The term may refer to any location on the tool. For example it can refer to the tip of the same, the body of the same and any combination thereof. It should be further pointed that the following description may refer to a surgical tool or surgical instrument as an endoscope.

The term 'provide' refers hereinafter to any process (visual, tactile, or auditory) by which an instrument, computer, controller, or any other mechanical or electronic device can report the results of a calculation or other operation.

The term 'automatic' or 'automatically' refers to any process that proceeds without the necessity of direct intervention or action on the part of a human being.

The term 'allowed movement' refers hereinafter to any movement of a surgical tool which is permitted according to a predetermined set of rules.

The term 'restricted movement' refers hereinafter to any movement of a surgical tool which is forbidden according to a predetermined set of rules. For example, one rule, according to the present invention, provides a preferred volume zone rule which defines a favored zone within the surgical environment. Thus, according to the present invention an allowed movement of a surgical tool or the endoscope is a movement which maintains the surgical tool within a favored zone; and a restricted movement of a surgical tool is a movement which extracts (or moves) the surgical tool outside an unfavored zone.

The term 'time step' refers hereinafter to the working time of the system. At each time step, the system receives data, e.g., from sensors or from maneuvering systems, and commands from operators, processes the data and commands and executes actions. The time step size is the elapsed time between time steps.

The term 'encephalographic pattern' or 'brain wave' refers hereinafter to a pattern of electrical impulses of a living brain. Encephalographic patterns can be indicative of movement of a portion of the body (the brain is sending a signal to control movement), of intent to move a portion of the body (the brain intends to or is preparing to send a movement control signal), of an emotional state (worry, fear, pleasure, etc.) and any combination thereof. The body portion to be moved can include a limb or portion thereof, an eye, the mouth, throat or vocal cords (speech), the torso or neck, or any other movable portion of the body.

The term 'moving element' refers hereinafter to either an object whose movement can be sensed or a means of sensing future movement of the object. A movement of a moving element can include, but is not limited to, movement of at least a portion of at surgical tool (such as, for non-limiting example the distal end of a surgical tool), movement of at least a portion of the body of at least one operator, intended movement of at least a portion of the body of at least one operator, a brain signal from at least one operator, a sound signal and any combination thereof. Movement of the portion of the body can be determined, for non-limiting example, via brain signals (e.g., the brain signals commanding a movement), via sensors measuring the movement of the portion of the body, or via electrical or magnetic signals indicating change in at least one muscle. Intended movement can be measured via brain signals from the operator (for non-limiting examples, "next, I will open that grasper", or "that's dangerous—we had better stop it"). Sound signals can include voice commands or other predetermined sound patterns.

The term 'article' refers hereinafter to an object in the surgical environment. Articles can include, but are not limited to, of at least a portion of a tool, at least a portion of an endoscope, at least a portion of a body, at least a portion of an organ, at least a portion of a tissue, at least a portion of an object and any combination thereof, where tissue refers to a structure in the body including, but not limited to, a membrane, a ligament, fat, mesentery, a blood vessel, a nerve, bone, cartilage, a tumor, a cyst and any combination thereof and an object can include a swab, suture thread, a towel, a sponge, a knife blade, a scalpel blade, a pin, a safety pin, a tip, a tube, an adapter, a guide such as a cutting guide, a measurement device and any combination thereof.

The terms 'output protocol' or 'output surgical procedure' refer hereinafter to an action or set of actions carried out by the system. Output protocols or output surgical procedures can comprise, but are not limited to, tagging an article in the surgical environment, tracking an article in the surgical environment, zooming an endoscope, activating or deactivating a tool or an endoscope, articulating a tool or endoscope, and any combination thereof.

The term 'surgical event' or 'input event' refers hereinafter to at least one movement of at least one moving element or to at least one occurrence within the surgical cavity for which a determinable output surgical procedure exists. A non-limiting example of a surgical event which comprises movement is suturing; the associated output surgical procedure would comprise enlarging the visible image so as to focus in on the area of the knot being tied during a tying operation, and zooming out to follow the line of the incision while traversing to a next suture. A non-limiting example of a surgical event which comprises an occurrence is the presence of smoke within the surgical cavity; the output surgical procedure could be to start fluid flow to clear the smoke from the surgical cavity.

The term 'input protocol' refers hereinafter to a command or set of commands which indicate to the system that a predefined output protocol is to be carried out. Input protocols can include, but are not limited to, shaking the tool or other moving element, rotating a tool or other moving element in a predetermined manner, translating a tool or other moving element in a predetermined manner, and any combination thereof. The predetermined movement can be moving a tool or other moving element along an arc, where the arc can be a portion of a circle, a portion of an oval, a portion of an ellipse, a portion of a polynomial, a portion of a trigonometric function, a portion of a hyperbolic function and any combination thereof, moving a tool or other moving element in a straight line, moving a tool or other moving element in a zigzag, and any combination thereof.

Unless otherwise stated, all examples provided herein are non-limiting.

Laparoscopic surgery, also called minimally invasive surgery (MIS), is a surgical technique in which operations in the abdomen are performed through much smaller incisions than traditional surgical procedures (usually 0.5-1.5 cm as compared to usually 15-20 cm). The key element in laparoscopic surgery is the use of an endoscope, which is a device configured to view the scene within the body and which is usually inserted through a 5 mm or 10 mm cannula or trocar to enable viewing of the operative field. Either an imaging device is placed at the distal end of the endoscope, or a rod lens system or fiber optic bundle is used to direct the image to the proximal end of the endoscope. A light source is provided to illuminate the operative field; this light source can be attached to the endoscope.

The abdomen is usually injected with carbon dioxide gas to create a working and viewing space. The abdomen is essentially blown up like a balloon (insufflated), elevating the abdominal wall above the internal organs like a dome. Within this space, various medical procedures can be carried out.

In many cases, other information is available to the surgeon, such as images from other imaging modalities, such as MRI images or CT scan images. In some cases, it can be desirable to label or tag items in the field of view, such as, for non-limiting example, tools or organs or regions of tissue to be removed.

The device disclosed herein provides a "smart" system for automatic maneuvering, under software control, of at least one surgical tool such as an endoscope in at least two and preferably three dimensions, where the system comprises software configured to identify an input event such as an item of interest or a movement pattern, of a portion of the system itself (such as, but not limited to, a tool), of objects within the field of view of the endoscope, of a control mechanism (such as, but not limited to, a joystick), or of a moving object outside the system (typically an operator), to analyze an input, either a movement pattern or an observed activity, and determine from the at least one input an input event, and to provide a predictable response to the input event, such that the response is appropriate to the input event, and no predetermined fixed association need be defined between the input event and the response, an output surgical procedure.

A non-limiting example of a predetermined fixed association is an arbitrary association between a particular movement of a tool and an output surgical procedure, where there is no intrinsic connection between the input event and the output surgical procedure. Non-limiting examples of arbitrary associations are: shaking a tool so that an endoscope will track that tool; clockwise circling of a tool tip in order to zoom an endoscope inward toward the tip, anti-clockwise circling of a tool tip in order to zoom the endoscope outward; or a zigzag movement in order to increase light intensity.

On the other hand, non-limiting examples of predictable responses to an input event are: zooming inward and outward during a suturing procedure to provide optimum views during the different stages of suturing, increasing light intensity if smoke is seen, providing a fluid flow across the tip of an endoscope if smoke or particulates are seen, automatically tracking the line of a dissection, or showing an image of a region where there is unexpected bleeding. Many more examples will be obvious to one skilled in the art.

Preferably, the movement patterns which identify input events comprise simple movements. For non-limiting example, movement of a scalpel smoothly downward toward an organ typically presages an incision; after recognition that the input event indicates an incision; a typical output procedure would be for the endoscope to track the scalpel. In another non-limiting example, circular movement of the tip of a needle typically indicates suturing. A typical output procedure would be to zoom the endoscope in during tying of a knot, then moving it out and tracking the needles as the needle moves to a subsequent suture. In a variant of this example, if, after a suture is completed, the needle moves so that it is no longer tending to follow the line of an incision, the surgical event would be "completion of suturing" and a typical output surgical procedure would be to zoom outward to give an overview of the surgical field, in preparation for a next surgical event. In another non-limiting example, the surgical event is fogging of the field of view, where the output procedure is starting suction to clear the field of view of smoke.

The response to the input event is an output surgical procedure selected from a group consisting of: responsively maneuvering a surgical tool, interactively activating at least one surgical tool, interactively deactivating at least one surgical tool, interactively articulating at least a portion of at least one surgical tool, displaying a message, and any combination thereof.

The message can include: information about a patient, information about at least one said tool, information about a procedure, suggestion for a future action; a warning; display of an abnormal event; and any combination thereof.

In some embodiments, the system is configured to analyze at least one of: an image as observed by an imaging means, a movement of an operator, a sound signal, a thought by an operator, a contact with a prepared surface and any combination thereof.

The indicating means providing the data for the analysis can be selected from a group consisting of: a sensor; a maneuvering mechanism, a controller, an imaging means, processing means to real-time analyze an image, typically an image of the field of view, processing means to calculate a 3D position of a surgical tool; and any combination thereof. The imaging means can comprise an imaging system configured to real-time image the field of view.

In preferred embodiments, the system can identify interactions selected from a group consisting of: between portions of tissue, between tissue and at least one tool, between at least two tools and any combination thereof.

Non-limiting examples of interactions between portions of tissue can include: a change in the distance between the edges of a cut, or a portion of tissue bulging through a gap.

Non-limiting examples of interactions between at least one tool and tissue include suturing, swabbing, dissecting, retraction, cautery and ablation.

Non-limiting examples of interactions between tools include suturing (between the thread, a needle, a forceps holding the needle and a forceps to hold an end of the thread), retraction (the distance between the retractors), and tracking of a tool by an endoscope.

It will be noted that procedures can include both tissue-tissue interactions and tissue-tool interactions (e.g., suturing).

For non-limiting example, the system can be configured to recognize that small circular movements of a tool tip indicate that a suture is being made. The system can then automatically zoom the endoscope to optimize the view of the suturing procedure, either by means of a single zoom providing a good overall view or each suture, or by means of multiple zooms, so it zooms in and out to ensure that an optimum view of the procedure is provided at all times.

In some variants, the system can interpret movements indicating the end of a suturing pattern as indicative of the operator preparing to create the next suture. In response the system can either automatically follow the suturing tool tip or automatically move the center of the field of view to the expected location of the next suture. In some variants, the system uses previously-stored information on the distance between sutures and the direction of movement of the surgeon after completion of a suture to estimate the location of the next suture. In some variants, after the second suture, the system predicts the probable location for each subsequent suture and, when each suture movement pattern ends, the system automatically moves so that the field of view is centered on the expected location of the next suture, thus obviating the need for the surgeon to command the movement.

In some embodiments, the system can identify an item of interest in the surgical field and its location and can respond to the item of interest. Items of interest can include, but are not limited to, an article entering the field of view of the lens, an article moving, a likely collision between two articles, the occurrence of bleeding, smoke, the edges of an incision moving, activation or deactivation of a tool, articulation of a tool, and any combination thereof.

Non-limiting examples of collisions between two articles are: a collision between two or more tools, and a collision between at least one tool and an organ.

Responses to items of interest can include: altering the field of view to encompass the item of interest, showing an icon or popup of the item of interest, warning the operator of the item of interest, redirecting an endoscope to focus on an item of interest, redirecting an endoscope to focus on a predicted position for an item of interest (e.g., the predicted position on an organ of a collision between a tool and the organ, thereby focusing on a likely site of a dissection), redirecting an endoscope to track an item of interest (e.g., to track a tool predicted to collide with an organ, thereby tracking a tool likely to carry out a dissection) and any combination thereof.

For non-limiting example, smoke in the operating environment can indicate ablation or cauterizing of tissue; a response can include, but is not limited to: zooming outward so as to provide an optimum view of the ablation region, zooming inward to follow an ablation as it moves deeper into tissue, following the ablation as it moves across tissue, pausing at the end of an ablation to allow time for an operator to have a substantially smoke-free view of an ablation region, changing lighting of at least a portion of the surgical field, flowing fluid within at least a portion of the surgical field, applying suction to at least a portion of the surgical field, maneuvering an endoscope, zooming an endoscope, and any combination thereof. In preferred embodiments, the output surgical procedure associated with the presence of smoke need not be fixed; it can depend on the stage of the operation, the presence of other tools, the amount of fluid already present, an operator's preferences (entered by the operator or stored from a previous surgical procedure), the availability of a needed resource, and any combination thereof. For non-limiting example, if the maximum available fluid flow or suction is already being used, then lighting can be increased or the endoscope moved to improve visibility.

In some embodiments, if smoke is detected, instead of or in addition to at least one of the above responses, a suggestion can be provided, with the suggestion being to carry out at least one of the above responses. For non-limiting example, if smoke is detected, the response can be: the endoscope is automatically zoomed out, a suggestion is provided that the lighting be increased, or both. The suggestion can be visual, using a popup or any other means known in the art, it can be aural, such as a voice message or any other means known in the art, and any combination thereof.

In some embodiments, if movement of a smoke source is detected, the endoscope, lighting, fluid flow and/or suction can track the movement of the smoke source. In some embodiments, tracking can anticipate movement of the smoke source, with the expected direction of movement determined by image analysis, data from another imaging modality, markings provided by an operator and any combination thereof.

Changing lighting can include, but is not limited to, changing the intensity of the illumination of at least a portion of the surgical field, redirecting at least one light source toward or away from at least a portion of the surgical field, activating a light source, deactivating a light source and any combination thereof.

Fluid can be flowed across at least a portion of a surgical field to remove smoke and/or debris from the region in order to maintain a clear field of view. Flowing fluid can include, but is not limited to: providing a flow of fluid across at least a portion of an endoscope, providing a flow of fluid across a region being ablated or cauterized and any combination thereof.

Similarly, suction can be used to remove smoke, debris, excess fluid and any combination thereof from at least a portion of a surgical field.

In another non-limiting example, bleeding in an operating environment typically occurs (1) during dissection or ablation, or (2) when a failure occurs, such as leakage from a suture or between sutures, a tear or other failure in a tissue, or a swab or clamp moving or accidentally releasing.

In the first case, typical responses include but are not limited to: altering the field of view to follow the dissection or ablation, zooming outward to ensure that the entire dissection or ablation remains in the field of view, zooming to provide an optimum view of the region of the dissection or ablation, starting fluid flow or suction to keep the FOV clear, increasing the intensity of lighting, and any combination thereof.

In the second case, typical responses include but are not limited to: altering the field of view to center on the region of the bleeding, showing an icon or a popup of the region of the bleeding, warning the operator of the bleeding, moving a swab to absorb bleeding, moving a retractor to stop bleeding, repositioning a swab or clamp that has slipped or released, starting fluid flow or suction to keep the FOV clear, increasing the intensity of lighting, and any combination thereof.

In another non-limiting example, touching of a tissue or organ by a tool can indicate that dissection, cauterizing or ablation is to occur. Responses can include zooming to optimize the view of the tool and the touched region so that an optimum view of the dissection is provided, moving the field of view so as to follow the dissection, cautery or ablation line and any combination thereof.

Other movement patterns include, but are not limited to, predetermined movements of a tool, introducing a tool to the surgical environment, removing a tool from the surgical environment, retraction, ligation, cauterizing, undermining, ablating tissue, incising tissue, blunt dissection, sharp dissection, removing tissue from the surgical environment, applying a clip, clamp or grasper, lavaging, swabbing, placing a swab, sponge or other absorbing medium, and introducing material such as, but not limited to, a stent, a drain, graft tissue, or an artificial replacement item into the surgical environment.

Any combination of the above movement patterns can also comprise a movement pattern.

Responses to movement patterns can include, but are not limited to, maneuvering an endoscope, zooming or otherwise changing the focus of an endoscope; moving a tool; activating or deactivating a tool; articulating a tool; and any combination thereof.

A non-limiting example of activating a tool is closing a grasper to retain a swab in position. The grasper can be closed because of (a) a predetermined gesture commanding closure of the grasper, (b) the grasper is in the correct position to hold the swab and (c) any combination thereof. Similarly, the grasper can be opened to release the swab if (a) a predetermined gesture commands opening of the grasper, (b) it is determinable that a swab is to be removed, and (c) any combination thereof.

Another non-limiting example is, if a movement pattern is recognized which indicates that the next procedure is likely to be deeper in the tissue, retractors can be moved to hold an incision further open. Similarly, a movement pattern indicative of withdrawal from a region of tissue can result in relaxation of retractors and at least partial closing of an incision.

In some embodiments, initiation of cauterizing or ablation results in initiation of means to keep the endoscope optics clear, and preferably the field of view clear. These means can include, but are not limited to, directing a flow of fluid across the optics, applying suction to remove excess fluid and/or particulates, directing a flow of fluid at a predetermined angle to the optics, such as, but not limited to, parallel to the endoscope probe, directing a flow of fluid across the region being cauterized, and any combination thereof. The fluid can be a liquid, a gas and any combination thereof.

In some embodiments, a suggestion can be provided. The suggestion can appear as an icon or popup on a display, as an aural message, such as a voice message, or as any conventional suggestion/warning means known in the art, or as any combination thereof. A suggestion can include, but is not limited to, a procedure, a recommendation, a warning, and any combination thereof.

An output surgical procedure can comprise any procedure or rule disclosed herein and any combination thereof.

A recommendation can comprise an action to be carried out (non-limiting examples: "increase intensity of illumination"; "redirect illumination onto tip of left lobe of liver"; "recommend prosthetic vein graft"; "cauterize tissue to prevent bleeding"; "ablate before suturing"); a surgical procedure, either during a current surgery (non-limiting example: "blunt dissection to remove lump") or as part of a separate surgery (non-limiting example: "hernia repair indicated"). Many more examples will be obvious to one skilled in the art.

A warning can comprise an item of immediate concern (non-limiting examples include an item of interest outside the field of view, and "possible malignancy—remove whole"), an item of future concern (non-limiting example: "check lump—possible malignancy") and any combination thereof.

In preferred embodiments, the system provides an override facility such that an undesired automatic movement can be overridden. The override can be a voice command, a movement, an intended movement or a thought. The movement or intended movement can be movement of a hand, an eye, an arm, a finger, a chest, a neck, a head, a mouth, a tongue, vocal cords (a predetermined sound), a leg, a toe, a foot or any combination thereof. An actual movement can be detected by any movement detection means, as described hereinbelow. An intended movement can be detected by means of muscular electric or magnetic patterns, as described hereinbelow, or from encephalographic patterns ("brain waves"), as described hereinbelow. Similarly an override thought can be detected by means of encephalographic patterns.

In some embodiments, the system can identify at least one unwanted input event for at least one moving element. Non-limiting examples of unwanted input events include: involuntary movement of a body part, saccadic movement of an eye, vestibulo-ocular movement of an eye, winking an eye, blinking an eye, tremor of a body part, a tic in a body part, myoclonus of a body part, dystonia, and any combination thereof.

In such embodiments, the preferred response is for the system to ignore the unwanted input event, so that the output procedure is unaffected by and substantially independent of the unwanted movement. For non-limiting example, in a system where movement of an endoscope is proportional to movement of an eye, the jerkiness of the actual eye movement, imparted both by saccadic movement and vestibule-ocular movement, will be "programmed out" so that the movement of the endoscope is smooth. Similarly, if eye movement is controlling movement of an endoscope to the right, a quick glance upward will be "programmed out"; the endoscope will not diverge from the direct path to the right.

In another non-limiting example, movement of two retractors is controlled by movement of two arms. During a retraction to further open an incision, the operator suffers a muscular twitch that jerks an arm upward. The jerk is ignored so that the retractors move apart smoothly.

In preferred embodiments, control of at least one tools and control of maneuvering of the endoscope does not require physical contact between the surgeon and either the tool or the endoscope. Control of at least one tool and/or maneuvering of an endoscope can be via at least one predetermined input command associated with a predetermined output procedure, or via detection, by the system, of an input event, with the output surgical procedure dependent on at least one of the input event and other information accessible to the system.

The system of the present invention can be used in a conventional manner, with the operator and other members of the operating team in the same room as the patient during the operation, or the system of the present invention can be used for remote surgery, with the operator controlling the laparoscope and the tools from a location remote from the patient. In addition, in preferred embodiments, control of maneuvering of at least one tool or of the endoscope can be done without need for an operator, during an operation, to remove a place his hand in contact with the device.

Movement patterns can be identified from movements sensed by sensors tracking movement of some portion of an operator, movements determined from an endoscope image, movements sensed by sensors attached to tools, movements measured directly by the maneuvering system, movements or intended movements determinable from brain wave or other encephalographic patterns, electrical or magnetic patterns indicative of muscular movement, and any combination thereof.

Pattern recognition enables the system to predict movements of the operator and to provide an appropriate response of the endoscope to the predicted movements.

In some embodiments of the system, the system is programmed such that it can "learn" new movement patterns and store the new patterns in a database of movement patterns. In some variants of this embodiment, a database further comprises at least one set of movement patterns linkable to a surgeon so that, either from the surgeon entering an identifier at the beginning of a procedure, or by recognizing a surgeon's typical movement patterns, the system will interpret movement patterns on the basis of the typical movement patterns for the identified individual, and will respond to these movement patterns based on the movement pattern anticipatable for this individual.

The system can be configured to alter a displayed image, to move an endoscope, to control the position of a tool, to control articulation of a tool and any combination thereof.

It should be noted that maneuvering of the laparoscope display can be accomplished by physical maneuvering (physically moving some portion of the laparoscope or the imaging optics), by virtual maneuvering (changing the viewed image by means of computer algorithms that alter the portion of the field of view which is displayed), or by any combination thereof.

In some embodiments, control of maneuvering is via a body-mounted user interface which comprises at least one sensor, the sensor configured to sense at least one parameter associated with body motion, with the body motion directing maneuvering of a displayed image, of the endoscope, of a tool, and any combination thereof.

The sensor or sensors can be placed in conjunction with a body portion of the surgeon, or can be placed so that a body portion of the surgeon is within range of the sensor.

A sensor can be, for non-limiting example, an ultrasound sensor, an IR sensor, a heat sensor, a pressure sensor, a current sensor, an accelerometer, a tilt sensor, a movement sensor, a gyroscope, an inertial sensor, a goniometer, a magnetometer, a camera, a strain sensor, an encephalographic sensor, an electrical sensor, a magnetic sensor, and any combination thereof.

The sensors are preferably MEMS devices.

The sensors are preferably in wireless communication with the data processor controlling maneuvering of the display view.

As a non-limiting example of an embodiment, a band encircling the surgeon's lower arm can comprise accelerometers, thereby sensing movement of arm.

In some embodiments, the sensor or sensors can comprise viewing means, such as, but not limited to a camera, an IR sensor, an ultrasound sensor, a sound sensor, an RF sensor, a heat sensor, an electrical sensor, a magnetic sensor, and any combination thereof. In such sensors, the viewing means senses either movement of the body part or patterns associated with movement of the body part. The detectable movement can include speech, which can be detected by a sound sensor.

The body part can include, but is not limited to, at least a portion of a member of a group comprising a finger, a hand, an arm, a toe, a foot, a leg, the chest, the abdomen, the torso, the neck, a head, an eye, the mouth, the brain, and any combination thereof.

In some embodiments, the intended movement can be detected encephalographically, via at least one sensor, preferably on the head, configured to determine, from at least one encephalographic pattern, at least one parameter associated with at least one of position, velocity and acceleration of said at least one portion of said human body. The intended movement can include speech; in this case, the encephalographic pattern can be a pattern indicating activity of the brain speech centers.

In some embodiments, the detectable encephalographic pattern can include a pattern indicative of alarm or fright. Such a pattern can be used, for non-limiting example, as an override signal.

In some embodiments, at least one electric or magnetic sensor detects electrical and/or magnetic patterns associated with movement of at least one muscle. From these electrical and/or magnetic patterns, the intended movement of the muscle and, therefore, the intended movement of the body part can be determined and translated into a maneuver of the surgical tool. The sensor can be remote from the body part intended to be moved; for example, electrical patterns measured for one or more chest muscles can be used to determine intended movement of an arm and, thence, the desired movement of a surgical tool.

Any combination of the above sensors can be used to maneuver the surgical tool. The tool maneuver can be a maneuver generated by the system in response to a detected movement pattern, a maneuver directly commanded by a user and any combination thereof.

There can be one viewing means per tool, one viewing means can view a plurality of tools, a plurality of viewing means can view one tool, one viewing means can view a plurality of tools, a plurality of viewing means can view a plurality of tools, and any combination thereof.

For non-limiting example, to move the center of the display view towards the right of the display, the surgeon gestures rightward. An upward gestures zooms the display view outward, shrinking objects in view; a gesture away from the body moves the center of the display view towards the top of the display, and any combination thereof. Other gestures can control returning to a previous view or selecting an object, such as a tool, to be tracked, where following an object means keeping the selected object at the center of the field of view and, if possible, keeping constant its apparent size in the display view.

In another non-limiting example of an embodied gesture, shaking a tool tip selects the tool as the object to be tracked. This informs the system that the left tool is to be tracked; it is to be kept in the center of the field of view. A second shake of the tool tip stops tracking. Shaking another tool transfers tracking to the shaken tool.

Another non-limiting example of an embodied gesture is opening and closing the hand to open and close a grasper or bringing the thumb towards a finger to close a grasper and separating the thumb and a finger to open a grasper.

The gesture embodiments described hereinabove can be used in any combination.

Gestures can be combined with, for example, use of a touchscreen or prepared surface. In such embodiments, the surgeon can touch the image on a screen or other prepared surface to select an object, then execute a gesture to indicate what the object is to do. For non-limiting example, in such an embodiment, in order to retract tissue seen near the top of the screen with a grasper seen near the right side of the screen, the surgeon touches the image of the grasper to select the grasper and gestures leftward and away from himself. When the tip of the grasper is above the tissue to be retracted, the surgeon gestures downward and opens his hand, thereby opening the grasper and moving its tip down towards the tissue. When one grasper jaw is above the tissue and one below, a gesture away from himself moves the grasper jaws around the tissue and closure of the hand closes the grasper, grasping the tissue. Another gesture then retracts the tissue. The surgeon can then touch the image of the grasper again, to stop tracking of the grasper, which fixes the grasper in position.

In a variant of this embodiment, when the grasper is in position, instead of closing his hand, the surgeon touches the touchscreen and the grasper automatically closes on the tissue and remains closed. The surgeon can then move a hand, as described above, to reposition the grasper.

In a further variant of this embodiment, when the system senses that the grasper has ceased movement, it automatically closes the grasper and holds it in a closed position. After closure of the grasper, further movement of the surgeon will reposition the grasper.

Other embodiments of gestures and of means of identifying tools will be obvious to one skilled in the art.

Non-limiting examples of sensor locations include the hand, the wrist, the forearm, the elbow, the shoulder, the neck, the chest, and the face. The sensors can comprise a portion of a glove, a band, a harness or a mask or be mounted on or in a glove, a band, a harness or a mask.

A glove can be fingerless, or can have one or more fingers. It can be hand-length, wrist-length, elbow length, can extend partway up the arm, or can extend all the way up the arm. It can have any combination of length and number of fingers. One or two gloves can be worn; they can comprise any combination of the above features.

Non-limiting examples of bands include elastic bands and non-elastic bands; bands are preferably flexible in order to conform to the surface of the body part, but portions can be rigid. The band can be continuous or can comprise at least one break. Bands can comprise ties, buckles, or any other closure means or size-adjustment means known in the art. They can be fixed-length or variable-length. The band can be of any desired width, up to one that covers the entire arm, or the arm and at least part of the hand. There can therefore be overlap between what is considered a "glove" and what is considered an "arm-covering band".

Bands can comprise armbands, hand bands, face bands and chest bands. Chest-movement sensors can be comprised in a harness, which can be elastic or non-elastic and which can stretch to fit over the head without need for additional closures, can comprise one or more closures, can comprise one or more length-adjustment mechanisms, and any combination thereof. A closures and a length-adjustment mechanism can be a tie, a buckle, a snap, a button, any other closure mechanism known in the art and any combination thereof.

In some embodiments, the motion of a body part can be translated into movement of a tool such that the movement of the tool is proportional to the movement of the body part, with larger movements of the body part resulting in proportionally larger movements of the tool. In preferred embodiments of this type, the constant of proportionality is much less than 1, so that relatively large movements of the body part result in small movements of the tool.

In some embodiments of this type, the motion of the body part is be translated into movement of a tool such that the movement of the tool is substantially identical to the movement of the body part.

In some embodiments of this type, the motion of the body part results in a fixed movement of a tool. For non-limiting example, an opening movement of a hand, whether large or small, causes a grasper to open fully.

The movement of an endoscope or other surgical tool can be parallel to the X axis; parallel to the Y axis; parallel to the Z-axis; rotation around an axis parallel to the X axis; rotation around an axis parallel to the Y axis; rotation around an axis parallel to the Z axis; and any combination thereof.

In embodiments of the system wherein movement of a surgical tool is controlled by movement of a body part, whether sensed as movement of the body part or sensed as movement of a surgical tool, movement of the surgical tool need not be in the same direction as the movement of the body part. For example, a movement left can translate into movement upward of the surgical tool, rather than moving the body part upward to move the surgical tool upward. The direction of movement of the surgical tool can be any of: movement of the body part in a direction parallel to the X axis translates to movement of the surgical tool in a direction parallel to the X axis, movement of the body part in a direction parallel to the X axis translates to movement of the surgical tool in a direction parallel to the Y axis, movement of the body part in a direction parallel to the X axis translates to movement of the surgical tool in a direction parallel to the Z axis, movement of the body part in a direction parallel to the Y axis translates to movement of the surgical tool in a direction parallel to the X axis, movement of the body part in a direction parallel to the Y axis translates to movement of the surgical tool in a direction parallel to the Y axis, movement of the body part in a direction parallel to the Y axis translates to movement of the surgical tool in a direction parallel to the Z axis, movement of the body part in a direction parallel to the Z axis translates to movement of the surgical tool in a direction parallel to the X axis, movement of the body part in a direction parallel to the Z axis translates to movement of the surgical tool in a direction parallel to the Y axis, movement of the body part in a direction parallel to the Z axis translates to movement of the surgical tool in a direction parallel to the Z axis, rotation of the body part about an axis parallel to the X axis translates to rotation of the surgical tool about an axis parallel to the X axis, rotation of the body part about an axis parallel to the X axis translates to rotation of the surgical tool about an axis parallel to the Y axis, rotation of the body part about an axis parallel to the X axis translates to rotation of the surgical tool about an axis parallel to the Z axis, rotation of the body part about an axis parallel to the Y axis translates to rotation of the surgical tool about an axis parallel to the X axis, rotation of the body part about an axis parallel to the Y axis translates to rotation of the surgical tool about an axis parallel to the Y axis, rotation of the body part about an axis parallel to the Y axis translates to rotation of the surgical tool about an axis parallel to the Z axis, rotation of the body part about an axis parallel to the Z axis translates to rotation of the surgical tool about an axis parallel to the X axis, rotation of the body part about an axis parallel to the Z axis translates to rotation of the surgical tool about an axis parallel to the Y axis, rotation of the body part about an axis parallel to the Z axis translates to rotation of the surgical tool about an axis parallel to the Z axis, and any combination thereof.

In some embodiments, linear movement of the body part, whether sensed as movement of the body part or sensed as movement of a surgical tool, is translated to rotational movements of the endoscope or other surgical tool. For example: movement of the body part in a direction parallel to the X axis translates to rotation of the surgical tool about an axis parallel to the X axis, movement of the body part in a direction parallel to the X axis translates to rotation of the surgical tool about an axis parallel to the Y axis, movement of the body part in a direction parallel to the X axis translates to rotation of the surgical tool about an axis parallel to the Z axis, movement of the body part in a direction parallel to the Y axis translates to rotation of the surgical tool about an axis parallel to the X axis, movement of the body part in a direction parallel to the Y axis translates to rotation of the surgical tool about an axis parallel to the Y axis, movement of the body part in a direction parallel to the Y axis translates to rotation of the surgical tool about an axis parallel to the Z axis, movement of the body part in a direction parallel to the Z axis translates to rotation of the surgical tool about an axis parallel to the X axis, movement of the body part in a direction parallel to the Z axis translates to rotation of the surgical tool about an axis parallel to the Y axis, movement of the body part in a direction parallel to the Z axis translates to rotation of the surgical tool about an axis parallel to the Z axis and any combination thereof.

In some embodiments, rotational movement of the body part, whether sensed as movement of the body part or sensed as movement of a surgical tool, is translated to linear movements of the surgical tool. For example: rotation of the body part about an axis parallel to the X axis translates to movement of the surgical tool in a direction parallel to the X axis, rotation of the body part about an axis parallel to the X axis translates to movement of the surgical tool in a direction parallel to the Y axis, rotation of the body part about an axis parallel to the X axis translates to movement of the surgical tool in a direction parallel to the Z axis, rotation of the body part about an axis parallel to the Z axis translates to movement of the surgical tool in a direction parallel to the X axis, rotation of the body part about an axis parallel to the Z axis translates to movement of the surgical tool in a direction parallel to the Y axis, rotation of the body part about an axis parallel to the Z axis translates to movement of the surgical tool in a direction parallel to the Z axis and any combination thereof.

In some embodiments, movement of the body part, whether sensed as movement of the body part or sensed as movement of a surgical tool, is translated into movement of a portion of a tool. For non-limiting example, an opening or closing gesture of a hand or fingers to open and close a grasper, a pair of scissors or any other openable tool, bending a hand or finger to change the articulation of an endoscope or other articulable tool, making a first to freeze at least a portion of a tool in position, and any combination thereof.

Any combination of the above translations and rotations can be used in an embodiment.

In some embodiments, a predetermined output surgical procedure is configured to determine a member of a group consisting of: an allowed movement of a first surgical tool, a restricted movement of a first surgical tool and any combination thereof from historical movements of the first surgical tool according with historical movement patterns of at least one second surgical tool in at least one previous surgery. Thus, according to these embodiments, the predetermined output surgical procedure comprises a communicable database storing each 3D spatial position of the first surgical tool according with at least two 3D spatial positions of at least one second surgical tool, such that each movement pattern of the at least one second surgical tool and each 3D position of the first surgical tool according with the same is stored; the predetermined output surgical procedure is configured to determine a member of a group consisting of: an allowed movement of the first surgical tool, a restricted movement of the first surgical tool and any combination thereof from the stored movement patterns of the at least one second surgical tool and the stored movements of the first surgical tool, such that an allowed movement of the first surgical tool is a movement in which the first surgical tool is located substantially in at least one of the first surgical tool 3D spatial positions according with at least one 3D second surgical tool movement pattern, and a restricted movement is a movement in which the location of the first surgical tool is substantially different from the n 3D first surgical tool spatial positions according with the n second surgical tool movement patterns.

An example of a first surgical tool is an endoscope; in one variant of this example, the endoscope tracks a second surgical tool.

Another use for the system of the present invention can be for study or training. By use of a plurality of display screens, a number of students can observe the operation in real time; the students can be in locations remote from both the patient and the operator. The display view can be marked to assist the students in understanding what is present in the display view. Marking can be done by persons other than the operator; in some embodiments, the operator need not be aware of marks applied to the display view for study or teaching purposes.

In some embodiments, a system and method is provided for providing augmented reality images of a field of view, where the augmentation can be images provided by another imaging modality, stored images or other stored data, information entered by a user, and any combination thereof. The field of view can be the field of view of an endoscope or laparoscope, or the field of view of a surgical tool.

The system further comprises a predetermined set of rules to control movement of the surgical tool. As described hereinbelow, the rules, among other functions, ensure that a surgical tool can be moved without undesired contact with another surgical tool or with a portion of the body. The predetermined set of rules is configured to take into consideration all the possible factors which may be important during the surgical procedure. The predetermined set of rules can comprise any combination of the following rules:

a. a route rule;
b. an environment rule;
c. an operator input rule;
d. a proximity rule;
e. a collision prevention rule;
f. a history based rule;
g. a tool-dependent allowed and restricted movement rule.
h. a most used tool rule;
i. a right tool rule;
j. a left tool rule;
k. a field of view rule;
l. a no fly zone rule;
m. an operator input rule;
n. a preferred volume zone rule;
o. a preferred tool rule;
p. a movement detection rule, Thus, for example, the collision prevention rule defines a minimum distance below which two or more tools or one or more tools and one or more organs should not be brought together (i.e., there is minimum distance between two or more tools that should be maintained). If the movement of one tool will cause it to come dangerously close to another tool (i.e., the distance between them, after the movement, is smaller than the minimum distance defined by the collision prevention rule), the controller either alerts the user that the movement is a restricted movement or does not permit the movement.

It should be emphasized that all of the above (and the following disclosure) is enabled by constantly monitoring the surgical environment, and identifying and locating the 3D spatial location of each element/tool in the surgical environment.

The identification is provided by conventional means known to anyone skilled in the art (e.g., image processing, optical means, etc.).

The following provides explanations for each of the above mentioned rules and their functions:

According to some embodiments, the route rule comprises a predefined route in which the at least one surgical tool is configured to move within the surgical environment; an allowed movement is a movement in which the at least one surgical tool is located within the borders of the predefined route, and a restricted movement is a movement in which the at least one surgical tool is located out of the borders of the predefined route. Thus, according to this embodiment, the route rule comprises a communicable database storing at least one predefined route in which the at least one surgical tool is configured to move within the surgical environment; the predefined route comprises n 3D spatial positions of the at least one surgical tool in the route; n is an integer greater than or equal to 2; an allowed movement is a movement in which the at least one surgical tool is located substantially in at least one of the n 3D spatial positions of the predefined route, and a restricted movement is a movement in which the location of the at least one surgical tool is substantially different from the n 3D spatial positions of the predefined route.

In other words, according to the route rule, each of the surgical tool's courses (and path in any surgical procedure) is stored in a communicable database. An allowed movement is defined as a movement in which the at least one surgical tool is located substantially in at least one of the stored routes; and a restricted movement is a movement in which the at least one surgical tool is in a substantially different location than any location in any stored route.

According to some embodiments, the environmental rule is configured to determine an allowed movement and a restricted movement according to the hazards or obstacles which occur in the surgical environment, as received from an endoscope or other sensing means. Thus, according to this embodiment, the environmental rule comprises a communicable database; the communicable database is configured to receive real-time images of the surgical environment and is configured to perform real-time image processing of the same and to determine the 3D spatial position of hazards or obstacles in the surgical environment; the environmental rule is configured to determine an allowed movement and a restricted movement according to hazards or obstacles in the surgical environment, such that a restricted movement is a movement in which at least one surgical tool is located substantially in at least one of the 3D spatial positions, and an allowed movement is a movement in which the location of at least one surgical tool is substantially different from the 3D spatial positions.

In other words, according to the environment rule, each element in the surgical environment is identified so as to establish which is a hazard or obstacle (and a path in any surgical procedure) and each hazard and obstacle (and path) is stored in a communicable database. A restricted movement is defined as a movement in which the at least one surgical tool is located substantially in the same location as that of the hazards or obstacles; and an allowed movement is a movement in which the location of the at least one surgical tool is substantially different from that of all of the hazards or obstacles.

According to other embodiments, hazards and obstacles in the surgical environment are selected from a group consisting of tissues, surgical tools, organs, endoscopes and any combination thereof.

According to some embodiments, the operator input rule is configured to receive an input from the operator of the system regarding at least one of an allowed movement of the at least one surgical tool and a restricted movement of the at least one surgical tool. Thus, according to this embodiment, the operator input rule comprises a communicable database; the communicable database is configured to receive an input from the operator of the system regarding at least one allowed movement and at least one restricted movement of the at least one surgical tool. In other words, the operator input rule receives instructions from the operator as to what can be regarded as an allowed movement and what is a restricted movement. According to some embodiments, the input comprises n 3D spatial positions; n is an integer greater than or equal to 2; wherein at least one of which is defined as an allowed location and at least one of which is defined as a restricted location, such that an allowed movement is a movement in which the at least one surgical tool is located substantially in at least one of the n 3D allowed spatial positions, and a restricted movement is a movement in which the location of the at least one surgical tool is substantially different from the n 3D allowed spatial positions.

According to some embodiments, the input comprises at least one rule according to which at least one of an allowed movement and a restricted movement of the at least one surgical tool is determined, such that the spatial position of the at least one surgical tool is controlled by the controller according to the at least one allowed movement and the at least one restricted movement.

According to other embodiments, the operator input rule can convert an allowed movement to a restricted movement and a restricted movement to an allowed movement.

According to some embodiments, the proximity rule is configured to define a predetermined distance between at least one surgical tool and at least one article; an allowed movement is a movement which are within the range or out of the range of the predetermined distance, and a restricted movement is a movement which is out of the range or within the range of the predetermined distance; an allowed movement and a restricted movement are defined according to different ranges. Thus, according to this embodiment, the proximity rule is configured to define a predetermined distance between at least two surgical tools. In a preferred embodiment, an allowed movement is a movement which is within the range of the predetermined distance, while a restricted movement is a movement which is out of the range of the predetermined distance. In another preferred embodiment, an allowed movement is a movement which is out of the range of the predetermined distance, while a restricted movement is within the range of the predetermined distance It should be pointed out that the above mentioned distance can be selected from the following:
 (a) the distance between the tip of the first tool and the tip of the second tool;
 (b) the distance between a portion of the body of the first tool and the tip of the second tool;
 (c) the distance between a portion of the body of the first tool and a portion of the body of the second tool;
 (d) the distance between the tip of the first tool and a portion of the body of the second tool; and any combination thereof.

According to some embodiments, the proximity rule is configured to define at least one predetermined angle between at least three articles; an allowed movement is a movement which is within the range or out of the range of the predetermined angle, and a restricted movement is a movement which is out of the range or within the range of the predetermined angle.

According to some embodiments, the collision prevention rule is configured to define a predetermined distance between the at least one surgical tool and an anatomical element within the surgical environment; an allowed movement is a movement which is in a range that is larger than the predetermined distance, and a restricted movement is a movement which is in a range that is smaller than the predetermined distance.

According to some embodiments, the anatomical element is selected from a group consisting of tissue, organ, blood vessel, nerve, bone, muscle, ligament, abnormality and any combination thereof.

According to some embodiments, the surgical tool is an endoscope configured to provide real-time images of a surgical environment.

According to some embodiments, the right tool rule is configured to determine the allowed movement of the endoscope according to the movement of a surgical tool in a specified position in relation to the endoscope. According to this rule, the tool which is defined as the right tool is constantly tracked by the endoscope. According to preferred embodiments, the right tool is defined as the tool positioned to the right of the endoscope; according to other embodiments, any tool can be defined as the right tool. An allowed movement, according to the right tool rule, is a movement in which the endoscope field of view is moved to a location substantially the same as the location of the right tool, thereby tracking the right tool. A restricted movement, according to the right tool rule, is a movement in which the endoscope field of view is moved to a location substantially different from the location of the right tool.

According to some embodiments, the left tool rule is configured to determine the allowed movement of the endoscope according to the movement of a surgical tool in a specified position in relation to the endoscope. According to this rule, the tool which is defined as the left tool is constantly tracked by the endoscope. According to preferred embodiments, the left tool is defined as the tool positioned to the left of the endoscope; according to other embodiments, any tool can be defined as the left tool. An allowed movement, according to the left tool rule, is a movement in which the endo scope field of view is moved to a location substantially the same as the location of the left tool. A restricted movement, according to the left tool rule, is a movement in which the endo scope field of view is moved to a location substantially different from the location of the left tool.

According to some embodiments, the field of view rule is configured to define a field of view and maintain that field of view. The field of view rule is defined such that if the endoscope is configured to track a predetermined set of tools in a desired field of view, when one of those tools is no longer in the field of view, the rule instructs the endoscope to zoom out so as to reintroduce the tool into the field of view. Thus, according to some embodiments, the field of view rule comprises a communicable database comprising n 3D spatial positions; n is an integer greater than or equal to 2; the combination of all of the n 3D spatial positions provides a predetermined field of view; the field of view rule is configured to determine the allowed movement of the endoscope within the n 3D spatial positions so as to maintain a constant field of view, such that an allowed movement is a movement in which the endoscope is located substantially in at least one of the n 3D spatial positions, and a restricted movement is a movement in which the location of the endoscope is substantially different from the n 3D spatial positions.

Thus, according to some embodiments of the field of view rule, the field of view rule comprises a communicable database comprising n 3D spatial positions; n is an integer greater than or equal to 2; the combination of all of the n 3D spatial positions provides a predetermined field of view. The field of view rule further comprises a communicable database of m tools and the 3D spatial locations of the same, where m is an integer greater than or equal to 1 and where a tool can be a surgical tool, an anatomical element and any combination thereof. The combination of all of the n 3D spatial positions provides a predetermined field of view. The field of view rule is configured to determine an allowed movement of the endoscope such that the m 3D spatial positions of the tools comprise at least one of the n 3D spatial positions of the field of view, and a restricted movement is a movement in which the 3D spatial position of at least one tool is substantially different from the n 3D spatial positions of the field of view.

According to some embodiments, the preferred volume zone rule comprises a communicable database comprising n 3D spatial positions; n is an integer greater than or equal to 2; the n 3D spatial positions provides the preferred volume zone; the preferred volume zone rule is configured to determine the allowed movement of the surgical tool within the n 3D spatial positions and restricted movement of the endoscope outside the n 3D spatial positions, such that an allowed movement is a movement in which the surgical tool is located substantially in at least one of the n 3D spatial positions, and a restricted movement is a movement in which the location of at least a portion of a surgical tool is substantially different from the n 3D spatial positions. In other words, the preferred volume zone rule defines a volume of interest (a desired volume of interest), such that an allowed movement, according to the preferred volume zone rule, is a movement in which the portion of the surgical tool (such as an endoscope) is moved to a location within the defined preferred volume. A restricted movement, according to the preferred volume zone rule, is a movement in which the portion of the surgical tool (such as an endoscope) is moved to a location outside the defined preferred volume.

According to some embodiments, the preferred tool rule comprises a communicable database, the database stores a preferred tool; the preferred tool rule is configured to determine the allowed movement of the endoscope according to the movement of the preferred tool. In other words, the preferred tool rule defines a preferred tool (i.e., a tool of interest) that the user of the system wishes to track. An allowed movement, according to the preferred tool rule, is a movement in which the field of view of the endoscope is moved to a location substantially the same as the location of the preferred tool. A restricted movement is a movement in which the field of view of the endoscope is moved to a location substantially different from the location of the preferred tool. Thus, according to the preferred tool rule the endoscope constantly tracks the preferred tool, such that the preferred tool is constantly within the field of view of the endoscope. It should be noted that the user can define the preferred tool rule to constantly track the tip of the preferred tool or, alternatively, the user may define the preferred tool rule to constantly track at least a portion of the body or any predetermined location on the preferred tool.

According to some embodiments, the no fly zone rule is configured to define a restricted zone into which no tool (or alternatively no predefined tool) is permitted to enter. Thus, according to this embodiment, the no fly zone rule comprises a communicable database comprising n 3D spatial positions; n is an integer greater than or equal to 2; the n 3D spatial positions define a predetermined volume within the surgical environment; the no fly zone rule is configured to determine a restricted movement if the movement is within the no fly zone and an allowed movement if the movement is outside the no fly zone, such that a restricted movement is a movement in which the at least one surgical tool is located substantially in at least one of the n 3D spatial positions, and an allowed movement is a movement in which the location of the at least one surgical tool is substantially different from the n 3D spatial positions.

According to some embodiments, the most used tool function is configured to define (either real-time, at some time during the procedure or prior to the procedure) which tool is the most used tool (i.e., the tool which is moved the most during the procedure) and to instruct the maneuvering subsystem to constantly position the endoscope to track the movement of this tool. Thus, according to this embodiment, the most used tool rule comprises a communicable database counting the number of movements of each of the surgical tools; the most used tool rule is configured to constantly position the endoscope to track the movement of the surgical tool with the largest number of movements. In some embodiments of the most used tool rule, the communicable database measures the amount of movement of each of the surgical tools; in these embodiments, the most used tool rule is configured to constantly position the endoscope to track the movement of the surgical tool with the largest amount of movement.

According to some embodiments, the system is configured to alert the physician of a restricted movement of at least one surgical tool. The alert can be audio signaling, voice signaling, light signaling, flashing signaling, a message on a display and any combination thereof.

According to some embodiments, an allowed movement is one permitted by the controller and a restricted movement is one denied by the controller.

According to some embodiments, the history-based rule is configured to determine an allowed movement and a restricted movement according to at least one historical movement of at least one surgical tool in at least one previous surgery. Thus, according to some embodiments, the history-based rule comprises a communicable database storing each 3D spatial position of each of the surgical tools, such that each movement of each surgical tool is stored; the history-based rule is configured to determine at least one of an allowed movement and a restricted movement according to at least one historical movement of the at least one surgical tool, such that an allowed movement is a movement in which the at least one surgical tool is located substantially in at least one of the 3D spatial positions, and a restricted movement is a movement in which the location of the at least one surgical tool is substantially different from the n 3D spatial positions.

According to some embodiments, the tool-dependent allowed and restricted movement rule is configured to determine at least one of an allowed movement and a restricted movement according to at least one predetermined characteristic of at least one surgical tool, where the at least one predetermined characteristic of the surgical tool is selected from a group consisting of: physical dimensions, structure, weight, sharpness, and any combination thereof. Thus, according to this embodiment, the tool-dependent allowed and restricted movement rule comprises a communicable database; the communicable database is configured to store at least one predetermined characteristic of at least one of the surgical tools; the tool-dependent allowed and restricted movement rule is configured to determine at least one of an allowed movement and a restricted movement according to the predetermined characteristic(s) of the surgical tool.

According to some embodiments, the user can define at least one property of the surgical tool he wishes the endoscope to track. Typically, the property is a predetermined characteristic of the tool, as defined above. Thus, according to the tool-dependent allowed and restricted movement rule, the endoscope constantly tracks the surgical tool having the at least one property defined by the user.

According to some embodiments of the present invention, the movement detection rule comprises a communicable database comprising the real-time 3D spatial positions of each surgical tool; the movement detection rule is configured to detect movement of at least one surgical tool. When a change in the 3D spatial position of a surgical tool is received, an allowed movement is a movement in which the endoscope is re-directed to focus on the moving surgical tool.

According to some embodiments, the at least one location estimating means is at least one endoscope configured to acquire real-time images of a surgical environment within the human body in order to estimate the location of at least one surgical tool.

According to some embodiments, the location estimating means comprises at least one selected from a group consisting of: optical imaging means, radio frequency transmitting and receiving means, at least one mark on at least one surgical tool and any combination thereof.

According to some embodiments, the at least one location estimating means is an interface subsystem between a surgeon and at least one surgical tool, the interface subsystem comprising (a) at least one array comprising N regular light sources or N pattern light sources, where N is a positive integer; (b) at least one array comprising M cameras, where M is a positive integer; (c) at least one optional optical marker and a means for attaching an optical marker to at least one surgical tool; and (d) a computerized algorithm operable via the controller, the computerized algorithm configured to record images received by each camera of each of the M cameras and to calculate therefrom the position of each of the tools, and further configured to provide automatically the results of the calculation to the human operator of the interface.

The optical marker can be a mark applied directly to a tool, a label attachable to a tool and any combination thereof.

In some embodiments of the system, the speed of movement of at least a portion of at least one surgical tool is variable, with the speed controllable by an operator. In these embodiments, the system provides a warning if this speed is above a predetermined maximum. Examples of the method of warning include, but are not limited to, a constant volume tone, a constant pitch tone, a varying volume tone, a varying pitch tone, a vocal signal, a constant color visual signal, a constant brightness visual signal, a varying color visual signal, a varying brightness visual signal, a signal visible on at least some part of the endoscope image, a signal visible on at least some portion of the patient, a signal visible in at least some portion of the surroundings of the patient, a vibration in the control unit, a temperature change in the control unit, and any combination of the above.

According to some embodiments of the present invention, the velocity of the surgical tool's movement will be automatically adjusted as a function of the distance of the tool tip, or another predetermined part of a tool, from the organ/tissue. For non-limiting example, the closer the tip of an endoscope is to an organ, the slower the endoscope moves, thereby, on the one hand, helping ensure that the endoscope tip stops in a desired position and, on the other hand, reducing the probability that the endoscope will contact the organ/tissue, either through overshoot or through a miscalculation such as could occur from drift in the system.

In some embodiments, the display comprises augmented reality elements.

In some embodiments, the surgeon can specify at least one virtual mark, each virtual mark identifying a point in the surgical field. A point can indicate an organ or tissue, be a location on an organ or tissue, be a location within the body not on an organ or tissue, indicate a tool or other object (such as a swab) introduced by the surgeon, or be a location (such as a tool tip) on a tool or other object. A virtual mark is stored in a database and can be displayed to a user in conjunction with the point in the surgical field it identifies.

Sets of points, such as but not limited to a set of points forming the outline of an object or the surface of an object can also be virtually marked. A non-limiting example of an outline would be a line indicating the approximate extent of a tumor.

Marking can be by means of touching a point on a touchscreen or other prepared surface, touching the position of a point in a 3D display, touching a symbol representing the object on a touchscreen or prepared surface, directing an indicator to the point by means of gestures or predetermined sounds, any other means known in the art of specifying a desired point, and any combination thereof.

After marking, a point can be labeled to identify the type of object marked; the point is then indicated in the image by a predetermined virtual marker. The virtual marker can comprise any means of labeling images known in the art. Non-limiting examples of virtual markers include a predetermined geometrical shape, a predetermined word, a line encircling the image of a selected object, highlighting of the selected object (placing a patch of predetermined color or predetermined texture), and any combination thereof. Color-coding, with different colors indicating different types of virtual marker, can be used, either alone or in combination with any of the virtual markers described above.

In some embodiments, a virtual marker can indicate a selectable display view. In such embodiments, selection of a marker automatically alters a display view to the view specified by the marker. Such selectable display view markers can comprise, for non-limiting example, an outline of the selectable view, a point at the center of the selectable view, a patch or different color or texture covering the selectable view, a popup of the selectable view, a thumbnail of the selectable view and any combination thereof.

In some embodiments, portions of the image are enhanced, typically in order to be seen or identified more easily. Objects which can be enhanced include, but are not limited to, blood vessels, nerves, organs, ligaments, bones, tumors or other abnormalities and any combination thereof.

Enhancement can include, but is not limited to, increasing brightness, altering color, applying color or texture patches, outlining and any combination thereof.

Markers can comprise a distance or angle measurement. For non-limiting example, the user can select two points within the display field and instruct the system to measure the distance between the points. A marker then indicates the two points and the distance between them. Similarly, for non-limiting example, selection of three points instructs the system to measure the angle formed by the three points and to provide a marker showing the points and the angle they form. Any distance or angle measurement known in the art, such as, but not limited to, those typically found in Computer Aided Design (CAD) systems can be implemented in the system of the present invention. Distance and angle measurements are 3D measurements. The distance marker will typically be labeled with the total distance between the start and end points. In some embodiments, the distance marker can give the distance between the end points as a triple of values, typically the three distances (x, y, z) of a Euclidean coordinate system. Other typical coordinate systems include, but are not limited to, cylindrical coordinate systems (r, θ, z) and spherical coordinate systems (r, θ, φ)).

In some embodiments, the orientation of the display remains fixed relative to the orientation of the surgical field, so that a given direction in a display corresponds to a given direction within the surgical field, with the correlation remaining unchanged throughout the procedure. For non-limiting example, the top of a display can indicate the position in the surgical field closest to the head of the patient.

In some embodiments, orientation marking is provided. The orientation marker indicates a direction fixed relative to the surgical field, the region of interest. Therefore, the surgeon can remain aware of the orientation of a display view relative to the surgical field, whatever the relative orientations of the surgical field and the display view.

In preferred embodiments, the orientation marker remains within a fixed region in the display view. A non-limiting example of an orientation marker is axes of a 3D coordinate system, with the axes labeled so that the identity of each axis is discernable at a glance. The axes are in a corner of the display view and rotate as the orientation of the display view changes.

Another embodiment of an orientation marker comprises an arrow with a fixed center, the direction of the arrow indicating a fixed (3D) direction in space. The point of the arrow will rotate around the center as the display view changes, while the color or texture of the arrow indicates whether the fixed direction is above or below the plane of the display image and the length of the arrow indicates the angle between the fixed direction and the plane of the display view.

Any orientation marker known in the art can be used.

In some embodiments, the display image combines the laparoscope image with an image from at least one other imaging modality. The other imaging modality can be any imaging modality known in the art, for non-limiting example, CT, MRI, PET, ultrasound, IR imaging, heat imaging, a still camera, a video camera, image-generation software, image-manipulation software, display of stored images, and any combination thereof. In preferred embodiments, if more than one imaging modality is present, images from all of the modalities are registered so that like portions correspond with each other and therefor appear to be viewed from the same distance and angle. For non-limiting example, the boundaries of the liver from an MRI scan would be substantially the same as the boundaries of the liver from the laparoscope image.

An image from a second imaging modality can be a 2D image, a 3D image and any combination thereof.

An image from another imaging modality can be a real-time image or it can be a stored image. For non-limiting example, the interior of the abdomen can be simultaneously imaged by ultrasound and by the laparoscope during a procedure, with the images from the two modalities registered and displayed simultaneously.

In another non-limiting example, a 3D MRI image of the abdomen can be made prior to the procedure. During the procedure, the stored MRI image is registered with 3D structured light images from the laparoscope, providing the surgeon with an enhanced 3D view, in which the visibility of blood vessels and of tumors has been increased.

In some embodiments, the laparoscope optics comprise at least one wide-angle lens, so that the field of view of the camera comprises substantially all of the region of interest, the surgical field. For non-limiting example, for an abdominal operation, the field of view would be substantially all of the interior of the abdomen.

A wide-angle lens can be selected from a group consisting of: a fish-eye lens, an omnidirectional lens, any other conventional wide-angle lens and any combination thereof.

In some embodiments, the display provides a 3D view of the region of interest. In preferred embodiments, structured light is used to provide the 3D view.

The structured light method produces 3D images using a single 2D camera. In the structured light method, an object is illuminated by a set of rays of light, each ray emitted from a known position in a known direction, and each ray emitted at a known time. For each known time, a 2D camera image is created from light reflected from the spots created from rays existing at that time. Initially, a known calibration object is illuminated. From the known shape, size and position of the calibration object and from the locations in the camera images of the reflected light, mathematical matrices can be calculated. These matrices enable calculation of the 3D location of the surface of an unknown object, when the unknown object is illuminated by the same set of rays as illuminated the calibration object. It should be noted that the calibration need be done only once; there is no need to recalibrate for each surgical operation.

In preferred embodiments, the system comprises software for fog removal. Any fog removal technique known in the art can be used. Typical fog removal algorithms comprise, but are not limited to, adjustment of brightness and contrast of pixels or voxels in an image to compensate for the fog; estimating the fog density pixel by pixel (or voxel by voxel) and removing it; estimating an overall fog density and removing the overall fog density from each pixel or voxel; estimating the fog density at the deepest point in the image, scaling the fog density by the estimated distance to the object, and removing the scaled density from each pixel or voxel, and any combination thereof.

EXAMPLES

Examples are given in order to prove the embodiments claimed in the present invention. The examples describe the manner and process of the present invention and set forth the best mode contemplated by the inventors for carrying out the invention, but are not to be construed as limiting the invention.

In the examples below, similar numbers refer to similar parts in all of the figures.

Example 1—Tracking System with Collision Avoidance System

Some embodiments of such a rule-based system comprise the following set of commands: Detection (denoted by Gd):
$Gd_1$ Tool location detection function
$Gd_2$ Organ (e.g. Liver) detection function
$Gd_3$ Movement (vector) calculation and estimation function
$Gd_4$ Collision probability detection function
Tool Instructions (denoted Gt):
$Gt_1$ Move according to manual command
$Gt_2$ Stop movement
The scenario—manual move command by the surgeon:
Locations $Gd_1(t)$ and $Gd_2(t)$ are calculated in real time at each time step (from an image or location marker).
Tool movement vector $Gd_3(t)$ is calculated from $Gd_1(t)$ as the difference between the current location and at least one previous location (probably also taking into account previous movement vectors).
The probability of collision—$Gd_4(t)$—is calculated, for example, from the difference between location $Gd_1$ and location $Gd_2$ (the smaller the distance, the closer the proximity and the higher the probability of collision), from movement vector $Gd_3(t)$ indicating a collision, etc.

Tool Instructions $Gt_1$ Weight function $\alpha_1(t)=1$ if $Gt_1$ (t)<(a predetermined threshold) and 0 otherwise Tool Instructions $Gt_2$ Weight function $\alpha_2(t)=1$ if $Gt_2$ (t)>(a predetermined threshold) and 0 otherwise Tool Instructions=$\alpha_1(t)*Gt_1+\alpha_2(t)*Gt_2(t)$;

In reference to FIG. 1, which shows, in a non-limiting manner, an embodiment of a tracking system and collision avoidance system. The system tracks a tool 310 and the liver 320, in order to determine whether a collision between the tool 310 and the liver 320 is possible within the next time step. FIGS. 1A and 1B show how the behavior of the system depends on the distance 330 between the tool 310 and the liver 320, while FIGS. 1C and 1D show how movement of the tool 310 affects the behavior. In FIG. 1A, the distance 330 between the tool 310 and the liver 320 is large enough that a collision is not possible in that time step. Since no collision is possible, no movement of the tool is commanded. In FIG. 1B, the distance 330 between the tool 310 and the liver 320 is small enough that a collision is likely. In the embodiment illustrated, a movement 340 is commanded to move the tool 310 away from the liver 320. In other embodiments, the system prevents movement 350, but does not command movement 340; in such embodiments, the tool 310 will remain close to the liver 320. In yet other embodiments, the system warns/signals the operator that the move is restricted, but does not restrict movement 350 or command movement 340 away from the liver. Such a warning/signaling can be visual or aural, using any of the methods known in the art.

Figure 1C:
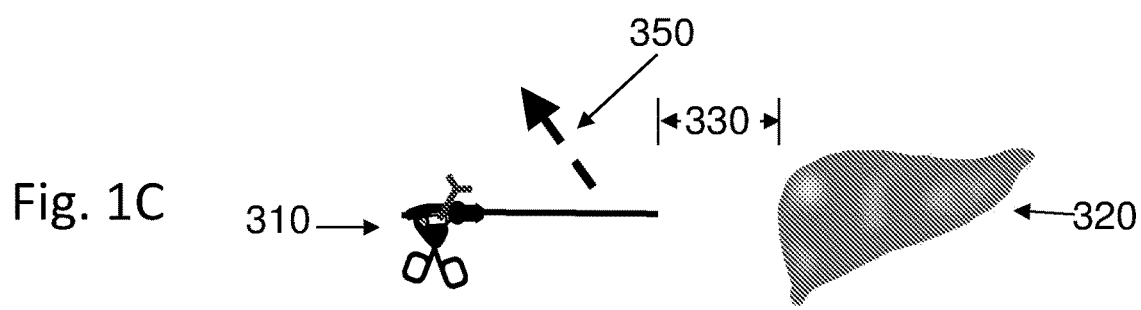
Figure 1D:
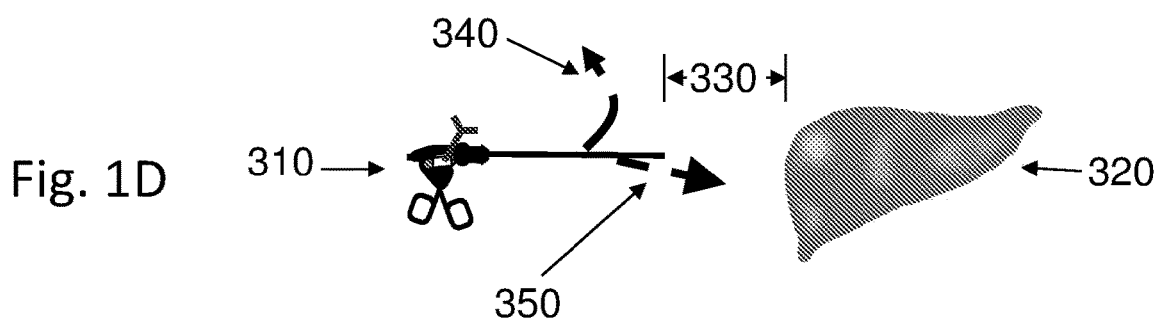

FIGS. 1C and 1D illustrate schematically the effect of the movement of tool 310 on the collision avoidance system. In FIGS. 1C and 1D, the tool 310 is close enough to the liver 320 that a collision between the two is possible. If the system tracked only the positions of the tool 310 and the liver 320, then motion of the tool 310 away from the liver 320 would be commanded. FIG. 1C illustrates the effect of a movement 350 that would increase the distance between tool 310 and liver 320. Since the movement 350 is away from liver 320, no collision is possible in this time step and no movement of the tool 310 is commanded.

In FIG. 1D, tool 310 is the same distance from liver 320 as in FIG. 1C. However, in FIG. 1D, the movement 350 of the tool 310 is toward the liver 320, making a collision between tool 310 and liver 320 possible. In some embodiments, a movement 340 is commanded to move the tool 310 away from the liver 320. In other embodiments, the system prevents movement 350, but does not command movement 340; in this embodiment the tool 310 will remain close to the liver 320. In yet other embodiments, the system warns the operator that move is restricted, but does not restrict movement 350 or command movement 340 away from the liver. Such a warning can be visual or aural, using any of the methods known in the art.

As a non-limiting example, in an operation on the liver, the collision detection function can warn the operator that a collision between a tool and the liver is likely but not prevent the collision. In an operation on the gall bladder, the collision detection function can prevent a collision between the tool and the liver, either by preventing the movement or by commanding a movement redirecting the tool away from the liver.

Example 2—Tracking System with Soft Control—Fast Movement when Nothing is Nearby, Slow Movement when Something is Close Some embodiments of such rule-based system comprise the following set of commands:

Detection (denoted by Gd):
Main tool location detection function (denoted by $Gd_M$);
Gd-tool$_1$-K—Tool location detection function;
Gd-organ$_2$-L—Organ (e.g. Liver) detection function;
$Gd_3$ Main tool movement (vector) calculation and estimation function;
$Gd_4$ Proximity probability detection function;
Tool instructions (denoted Gt):
$Gt_1$ Movement vector (direction and speed) according to manual command The scenario—manual move command by the surgeon:
Locations $Gd_M(t)$, Gd-tool$_1$-K(t) and Gd-organ$_2$-L(t) are calculated in real time at each time
step (from image or location marker).
Main Tool Movement Vector $Gd_3(t)$ is calculated per $Gd_M(t)$ as the difference between the current location and at least one previous location (probably also taking into account previous movement vectors)
The proximity of the main tool to other tools—$Gd_4(t)$—is calculated, for example, as the smallest of the differences between the main tool location and the other tools' locations.
Tool Instructions $Gt_1$ Weight function $\alpha_1(t)$ is proportional to tool proximity function $Gd_4(t)$, the closer the tool the slower the movement so that, for example $\alpha_2(t)=Gd_4/\text{maximum}(Gd_4)$ or $\alpha_2(t)=\log(Gd_4/\text{maximum}(Gd_4))$ where maximum $(Gd_4)$ is the maximum distance which is likely to result in a collision given the distances, the speed of the tool and the movement vector.

Tool Instructions=$\alpha_1(t)*Gt_1$.

Example 3—Tracking System with No-Fly Rule/Function

In reference to FIG. 2, which shows, in a non-limiting manner, an embodiment of a tracking system with no-fly rule. The system tracks a tool 310 with respect to a no-fly zone (460), in order to determine whether the tool will enter the no-fly zone (460) within the next time step. In this example, the no-fly zone 460 surrounds the liver.

Figure 2A:
FIG. 2A-D schematically illustrates operation of an embodiment of a tracking system with no fly zone rule/function.
Figure 2B:
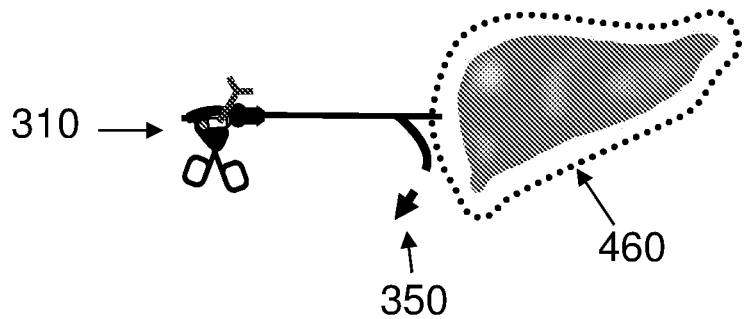
Figure 2C:
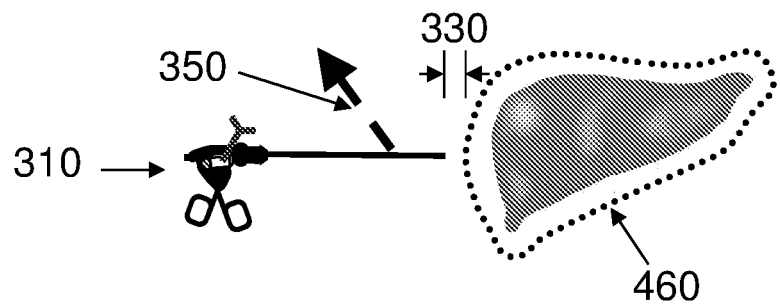
Figure 2D:
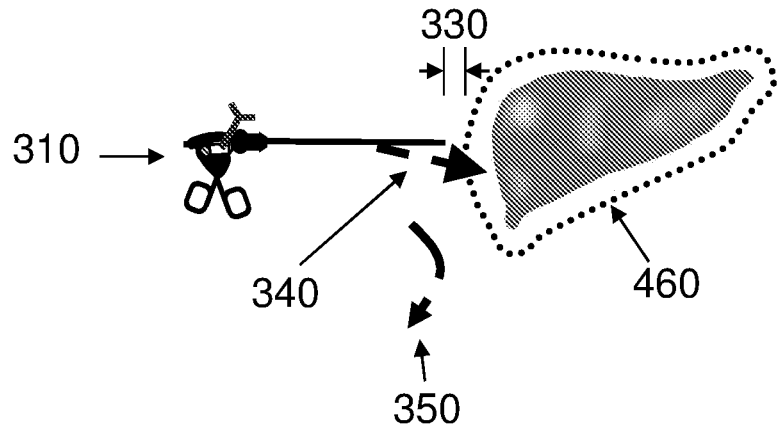

FIGS. 2A and 2B show how the behavior of the system depends on the location of the tool tip with respect to the no-fly zone, while FIGS. 2C and 2D show how movement of the tool affects the behavior.

In FIG. 2A, the tool 310 is outside the no-fly zone rule/function 460 and no movement of the tool is commanded. In FIG. 2B, the tool 310 is inside the no-fly zone 460.

The no-fly zone rule/function performs as follows:
In the embodiment illustrated, a movement 350 is commanded to move the tool 310 away from the no-fly zone 460. In other embodiments, the system prevents movement further into the no-fly zone (refers as movement 340, see FIG. 2C), but does not command movement 340; in such embodiments, the tool 310 will remain close to the no-fly zone 460.

In yet other embodiments, the system warns/signals the operator that the move is restricted, but does not restrict movement further into the no-fly zone or command movement 340 away from the no-fly zone 460. Such a warning/signaling can be visual or aural, using any of the methods known in the art.

FIGS. 2C and 2D illustrate schematically the effect of the tool's movement on operation of the no-fly zone rule/function. In FIGS. 2C and 2D, the tool 310 is close enough to the no-fly zone 460 (distance 330 is small enough) that it is possible for the tool to enter the no-fly zone during the next time step. FIG. 2C illustrates the effect of a movement 340 that would increase the distance between tool 310 and no-fly zone 460. Since the movement 340 is away from no-fly zone 460, no collision is possible in this time step and no movement of the tool 310 is commanded.

In FIG. 2D, tool 310 is the same distance from no-fly zone 460 as in FIG. 2C. However, in FIG. 2D, the movement 340 of the tool is toward no-fly zone 460, making it possible for tool 310 to enter no-fly zone 460. In the embodiment illustrated, a movement 350 is commanded to move the tool 310 away from the no-fly zone 460. In other embodiments, the system prevents movement 340, but does not command movement 350; in such embodiments, the tool 310 will remain close to the no-fly zone 460. In yet other embodiments, the system warns/signals the operator that the move is restricted, but does not restrict movement 340 or command movement 350 away from the no-fly zone rule/function 460. Such a warning/signaling can be visual or aural, using any of the methods known in the art.

Example 4—Tracking System with Preferred Volume Zone Rule/Function

In reference to FIG. 3, which shows, in a non-limiting manner, an embodiment of a tracking system with a preferred volume zone function/rule.

The system tracks a tool 310 with respect to a preferred volume zone (570), in order to determine whether the tool will leave the preferred volume (570) within the next time step.

Figure 3A:
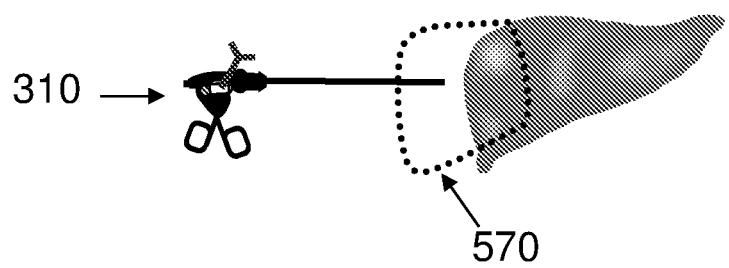
FIG. 3A-D schematically illustrates operation of an embodiment of a tracking system with preferred volume zone rule/function.
Figure 3B:
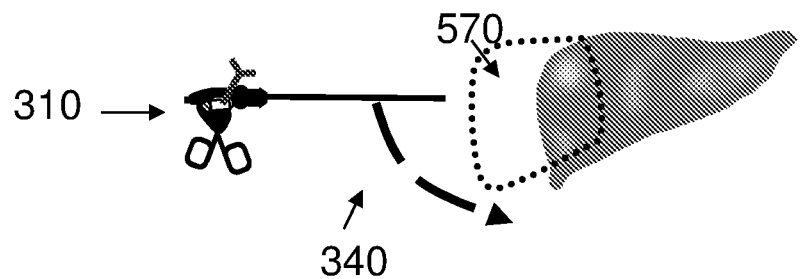

In this example, the preferred volume zone 570 extends over the right lobe of the liver. FIGS. 3A and 3B show how the behavior of the system depends on the location of the tool tip with respect to the preferred volume zone 570, while FIGS. 3C and 3D show how movement of the tool affects the behavior (i.e., the preferred volume zone rule/function).

In FIG. 3A, the tool 310 is inside the preferred volume zone 570 and no movement of the tool is commanded. In FIG. 3B, the tool 310 is outside the preferred volume zone 570.

In the embodiment illustrated, a movement 340 is commanded to move the tool 310 away from the preferred volume zone 570. In other embodiments, the system prevents movement 340; in such embodiments, the tool 310 will remain close to the preferred volume zone 570. In yet other embodiments, the system warns/signals the operator that the move 340 is restricted. Such a warning/signaling can be visual or aural, using any of the methods known in the art.

Figure 3C:
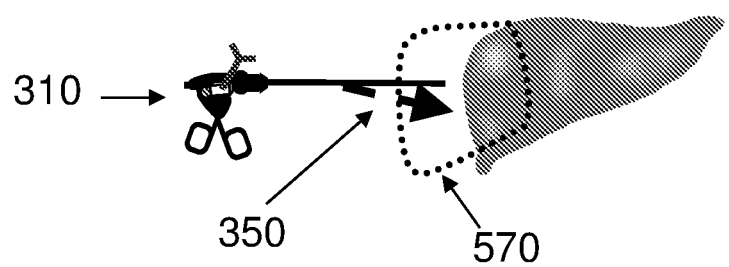
Figure 3D:
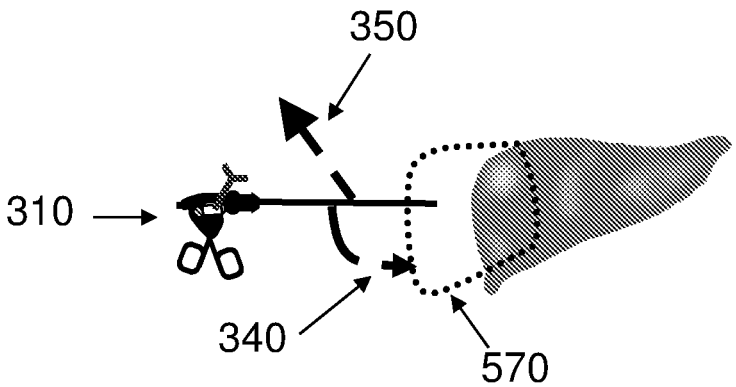

FIGS. 3C and 3D illustrate schematically the effect of the tool's movement on operation of the preferred volume rule/function. In FIGS. 3C and 3D, the tool 310 is close enough to the edge of preferred volume zone 570 that it is possible for the tool to leave the preferred volume zone during the next time step.

FIG. 3C illustrates the effect of a movement 350 that would take the tool 310 deeper into preferred volume zone 570. Since the movement 350 is into preferred volume 570, said movement is an allowed movement.

In FIG. 3D, the movement 350 of the tool is out of the preferred volume 570, making it possible for tool 310 to leave preferred volume 570.

According to the exemplary embodiment illustrated, a movement 340 is commanded to move the tool 310 into the preferred volume zone 570. In other embodiments, the system prevents movement 350, but does not command movement 340; in such embodiments, the tool 310 will remain close to the preferred volume zone 570. In yet other embodiments, the system warns/signals the operator that the move is restricted, but does not restrict movement 350 or command movement 340 away from the preferred volume zone 570. Such a warning/signaling can be visual or aural, using any of the methods known in the art.

Example 5—Organ/Tool Detection Function

Figure 4:
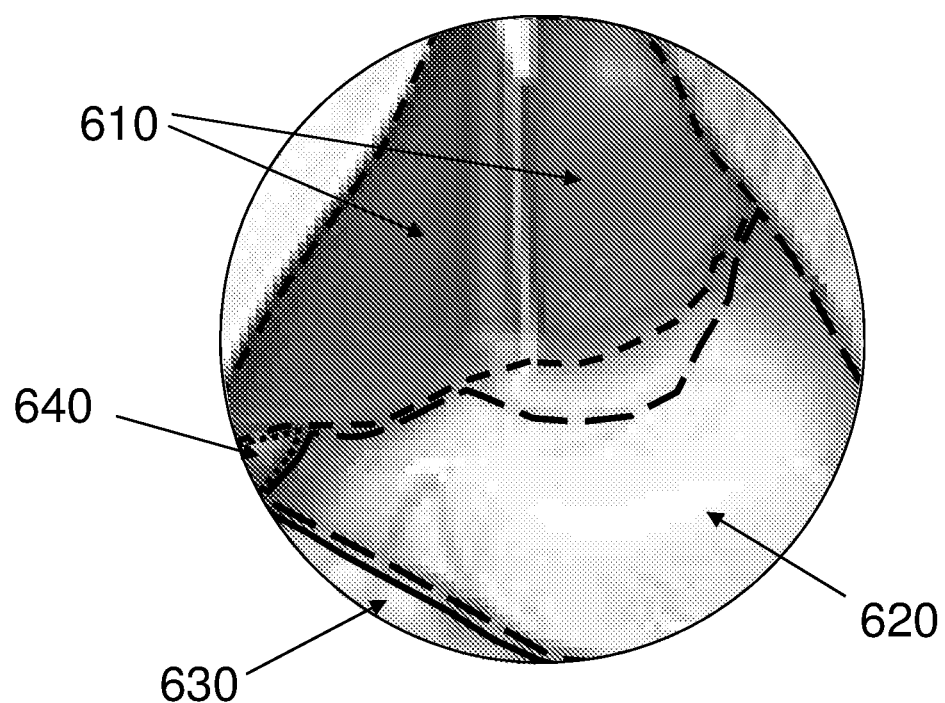
FIG. 4 schematically illustrates operation of an embodiment of the organ detection function/rule.

In reference to FIG. 4, which shows, in a non-limiting manner, an embodiment of an organ detection system (however, it should be noted that the same is provided for detection of tools, instead of organs).

For each organ, the 3D spatial positions of the organs stored in a database. In FIG. 4, the perimeter of each organ is marked, to indicate the edge of the volume of 3D spatial locations stored in the database.

In FIG. 4, the liver 610 is labeled with a dashed line. The stomach 620 is labeled with a long-dashed line, the intestine 630 with a solid line and the gall bladder 640 is labeled with a dotted line.

In some embodiments, a label or tag visible to the operator is also presented. Any method of displaying identifying markers known in the art can be used. For non-limiting example, in an enhanced display, colored or patterned markers can indicate the locations of the organs, with the marker either indicating the perimeter of the organ or the area of the display in which it appears.

Example 6—Tool Detection Function

Figure 5:
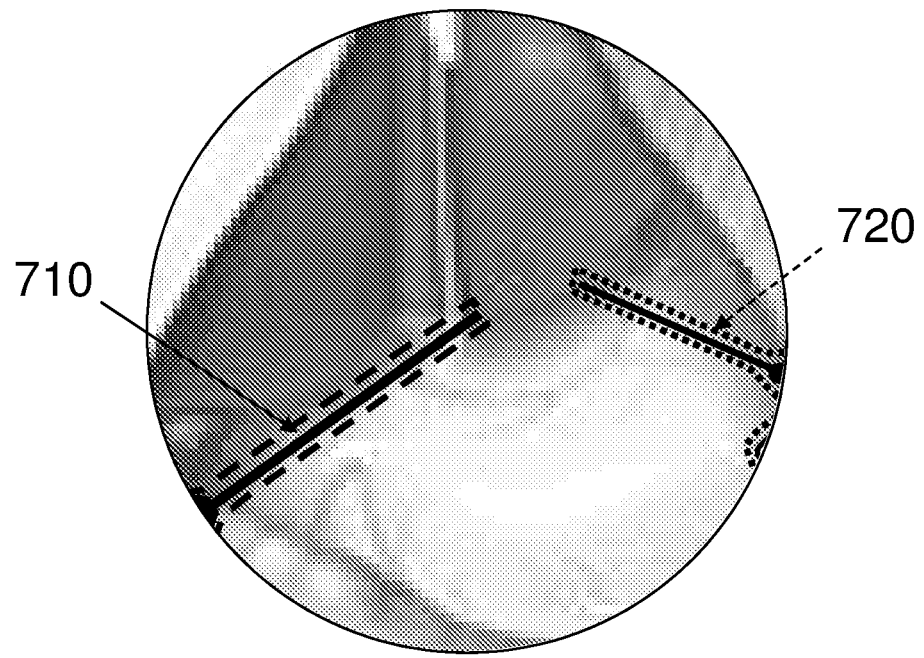
FIG. 5 schematically illustrates operation of an embodiment of the tool detection function/rule.

In reference to FIG. 5, which shows, in a non-limiting manner, an embodiment of a tool detection function. For each tool, the 3D spatial positions of the tools stored in a database. In FIG. 5, the perimeter of each tool is marked, to indicate the edge of the volume of 3D spatial locations stored in the database. In FIG. 5, the left tool is labeled with a dashed line while the right tool is labeled with a dotted line.

In some embodiments, a label or tag visible to the operator is also presented. Any method of displaying identifying markers known in the art can be used. For non-limiting example, in an enhanced display, colored or patterned markers can indicate the locations of the tools, with the marker either indicating the perimeter of the tool or the area of the display in which it appears.

Example 7—Movement Detection Function/Rule

Figure 6A:
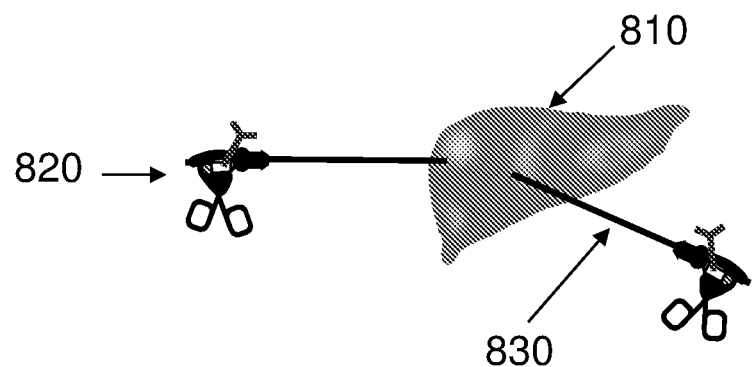
FIG. 6A-B schematically illustrates operation of an embodiment of the movement detection function/rule.
Figure 6B:
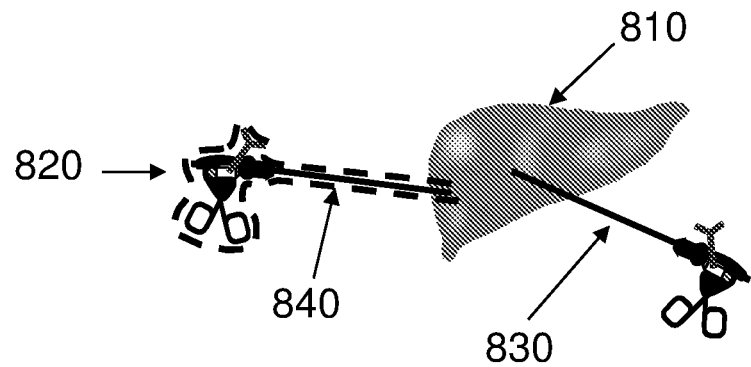

In reference to FIG. 6, which shows, in a non-limiting manner, an embodiment of a movement detection function/rule. FIG. 6A schematically illustrates a liver 810, a left tool 820 and a right tool 830 at a time t. FIG. 6B schematically illustrates the liver 810, left tool 820 and right tool 830 at a later time t+Δt, where Δt is a small time interval. In this example, the left tool 820 has moved downward (towards the direction of liver 810) in the time interval Δt.

The system has detected movement of left tool 820 and labels it. This is illustrated schematically in FIG. 6B by a dashed line around left tool 820.

Example 8—Prediction Function

In reference to FIG. 7, which shows, in a non-limiting manner, an embodiment of the above discussed prediction function.

Figure 7A:
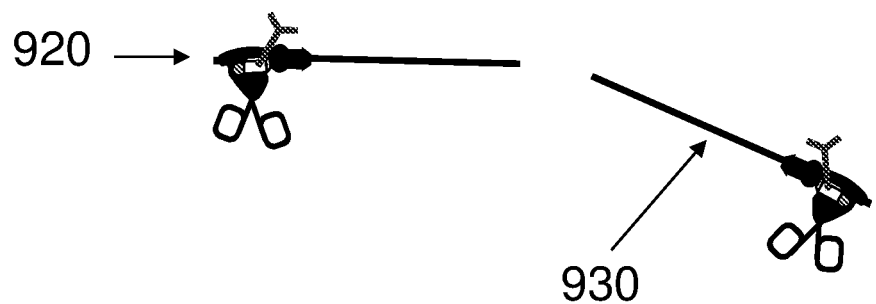
FIG. 7A-D schematically illustrates operation of an embodiment of the prediction function/rule.

FIG. 7A shows a left tool 920 and a right tool 930 at a time t.

Figure 7B:
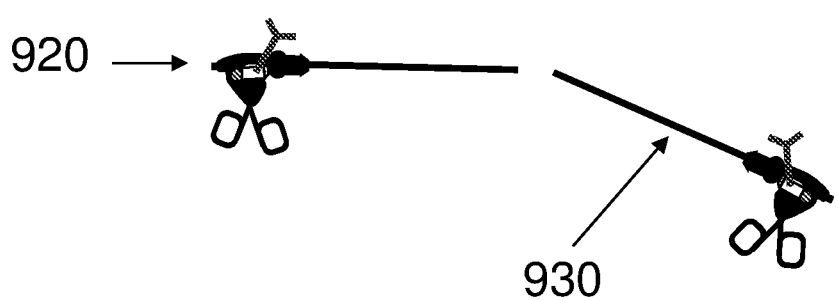
Figure 7C:
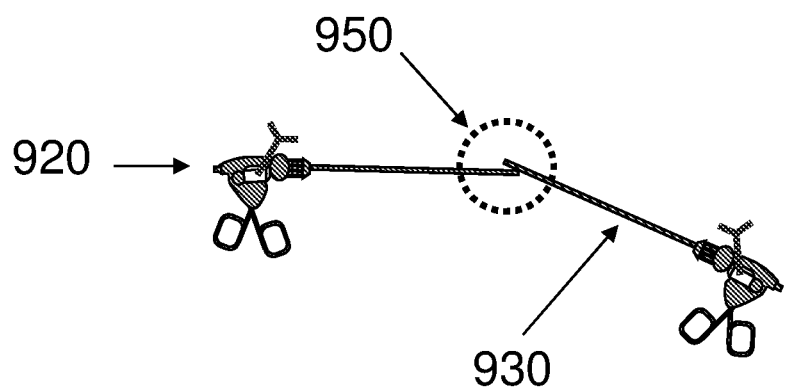
Figure 7D:
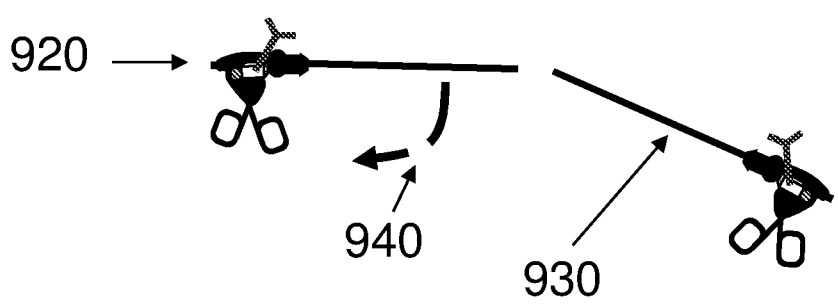

FIG. 7B shows the same tools at a later time t+Δt, where Δt is a small time interval. Left tool 920 is moving to the right and downward, while right tool 930 is moving to the left and upward. If the motion continues (shown by the dashed line in FIG. 7C), then by the end of the next time interval, in other words, at some time between time t+Δt and time t+2Δt, the tools will collide, as shown by tool tips within the dotted circle 950 in FIG. 7C.

In this embodiment, the system automatically prevents predicted collisions and, in this example, the system applies a motion 940 to redirect left tool 920 so as to prevent the collision.

In other embodiments, the system warns/signals the operator that a collision is likely to occur, but does not alter the movement of any tool. Such a warning/signaling can be visual or aural, using any of the methods known in the art.

In other embodiments, the prediction function can be enabled to, for non-limiting example, alter the field of view to follow the predicted movement of a tool or of an organ, to warn of (or prevent) predicted motion into a no-fly zone, to warn of (or prevent) predicted motion out of a preferred zone.

Example 9—Right Tool Function/Rule

Figure 8:
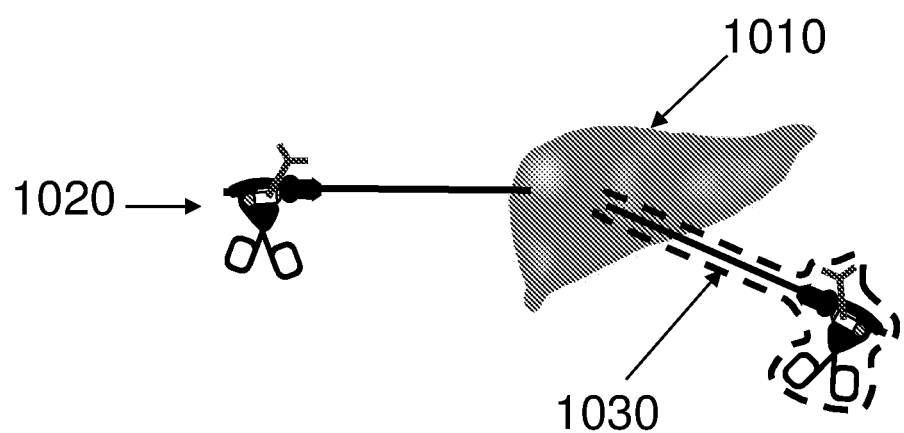
FIG. 8 schematically illustrates operation of an embodiment of the right tool function/rule.

In reference to FIG. 8, which shows, in a non-limiting manner, an embodiment of a right tool rule/function. FIG. 8 schematically illustrates a liver 1010, a left tool 1020 and a right tool 1030. The right tool, illustrated schematically by the dashed line 1040, is labeled and its 3D spatial location is constantly identified and real-time stored in a database. Now, according to the right tool function/rule the endoscope constantly tracks the right tool.

It should be pointed out that the same rule/function applies for the left tool (the left tool function/rule), except that it is the left tool whose 3D spatial location is constantly identified and real-time stored in a database, and it is the left too that is tracked.

Example 10—Field of View Function/Rule

In reference to FIG. 9, which shows, in a non-limiting manner, an embodiment of a field of view function/rule.

Figure 9A:
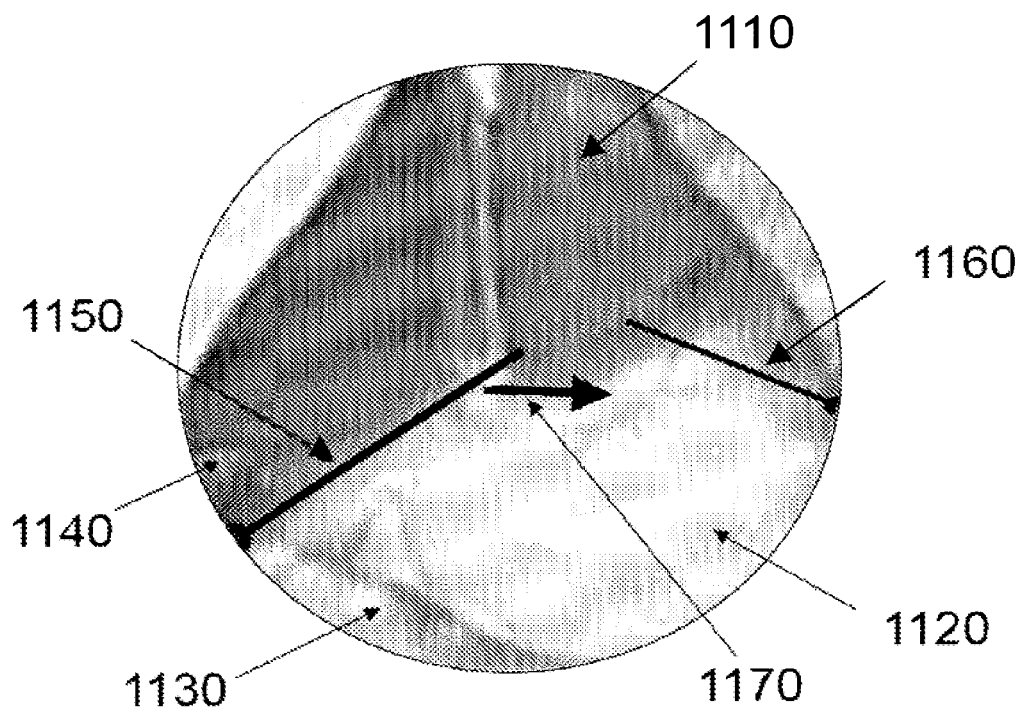
FIG. 9A-B schematically illustrates operation of an embodiment of the field of view function/rule.

FIG. 9A schematically illustrates a field of view of the abdomen at a time t. In the field of view are the liver 1110, stomach 1120, intestines 1130 and gall bladder 1140.

The gall bladder is nearly completely visible at the left of the field of view. Two tools are also in the field of view, with their tips in proximity with the liver. These are left tool 1150 and right tool 1160. In this example, the field of view function/rule tracks left tool 1150. In this example, left tool 1150 is moving to the right, as indicated by arrow 1170.

Figure 9B:
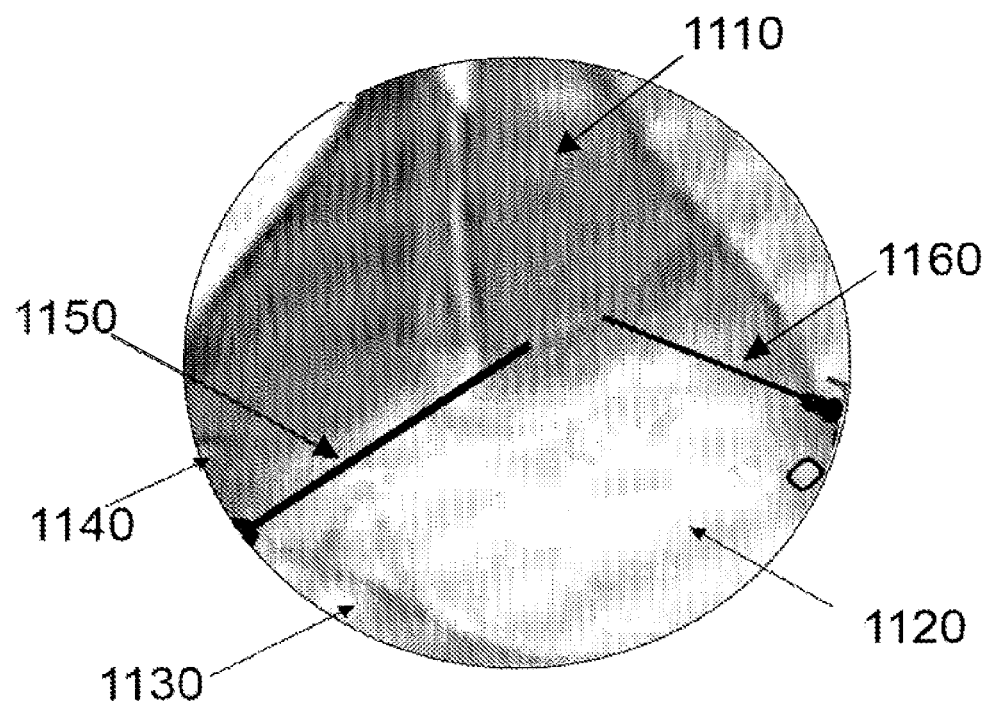

FIG. 9B shows the field of view at time t+Δt. The field of view has moved to the right so that the tip of left tool 1150 is still nearly at the center of the field of view. It can be seen that much less of gall bladder 1140 is visible, while more of right tool 1160 has entered the field of view.

The field of view function/rule can be set to follow a selected tool, as in this example or to keep a selected organ, tissue or other portion of a patient in the center of the field of view. It can also be set to keep a particular set of tools in the field of view, zooming in or out as necessary to prevent any of the selected tools from being outside the field of view.

Alternatively, the field of view function/rule defines n 3D spatial positions; n is an integer greater than or equal to 2;

the combination of all of said n 3D spatial positions provides a predetermined field of view.

Each movement of the endoscope or the surgical tool within said n 3D spatial positions is an allowed movement and any movement of the endoscope or the surgical tool outside said n 3D spatial positions is a restricted movement.

Alternatively, said the field of view function/rule defines n 3D spatial positions; n is an integer greater than or equal to 2; the combination of all of said n 3D spatial positions provides a predetermined field of view.

According to the field of view function/rule, the endoscope is relocated if movement has been detected by said detection means, such that said field of view is maintained.

Example 11—Tagged Tool Function/Rule (or Alternatively the Preferred Tool Rule)

Figure 10:
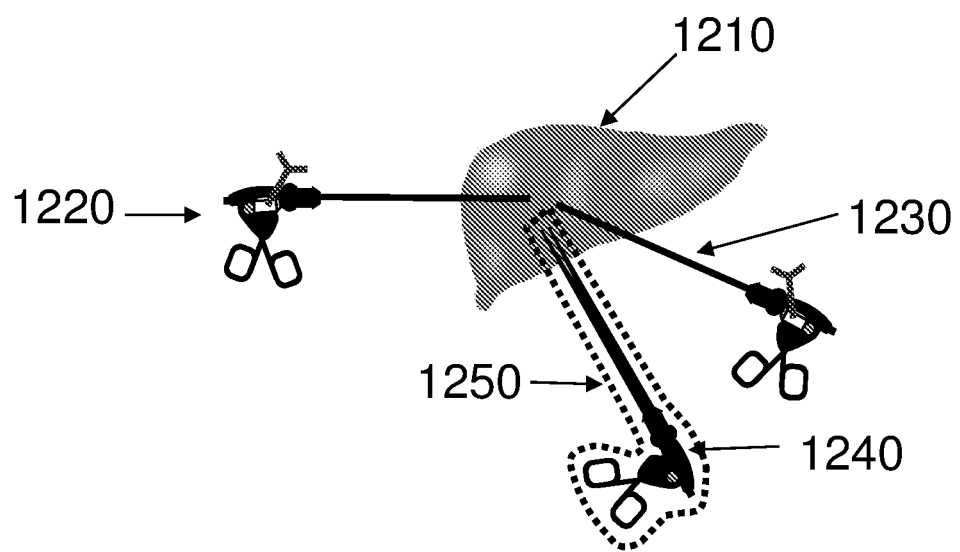
FIG. 10 schematically illustrates operation of an embodiment of the tagged tool function/rule.

In reference to FIG. 10, which shows, in a non-limiting manner, an embodiment of a tagged tool function/rule.

FIG. 10 shows three tools (1220, 1230 and 1240) in proximity to the organ of interest, in this example, the liver 1210.

The tool most of interest to the surgeon, at this point during the operation, is tool 1240. Tool 1240 has been tagged (dotted line 1250); the 3D spatial location of tool 1240 is constantly stored in a database and this spatial location has been labeled as one of interest.

The system can use this tagging for many purposes, including, but not limited to, keeping tool 1240 in the center of the field of view, predicting its future motion, keeping it from colliding with other tools or keeping other tools from colliding with it, instructing the endoscope to constantly monitor and track said tagged tool 1250 and so on.

It should be noted that in the preferred tool rule, the system tags one of the tools and performs as in the tagged tool rule/function.

Example 12—Proximity Function/Rule

In reference to FIG. 11, which shows, in a non-limiting manner, an embodiment of a proximity function/rule.

FIG. 11A schematically illustrates two tools (1310 and 1320) separated by a distance 1330 which is greater than a predefined proximity distance. Since tool 1310 is not within proximity of tool 1320, the field of view (1380) does not move.

FIG. 11B schematically illustrates two tools (1310 and 1320) separated by a distance 1330 which is less than a predefined proximity distance.

Since tool 1310 is within proximity of tool 1320, the field of view 1380 moves upward, illustrated schematically by arrow 1340, until the tips of tool 1310 and tool 1320 are in the center of field of view 1380 (FIG. 11C).

Alternatively the once the distance 1330 between the two tool 1320 and 1310 is smaller than a predetermined distance, the system alerts the user of said proximity (which might lead to a collision between the two tools). Alternatively, the system moves one of the tools away from the other one.

Example 13—Operator Input Function/Rule

In reference to FIG. 12, which shows, in a non-limiting manner, an embodiment of an operator input function/rule. According to this embodiment, input is received from the operator.

In the following example, the input received from the operator is which tool to track.

Figure 12A:
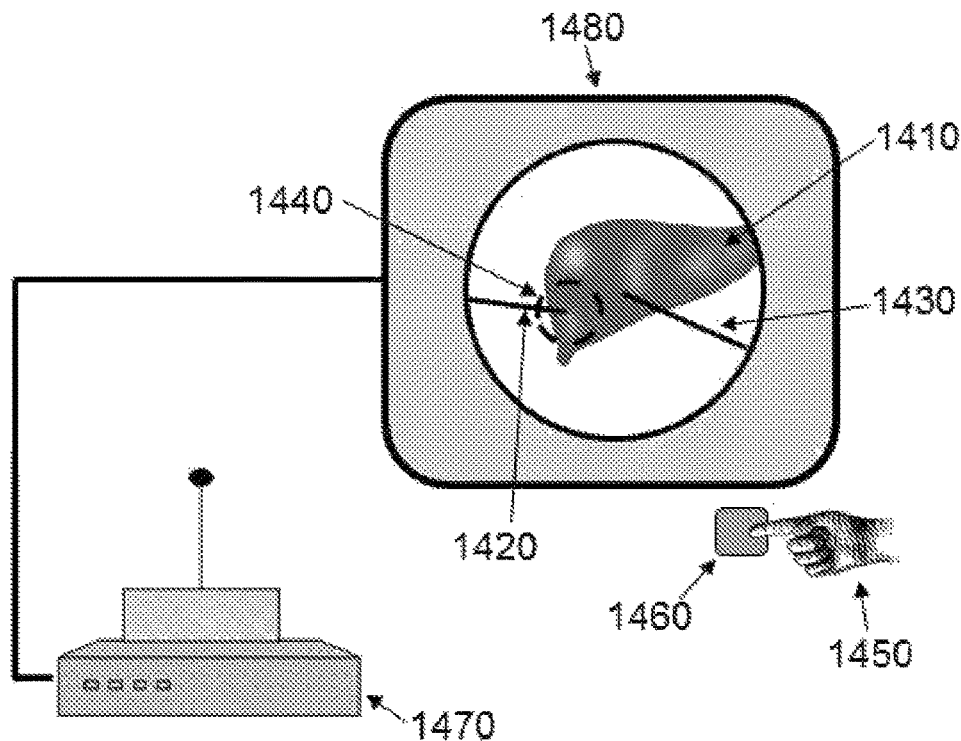
FIG. 12A-B schematically illustrates operation of an embodiment of the operator input function/rule.

FIG. 12A schematically illustrates an endoscope with field of view 1480 showing a liver 1410 and two tools 1420 and 1430. A wireless transmitter 1460 is enabled to transmit coded instructions through receiver 1470. Operator 1450 first selects the tip of the left tool as the region of interest, causing the system to tag (1440) the tip of the left tool.

Figure 12B:
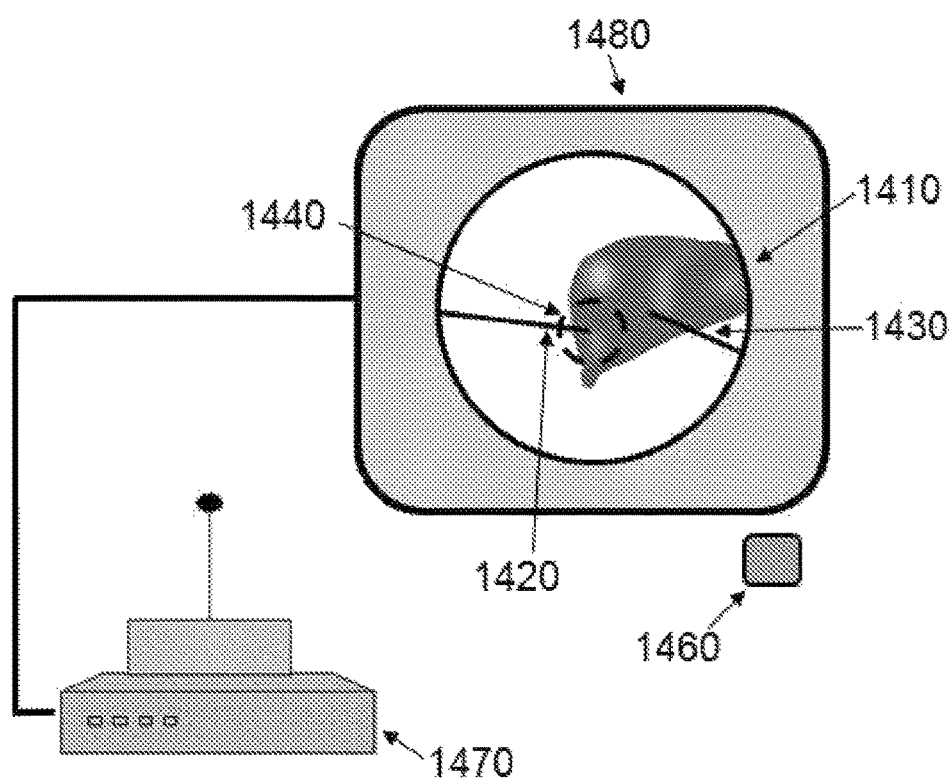

As illustrated in FIG. 12B, the system then directs and modifies the spatial position of the endoscope so that the tagged tool tip 1440 is in the center of the field of view 1480.

Another example of the operator input function/rule is the following:

If a tool has been moved toward an organ or other tissue and is within a predetermined distance of the organ or tissue then, according to the proximity rule or the collision prevention rule, the system will, according to some embodiments, prevent further movement of the surgical tool toward the organ or tissue.

According to some embodiments of the present invention, once the surgical tool has been stopped, any movement of said tool in the direction toward the organ or tissue is interpreted as input from an operator to continue the movement of said surgical tool in said direction.

Thus, according to this embodiment, the operator input function/rule receives input from the operator (i.e., physician) to continue the movement of the surgical tool (even though it is "against" the collision prevention rule). The input is simply in the form of the continued movement of the surgical tool (after the alert provided by the system or after the movement prevention by the system).

Example 14—Constant Field of View Rule/Function

In reference to FIGS. 13A-D, which shows, in a non-limiting manner, an embodiment of a tracking system with a constant field of view rule/function.

In some endoscopic systems, the tip lens in the camera optics is not at a right angle to the sides of the endoscope. Conventionally, the tip lens angle is described relative to a right angle, so that a tip lens at right angles to the sides of the endoscope is described as having an angle of 0. Typically, angled endoscope tip lenses have an angle of 30° or 45°. This tip lens angle affects the image seen during zooming. FIG. 13A-E illustrates, in an out-of-scale manner, for a conventional system, the effect of zooming in the field of view in an endoscope with tip lens set straight in the end (FIGS. 13A and 13C) vs. the effect of zooming in the field of view in an endoscope with angled tip lens (FIGS. 13D and 13E).

FIGS. 13A and 13D illustrate the endoscope (100), the object it is viewing (200) and the image seen by the endoscope camera (130) before the zoom. The solid arrows (160) show the limits of the FOV and the dashed arrow (170), the center of the FOV; since the object is in the center of the FOV, an image of the object (210) is in the center of the camera image (130).

FIGS. 13B and 13E illustrate the endoscope (100), the object it is viewing (200) and the image seen by the endoscope camera (130) after the zoom. The solid arrows (160) show the limits of the FOV and the dashed arrow (170), the center of the FOV.

If the tip lens is set straight in the end of the endoscope (FIGS. 13A and 13B), an object (200) in the center of the field of view will be in the center of the FOV (and the center of the camera image) (130) both before (FIG. 13A) and after (FIG. 13B) the zoom. As illustrated in an out-of-scale manner in FIG. 13C, the direction of motion of the endoscope during the zoom (180) is a straight line connecting the location of the center of the tip of the endoscope (100) at the start of the zoom with the center of the field of view at the start (and end) (170) of the zoom; the center of the endoscope tip will lie on this line at all times during the zoom.

However, if the tip lens is set at an angle in the end of the endoscope (FIGS. 13D and 13E), then an object that is in the center of the FOV (and the camera image) before the zoom (FIG. 13D) will not be in the center of the FOV (or the camera image) after the zoom (FIG. 13E) since the direction of motion of the endoscope is not the direction in which the center of the FOV (170) points.

In some embodiments of the system of the present invention, the controller maintains a fixed center of the FOV during zoom independent of the tip lens angle. In such systems, (FIGS. 13F and 13G) the endoscope (100) tip will move in a curved trajectory (180, FIG. 13F) such that the center of the FOV does not change during zooming (FIG. 13G).

The correction of the zoom movement (and focusing on the same object within the FOV during zooming) is referred to also as the corrected zoom rule.

Maintenance of a fixed center of the FOV can be can be made either by inputting the angle of the tip lens during setup, in which case the system can calculate an appropriate trajectory, or by identifying the center of the field of view by analyzing the image. Inputting the tip lens angle means that no image analysis need be done; however, controlling the direction of motion of the endoscope during zoom via a data processing system means that the tip lens angle does not need to be input to the data processing system, obviating a possible source of error.

Example 15—Misalignment Rule/Function

According to some embodiment of the present invention, the system can inform the user of any misalignment of the same system.

Misalignment of the system can cause parasitic movement of the endoscope tip, where the endoscope tip does not move exactly in the expected direction. According to some embodiments of the system, the system comprises at least one sensor (e.g., gyroscope, accelerometer and any combination thereof) that calculates/estimates the position of the pivot point in real time in order to (a) inform the user of misalignment; or (b) calculate the misalignment so that the system can adjust its movement to prevent parasitic movement.

Example 16—Change of Speed Rule/Function

Figure 14:
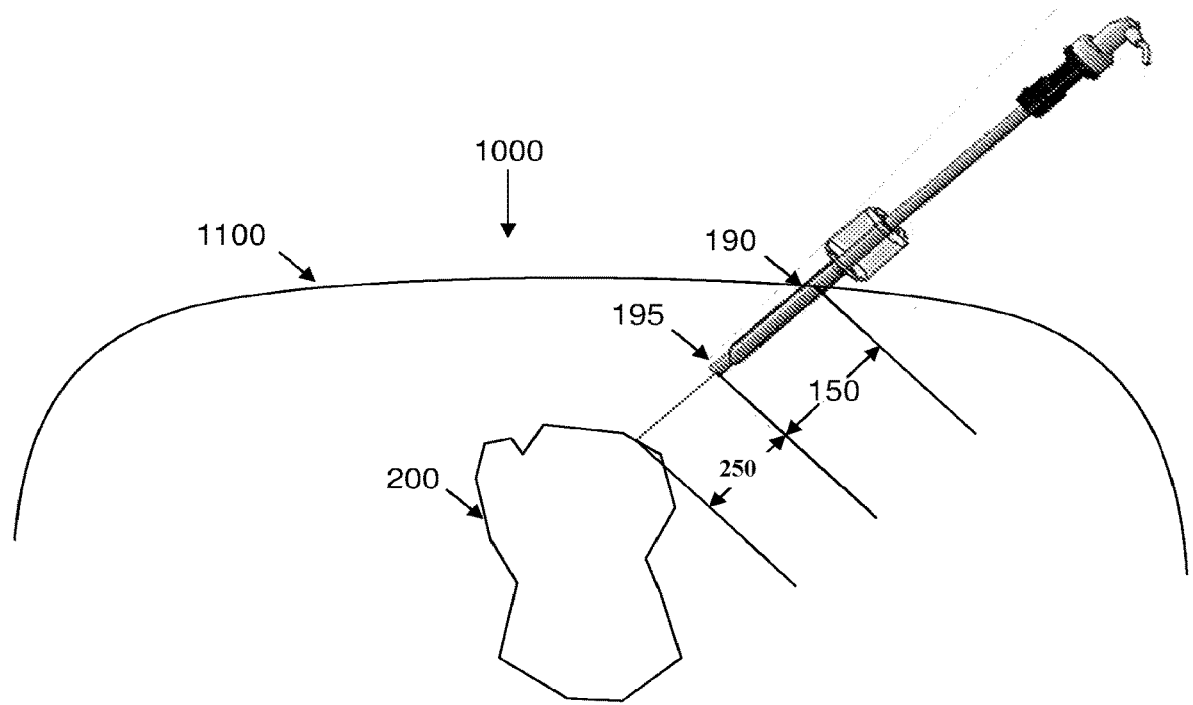
FIG. 14 schematically illustrates an embodiment of a tracking system with a change of speed rule/function.

In reference to FIG. 14, which shows, in a non-limiting manner, an embodiment of a tracking system with a change of speed rule/function.

In conventional endoscopic control systems, motion of the endoscope occurs at a single speed. This speed is fairly fast so that the endoscope can be moved rapidly between locations that are well separated. However, this means that making fine adjustments is difficult enough that fine adjustments are normally not made. In an embodiment of the present invention, the speed of the tip of the endoscope is automatically varied such that the closer the endoscope tip is to an object, be it a tool, an obstacle, or the object of interest, the more slowly the endoscope tip moves. In this embodiment, as shown in FIG. 14, measurements are made of the distance X (150) from the tip (195) of the endoscope (100) to the pivot point of the endoscope (190), where said pivot point is at or near the surface of the skin (1100) of a patient (1000). Measurements are also made of the distance Y (250) from the tip of the endoscope (195) to the object in the center of the scene of view (200). From a predetermined velocity $V_p$, the actual velocity of the tip of the endoscope at a given time, $V_{act}$, is calculated from $$V_{act} \propto \frac{Y}{X} V_p$$

Therefore, the closer the endoscope is to the object at the center of the scene of view, the more slowly the endoscope moves, making it possible to use automatic control of even fine adjustments, and reducing the probability that the endoscope will come in contact with tissue or instruments.

In some embodiments of the system, the harder the control unit is pressed, the faster the endoscope tip moves. In these embodiments, the system provides a warning if the speed is above a predetermined maximum. Examples of the method of warning include, but are not limited to, a constant volume tone, a constant pitch tone, a varying volume tone, a varying pitch tone, a vocal signal, a constant color visual signal, a constant brightness visual signal, a varying color visual signal, a varying brightness visual signal, a signal visible on at least some part of the endoscope image, a signal visible on at least some portion of the patient, a signal visible in at least some portion of the surroundings of the patient, a vibration in the control unit, a temperature change in the control unit, and any combination of the above.

According to some embodiments of the present invention, the velocity of the endoscope's movement will be adjusted as a function of the distance of the endoscope's tip from the organ\tissue, overriding the pressure on the control unit.

Example 17—Fixed Point Rule/Function

In reference to FIGS. 15-17, which show, in a non-limiting manner, embodiments of a system with a fixed point rule/function.

According to this embodiment, the endoscope 'tracks' (follows) a 'fixed point' in 3D space.

It should be emphasized that the term 'fixed point' does not refer to an absolute fixed 3D position.

The fixed point can be, for non-limiting example, fixed relative to the coordinate system of the location estimating means, or it can be fixed relative to at least one object within the body cavity, such as a tool, tissue or organ. If the point is fixed relative to the coordinate system of the location estimating means, then it functions like a conventional fixed point, being nonmoving relative to the ground. Alternatively, the 'fixed point' can be defined as a function of a predefined position (e.g., tip of a tool/s) such that when said predefined position moves (e.g., when the tool moves) said 'fixed point' moves accordingly. According to this embodiment, the endoscope follows said 'fixed point'. If the point is fixed relative to a single position on a single tool, then it functions similarly to the tagged tool function (Example 11 above).

The point can be fixed relative to two positions on a single position\tool. For non-limiting example, it can be fixed relative to the blades of a scissors or the jaws of a clamp. A non-limiting example is shown in FIG. 15A-B, which shows a fixation point which is the point in the middle of the jaws (1510, 1520) of a clamp (1500) and halfway between them (illustrated as a star). Once the jaws (1510, 1520) moved—the fixation point moves as well (see FIG. 15B relative to FIG. 15A).

The point can be fixed relative to an identifiable location on an organ, or relative to a portion of an organ. A non-limiting example of a point fixed relative to an identifiable point on an organ is fixation relative to the location of the first bifurcation in the left coronary artery. A non-limiting example of a point fixed relative to an organ is fixation relative to the center of the heart, with the center of the heart being defined as the point, on average, furthest from the perimeter of the heart. In both cases, the fixation point can move as the heart beats.

The point can also be fixed relative to more than one object. For non-limiting example, it can be fixed relative to two tools, or to both a tool and an organ. Non-limiting examples of fixation relative to two tools include a point a fixed fraction of the distance between the tool tips, a point a predetermined distance from a line joining the tool tips, or the point where two tools will contact each other, if their present movement pattern continues.

FIG. 16A-B shows two tools (920 and 930) a distance D apart, with the fixed point (illustrated as a star) halfway between them (distance D/2 from each).

Again, once one of the tool moves, the fixed point will be recalculated and re-positioned according to the predetermined criteria (in this case in the halfway between tool 920 and 930), see FIG. 16B relative to FIG. 16A.

FIG. 17A-B shows an embodiment in which the fixed position (illustrated as a star) is defined to be at a fixed distance, D from tool 930. According to this embodiment, the fixed position is also defined to be parallel to tool 930.

Again, once the tool moves, the fixed point will be recalculated and re-positioned according to the predetermined criteria (in this case at a fixed distance, D from tool 930 and parallel to the same), see FIG. 17B relative to FIG. 17A.

The system can use this tagging for many purposes, including, but not limited to, keeping the fixed point (star) in the center of the field of view, predicting its future motion, keeping it at a particular location relative to another object (e.g., keeping a clamp fixed point at the location of an incision to be clamped), instructing the endoscope to constantly track the fixed point and so on.

Example 18—Maximum Speed Rule/Function

In a variant of embodiments where an instrument is tracked, tracking occurs only if the speed of the tracked object, typically a tool, is below a predetermined maximum speed. If the speed of the tracked object is above the predetermined maximum speed, tracking is terminated.

In a further variant of such embodiments, tracking is terminated if the speed of the endoscope is above a predetermined maximum speed, independent of the speed of the tracked object.

Example 19—Physical/Virtual Zoom Rule/Function

During zoom, especially zoom inward, endoscope travel can be limited by many factors, including both limits on travel imposed by the maneuvering system, and limits on travel imposed by space available inside the body. For example, the diameter of an endoscope tip can be such that, if it were to travel further into a restricted space, it would come into contact with body tissues on at least one side.

In some embodiments, zooming-in and/or zooming out can be extended by use of virtual zoom. In such embodiments, when the endoscope has reached a determinable point in a zoom, such as, in a zoom toward an object, a position such that further travel would bring a part of the endoscope into contact with an organ, the endoscope ceases to move. However, the image as seen in a display continues to zoom, with the system generating the zoomed image. In some embodiments, further detail is apparent as the image continues to zoom. This information can be from sub-pixel information from stored information, from information from other modalities, from any other conventional image-enhancement process and any combination thereof. In some embodiments, the image of the center of the field of view will enlarge, but no new information will be available. Any combination of the above can be used.

In virtual zoom outward, in some embodiments, the endoscope uses a lens such that the displayed image only comprises a part of the lens field of view, thus enabling enlargement of the displayed region of the body during virtual zoom outward. In some embodiments, stored information is used to enlarge the displayed region.

Example 20—Virtual Rotation of Scene Rule/Function

A non-limiting example of virtual rotation of a scene will be given in FIG. 18A-C. FIG. 18A shows an endoscope (100) with an alignment (172) at some time $t_a$. The image (210) in the display (130) has an alignment (215) corresponding to the alignment (172) of the endoscope (100).

In the course of time, the alignment of the endoscope (100) rotates (150). At some later time $t_b$, (FIG. 18B) the alignment of the endoscope (100) has rotated by an angle θ. In a conventional endoscope, this will rotate the image (210) in the display (130) by the same angle θ.

In preferred embodiments of the present invention, as shown in FIG. 18C, as the alignment of the endoscope changes, software rotates (155, FIG. 18B) the image (210) so that the alignment (215) of the image (210) remains the same, no matter what the alignment (172) of the endoscope.

Example 21—Input Protocol, Movement of a Tool

Non-limiting examples of input protocols involving movement of tools and associated output protocols—output surgical procedures—will be given. For simplicity, the input commands comprise a single movement protocol. It is clear that a movement command can comprise any number of movement protocols, positions, repositions and actions.

In reference to FIG. 19A-B, which shows, in a non-limiting manner, an embodiment of an input protocol comprising shaking a tool.

In FIG. 19A, a system comprising three tools (1520, 1530, 1540) is illustrated; the system is tracking (dashed line) the upper right tool (1530). In order to change tracking to the leftmost tool (1520), the leftmost tool (1520) is shaken (1550, dotted line)

As shown in FIG. 19B, once the leftmost tool (1520) has been shaken, according to the output protocol, the system tracks (dashed line) the leftmost tool (1520).

In this example, for clarity, a single tool is tracked. It is clear that a plurality of tools can be simultaneously tracked.

Figure 20A:
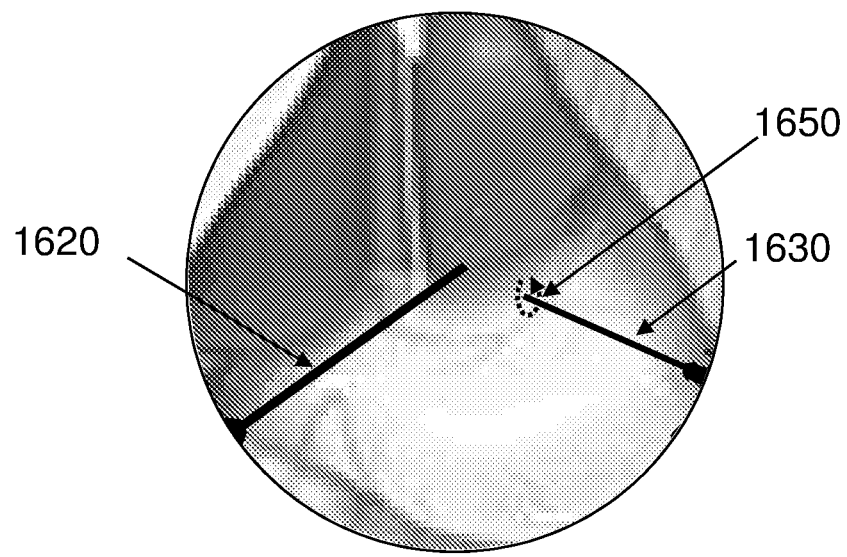
Figure 20B:
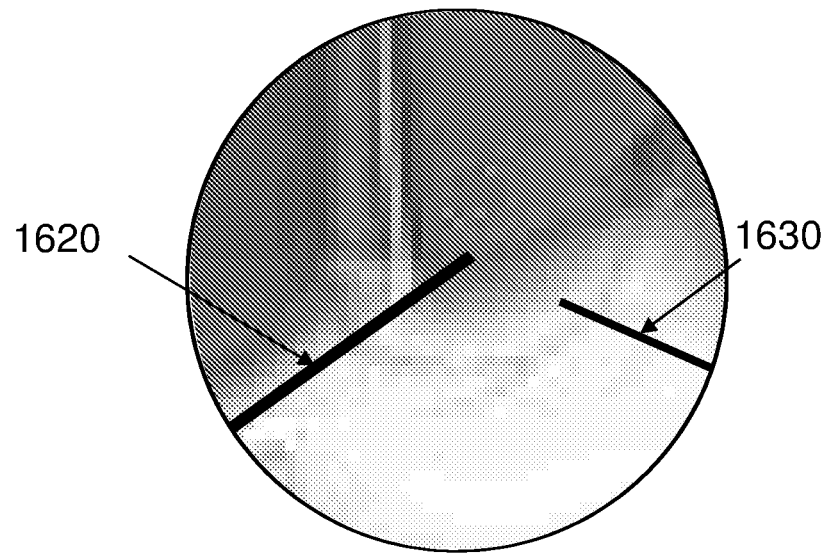

In reference to FIG. 20A-B, which shows, in a non-limiting manner, an embodiment of a zoom command.

In FIG. 20A, two tools (1620, 1630) are being used in an operation on the liver (1610). To command a zoom inward, the tip of a tool, in this case, the right tool (1630), is moved in a clockwise circle (1650, dotted line).

As shown in FIG. 20B, once the circle has been made, according to the output protocol, the field of view is zoomed inward, keeping the center of the field of view the same, so that the image is magnified by 50%.

In this embodiment, an input protocol of a counterclockwise circle (not shown) of either tool would result in an output protocol of a zoom outward, increasing the field of view and demagnifying the image by 50%.

The embodiments shown herein are merely exemplary—there are many input protocols and many output protocols which have not been shown.

It should be noted that the association of input and output protocols is arbitrary; any input protocol can be associated with any output protocol.

Example 22—Input Protocol, Movement of an Operator

Non-limiting examples of input protocols involving movement of a part of an operator, in this case the hand, and associated output protocols will be given. For simplicity, each input movement command comprises a single movement protocol, a predetermined gesture. It is clear that a movement command can comprise any number of movement protocols, as well as positions, repositions and actions.

In reference to FIG. 21A-C, which shows, in a non-limiting manner, an embodiment of an input protocol comprising pointing a finger.

In FIG. 21A, a system comprising three tools (1520, 1530, 1540) is illustrated; the system is tracking (dashed line) the upper right tool (1530). As shown in FIG. 21B, in order to change tracking to the leftmost tool (1520), the operator points to the left (1750), in this case with the right hand.

As shown in FIG. 21C, according to the output protocol, once an operator has pointed, the system tracks (dashed line) the leftmost tool (1520).

In this example, for clarity, a single tool is tracked. It is clear that a plurality of tools can be simultaneously tracked.

Figure 22A:
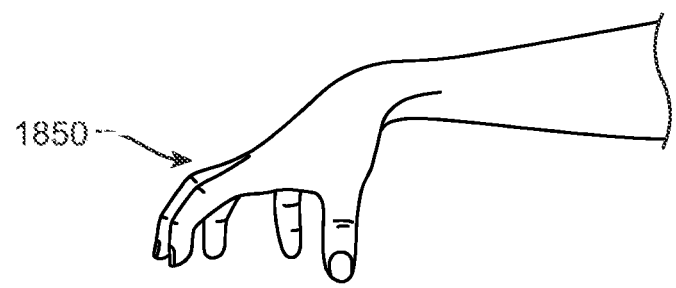
Figure 22B:
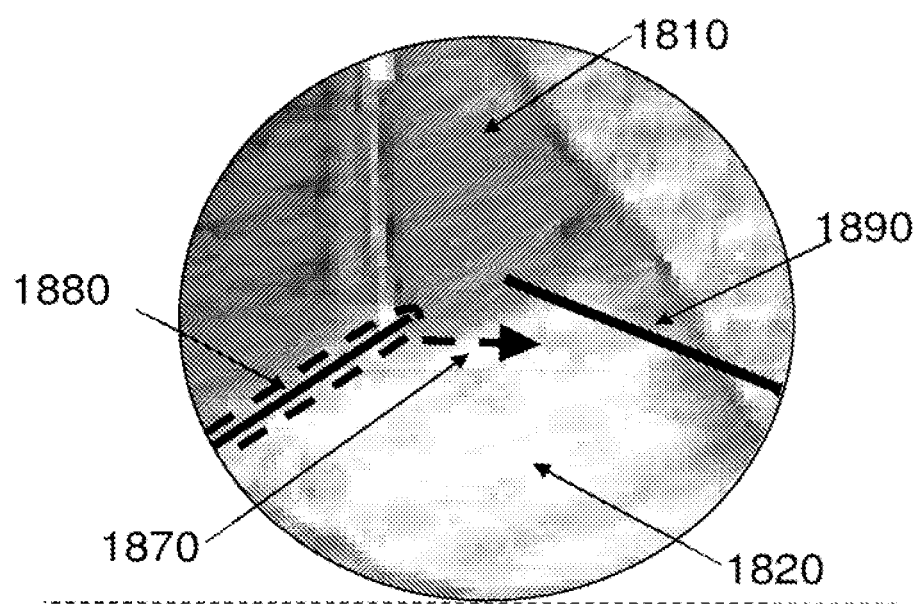
Figure 22C:
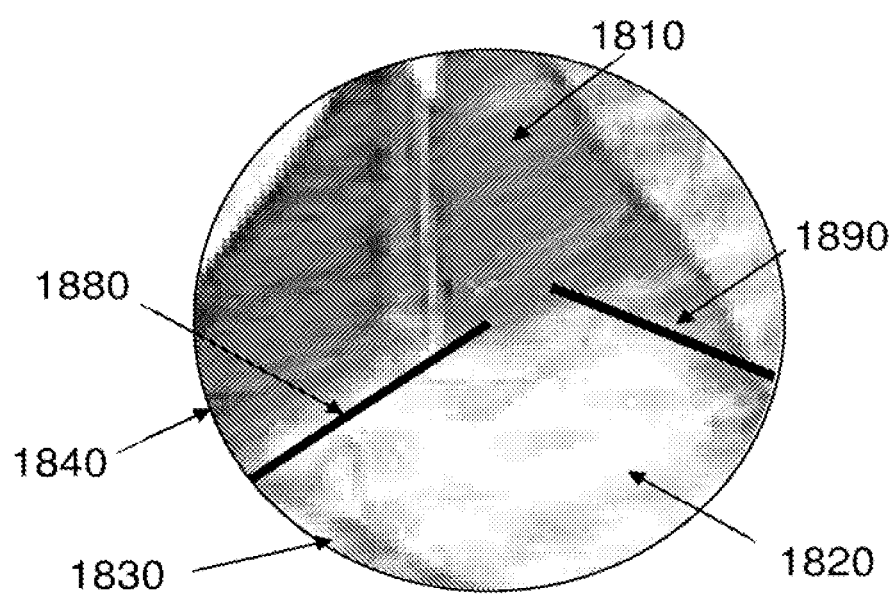

In reference to FIG. 22A-C, which shows, in a non-limiting manner, an embodiment of an input protocol for centering a field of view.

In this embodiment, the input protocol to place the center of the field of view at the tip of the tracked tool is holding the hand open downward with the finger spread as though picking up a bowl (FIG. 22A, 1850).

As shown in FIG. 22B, the tip of the tracked tool (1880, dashed line) is to the left of the center of the field of view, which shows two tools (1880, 1890), the liver (1810) and the stomach (1820).

The gesture (FIG. 22A, 1850) commands the output protocol, that the center of the field of view be moved to the right (dashed arrow, 1870). After the output protocol has been completed, the tip of the tracked, left, tool (1880, dashed line) is at the center of the field of view, which shows the two tools (1880, 1890), liver (1810), the stomach (1820), the intestines (1830) and gall bladder (1840).

In this example, for clarity, the center of the field of view follows a single tool. It is clear that the center of the field of view can depend on the locations of a plurality of tools.

Figure 23A:
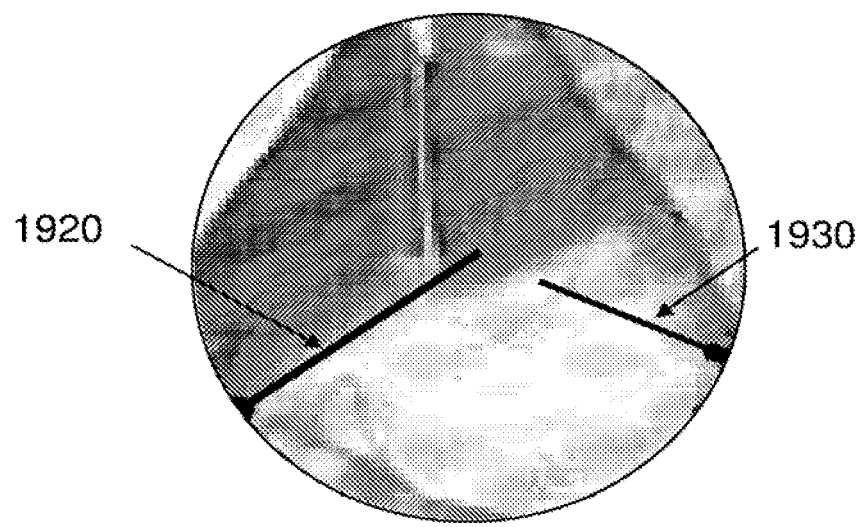
Figure 23B:
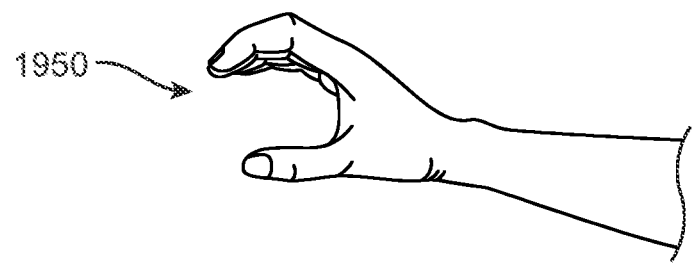
Figure 23C:
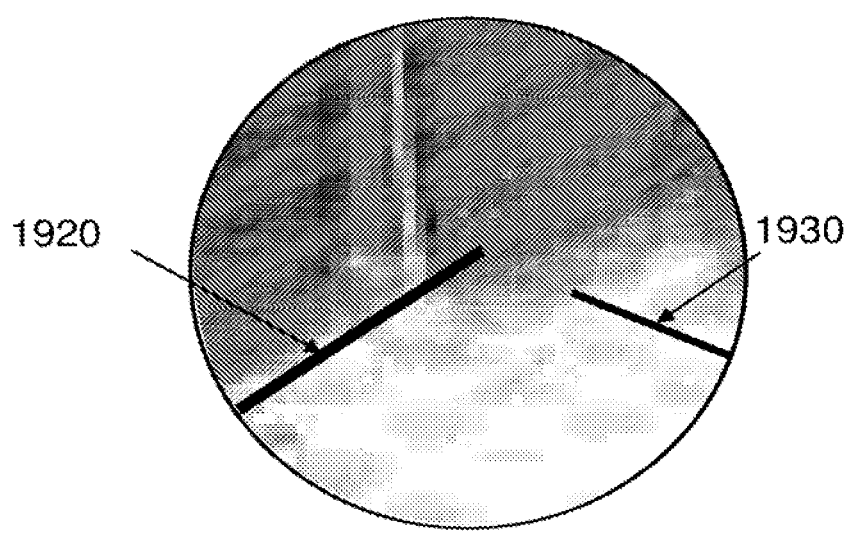

In reference to FIG. 23A-C, which shows, in a non-limiting manner, an embodiment of an input protocol to zoom an endoscope.

In this embodiment, the input protocol to zoom the endoscope inward is holding an open hand sideways with the fingers together, although picking up a book (FIG. 23A, 1950).

In FIG. 23B, two tools (1920, 1930) are being used in an operation on the liver (1910).

As shown in FIG. 23C, once the input protocol (holding the hand as though picking up a book) is made, according to the output protocol, the field of view is zoomed inward, keeping the center of the field of view the same, so that the image is magnified by 50%.

In this embodiment, an input protocol of a book-holding gesture pointing toward the right would result in an output protocol of a zoom outward, increasing the field of view and demagnifying the image by 50%.

The embodiments shown herein are merely exemplary—there are many input protocols and many output protocols which have not been shown.

It should be noted that the association of input and output protocols is arbitrary; any input protocol can be associated with any output protocol.

Example 23—Input Protocol, Movement of an Operator

A non-limiting example of an input protocol comprising movement of a part of an operator, in this case the eye, and an associated output protocol will be given. For simplicity, the input protocol comprises a single fixed predetermined gesture. It is clear that a movement command can comprise any number of movement protocols, as well as positions, repositions and actions.

Figure 24A:
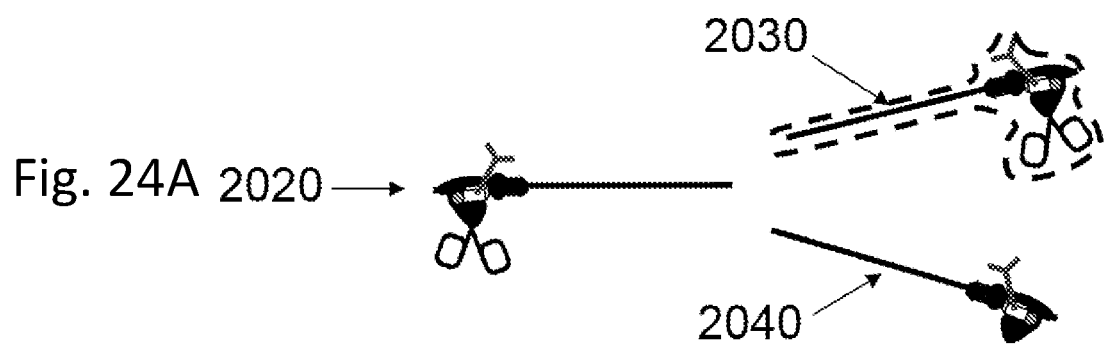
Figure 24B:
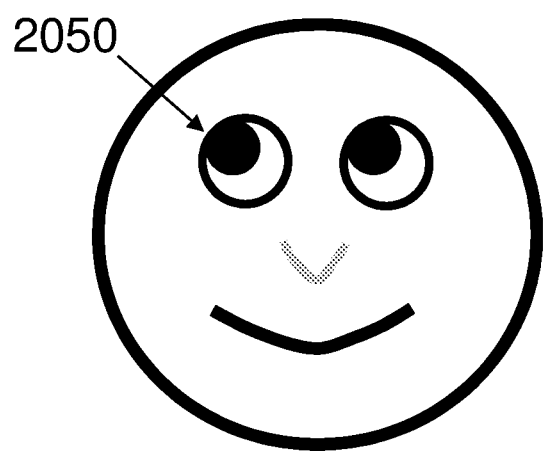
Figure 24C:
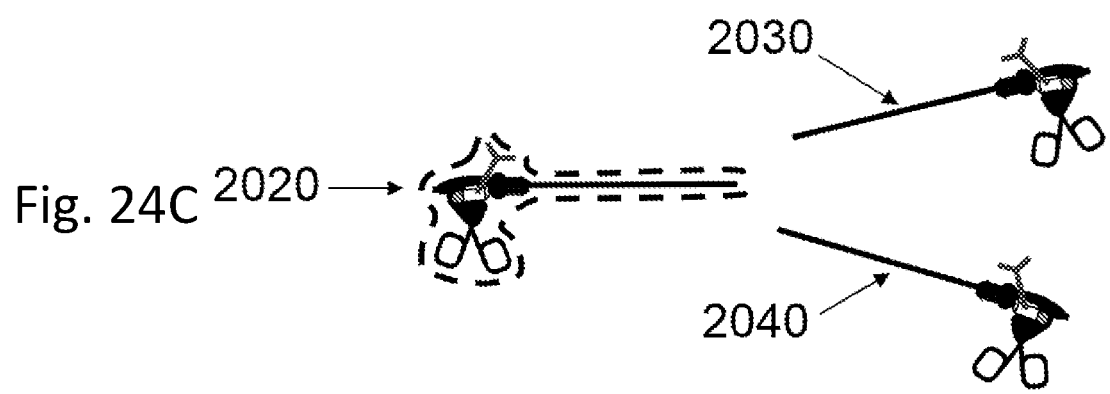

In reference to FIG. 24A-C, which shows, in a non-limiting manner, an embodiment of an input protocol comprising moving at least one eye.

In FIG. 24A, a system comprising three tools (2020, 2030, 2040) is illustrated; the system is tracking (dashed line) the upper right tool (2030). In order to change tracking to the leftmost tool (2020), at least one eye is moved to look upward to the left, preferably so that the operator is no longer looking at the display screen, as shown in FIG. 24B (2030). In preferred embodiments, the eye gesture need only be a quick glance, a momentary removal of the eyes from the display.

As shown in FIG. 24C, once the eye gesture (2060) is complete, according to the output protocol, the system tracks (dashed line) the leftmost tool (2020).

Figure 25A:
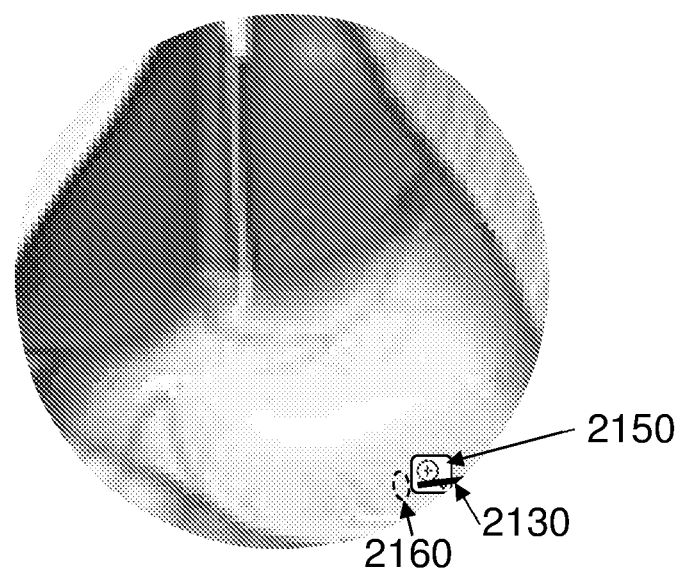
FIGS. 25A-B schematically illustrate an embodiment of a tracking system with an input protocol in which a tool is positioned.
Figure 25B:
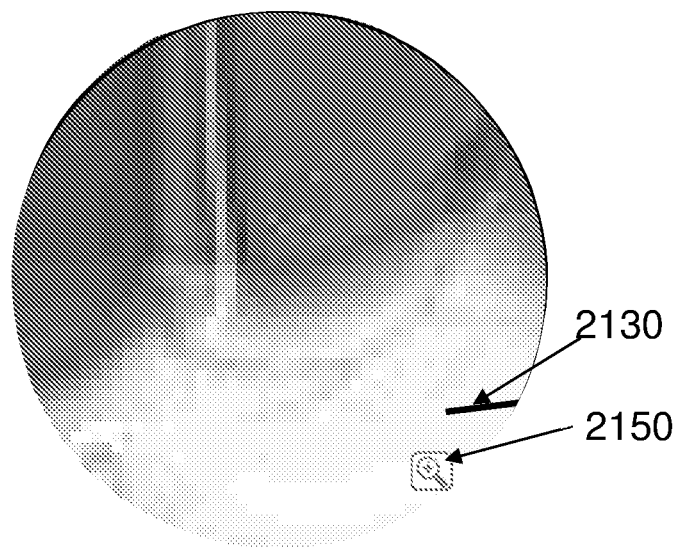

In this example, for clarity, a single tool is tracked. It is clear that a plurality of tools can be simultaneously tracked Example 24—Input Protocol, Position of a Tool A non-limiting example of an input movement command comprising a position of a tool is shown in FIG. 25A-B. The input movement command comprises an input position. In other embodiments, the input movement command can comprise a plurality of positions, repositions, actions and movement protocols.

In FIG. 25A, an embodiment of a display image is shown. The display comprises at least one icon (2150), with each icon being associated with an output command. In this embodiment, icons are invisible until a tool "enters" an icon, in other words, until the image of the tool is in the region of the display which can show the icon. In other embodiments, at least some icons are visible at all times.

In this embodiment, once a tool (2130) has entered an icon (2150), the output command is activated by moving the tool in a gesture which encircles the icon (2160, dotted arrow). In other embodiments, entering the icon region activates the output protocol; in yet other embodiments, other gestures are used.

In this exemplary embodiment, the icon (2150) shows a zoom-inward (+) symbol. After the circling motion (2160, dotted arrow) is completed, the system zooms the endoscope inward until the tool is removed from the icon, whereupon zooming stops and a magnified image is shown (FIG. 21B). The location of the icon is shown greyed-out in FIG. 21B for illustrative purposes. In preferred variants of this embodiment, an icon would only be showed greyed-out if the function with which it is associated is unavailable. In preferred variants, icons are preferably outside the image of the field of view or invisible when not in use, in order to ensure that the image of the field of view is as visible as possible.

In this example, for clarity, a single tool is shown. It is clear that any of a plurality of tools can be positioned over the icon.

Example 25—Input Protocol, Tagging of an Object

Figure 26A:
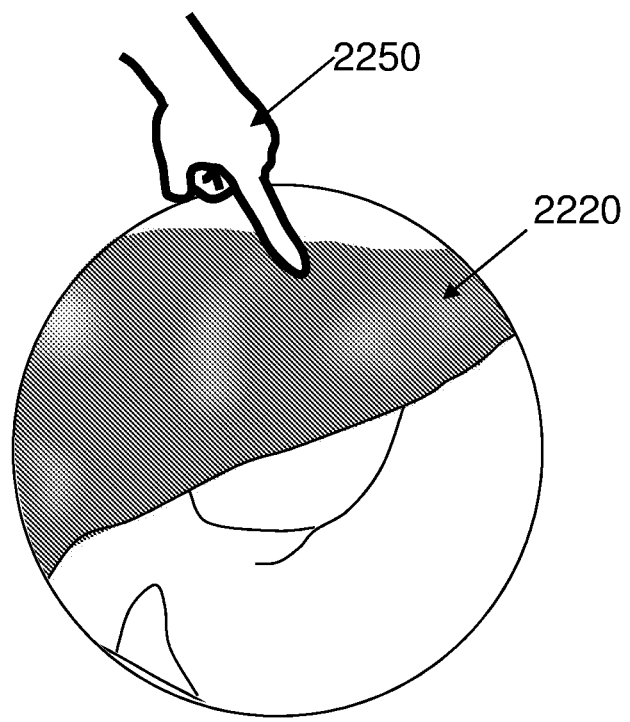
FIGS. 26A-B schematically illustrate an embodiment of a tracking system with an input protocol in which an object is tagged.
Figure 26B:
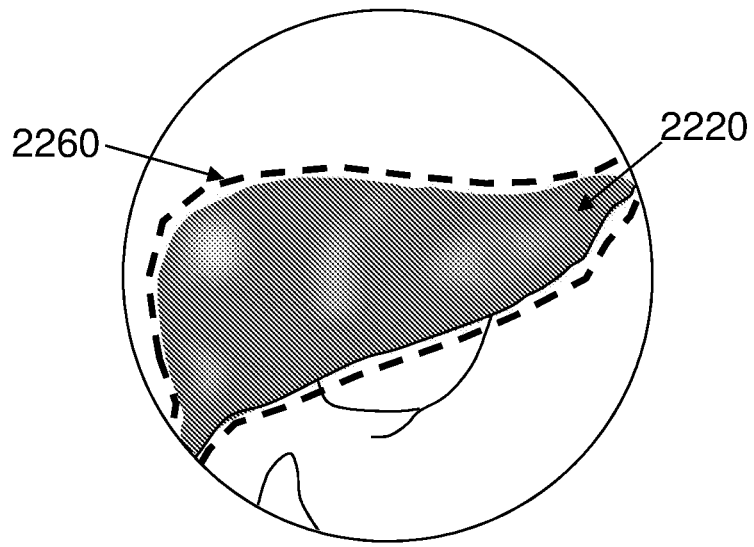

A non-limiting example of an input command comprising an action by a moving element is shown in FIG. 26A-B. For simplicity, the input command comprises a single action. In other embodiments, the input command can comprise a plurality of positions, repositions, actions and movement protocols.

In this embodiment, as shown in FIG. 26A, the command is pointing by a finger of an operator (2250) at the object (2260) to be tagged.

As shown in FIG. 26B, the output protocol tags (2260, dashed line) the object, centers it in the field of view, and zooms the object until it is entirely within the field of view and fills the field of view in at least one direction.

In this example, for clarity, a single tagged object is used. It is clear that any of a plurality of tagged objects can be kept within the field of view.

Example 26—Input Protocol, Activation of a Tool

Figure 27A:
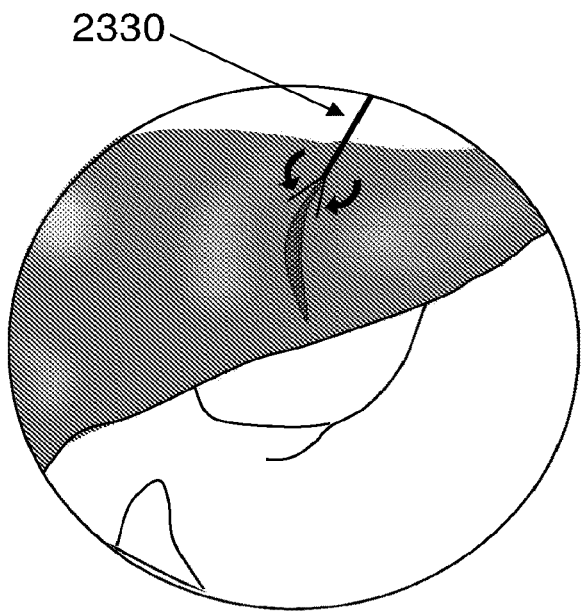
FIGS. 27A-B schematically illustrate an embodiment of a tracking system with an input protocol in which a tool is activated.
Figure 27B:
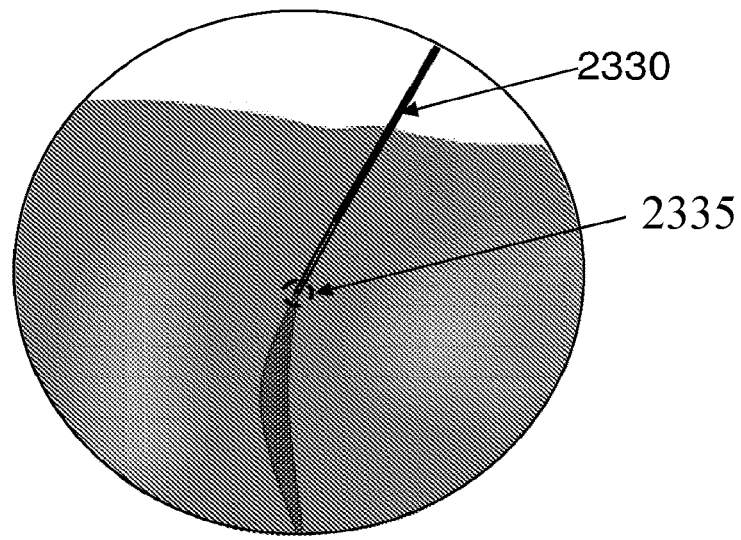

A non-limiting example of an input command comprising an action of activating a tool is shown in FIG. 27A-B. For simplicity, the input command comprises a single action; in other embodiments, the input command can comprise a plurality of positions, repositions, actions and movement protocols.

In this embodiment, as shown in FIG. 27A, the tool (2330) is a grasper and activation comprises closing the grasper (2350, curved arrows).

Closing (2350, curved arrows) of the grasper (2330) results in an output protocol in which (FIG. 23B) the tip (2335, dashed circle) of the grasper (2330) is placed in the center of the field of view and the view zoomed to give a good view of the tip of the grasper.

In this example, for clarity, a single tool is activated. It is clear that any of a plurality of tools can be activated, and that the activated tools need not be of the same type (e.g., a cautery and a graspers).

Example 27—Input Protocol, Tool Reaches Edge of Field of View

Figure 28A:
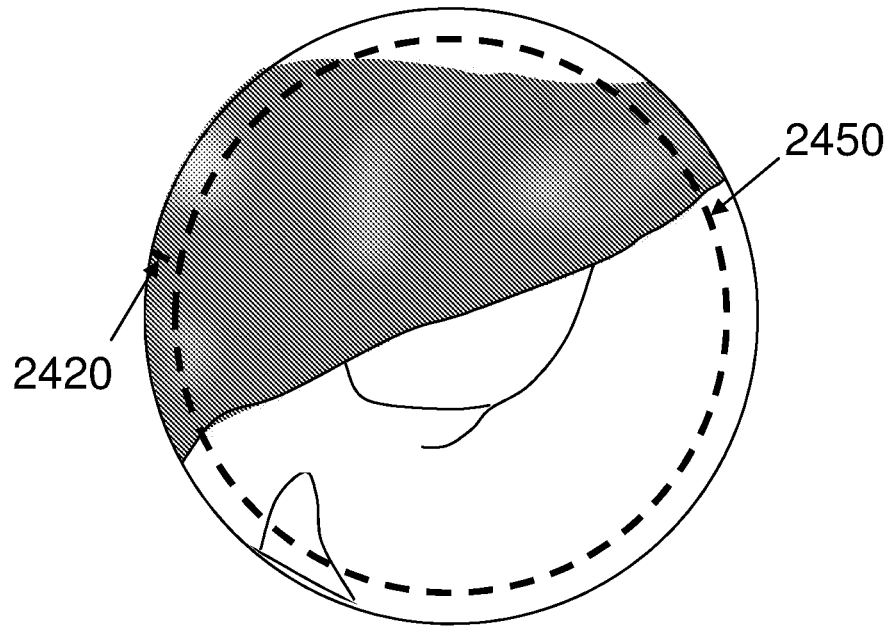
FIGS. 28A-B schematically illustrate an embodiment of a tracking system with an input protocol in which a tool is tracked if the tool reaches an edge of a field of view.
Figure 28B:
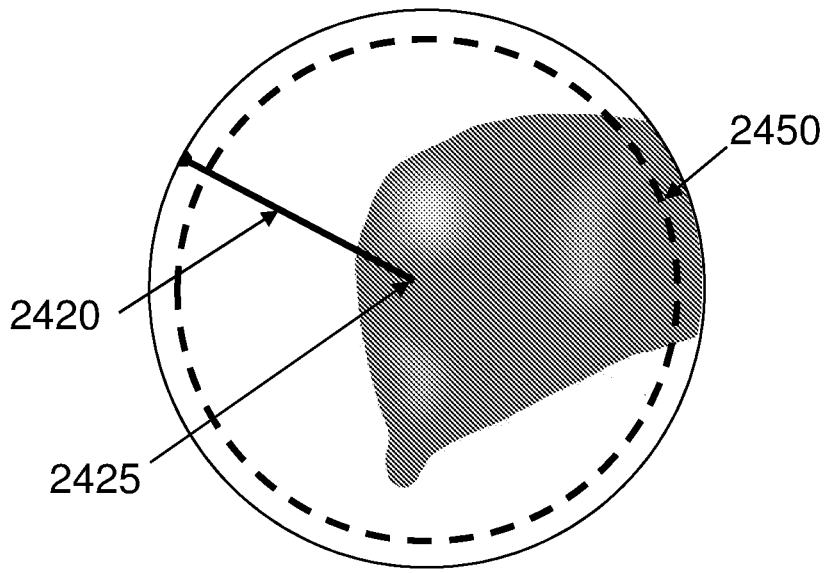

A non-limiting example of an input command to keep a tagged object from reaching an edge of the field of view is shown in FIG. 28A-B.

In this embodiment, as shown in FIG. 28A, the tagged object is a tool (2420). Location of the tip of the tool anywhere in the area between a predetermined distance (2450, dotted line) and the edge of the field of view determines activation of the input command that the tool tip is to be kept within the field of view. This, in turn, activates an output command to maneuver the endoscope so as to place the tip (2425) of the tool (2420) in the center of the field of view, as is shown in FIG. 28B.

In other embodiments, more than one article can be kept from the edge of the field of view. In such embodiments, a plurality of articles can be tagged. If a tagged article reaches an edge of the field of view, the endoscope will maneuver to move the article away from the edge. In some variants of these embodiments, in addition to, or in place of, maneuvering the endoscope, the endoscope's zoom will be altered until all the tagged articles are more than the predetermined distance from the edge.

Example 28—Relationship Between Articles

Figure 29:
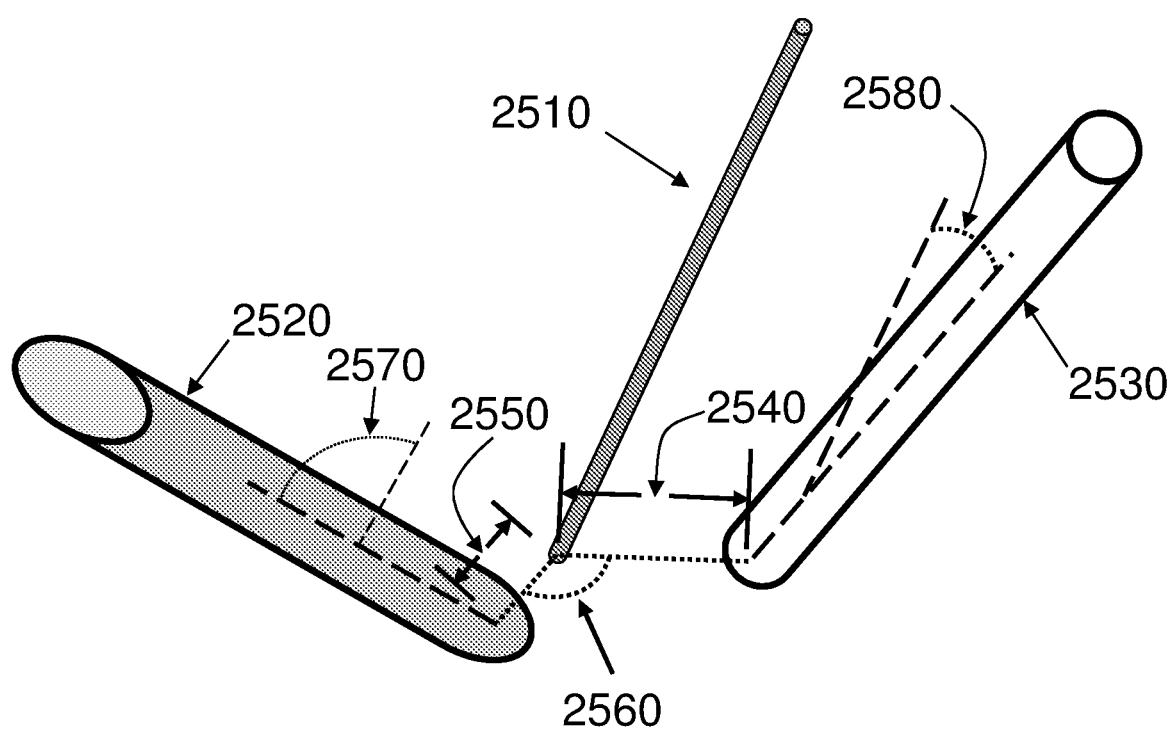
FIG. 29 schematically illustrates an embodiment of a tracking system with an input protocol in which a predetermined relationship is maintained between objects in a field of view.

A non-limiting example of a relationship between articles is shown in FIG. 29.

In this example, a fluid delivery tube (2520) and a suction tube (2530) are kept at fixed distances (2540, 2550), which are not the same, from a cautery (2510). A predetermined angle (2560) is maintained between the tip of the fluid delivery tube (2520), the tip of the cautery (2510) and the tip of the suction tube (2530). In addition, the longitudinal axes of the tubes are at fixed angles (2570, 2580), not the same, relative to the longitudinal axis of the cautery.

Example 29—Virtual Maneuvering

Figure 30A:
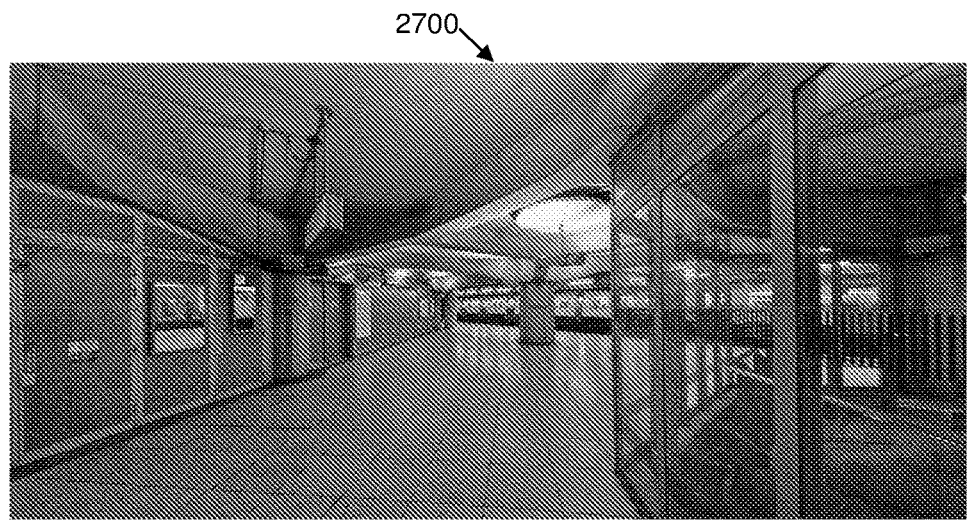
FIG. 30A-B, FIG. 31A-B and FIG. 32A-D illustrate an embodiment of virtual maneuvering.
Figure 30B:

In some embodiments of the system, the region viewed by the lens is significantly larger than the region displayed. FIG. 30A shows a non-limiting example of a region (2700) viewable by a fisheye lens, in this case a railway station, while FIG. 30B shows the whole of the image as captured by a camera using the fisheye lens (2710).

Figure 31A:
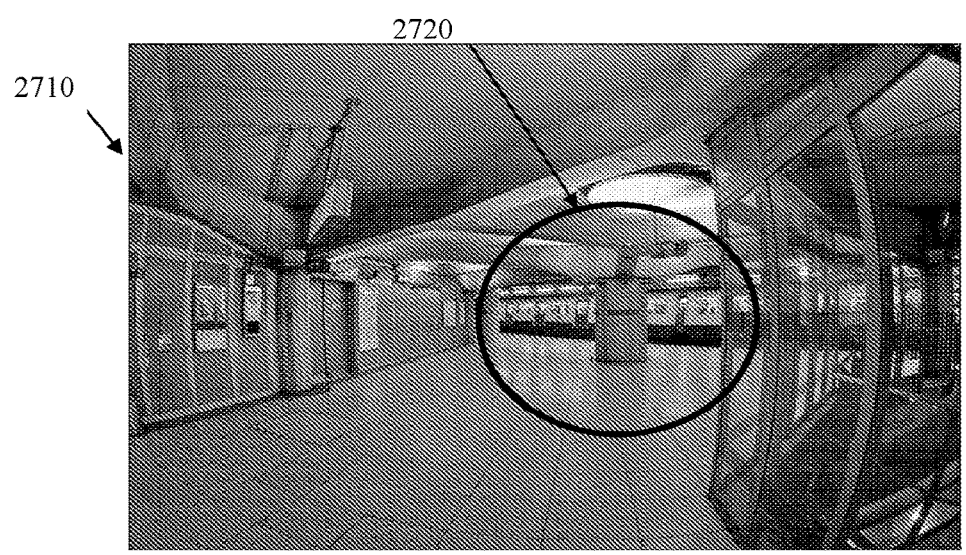
Figure 31B:
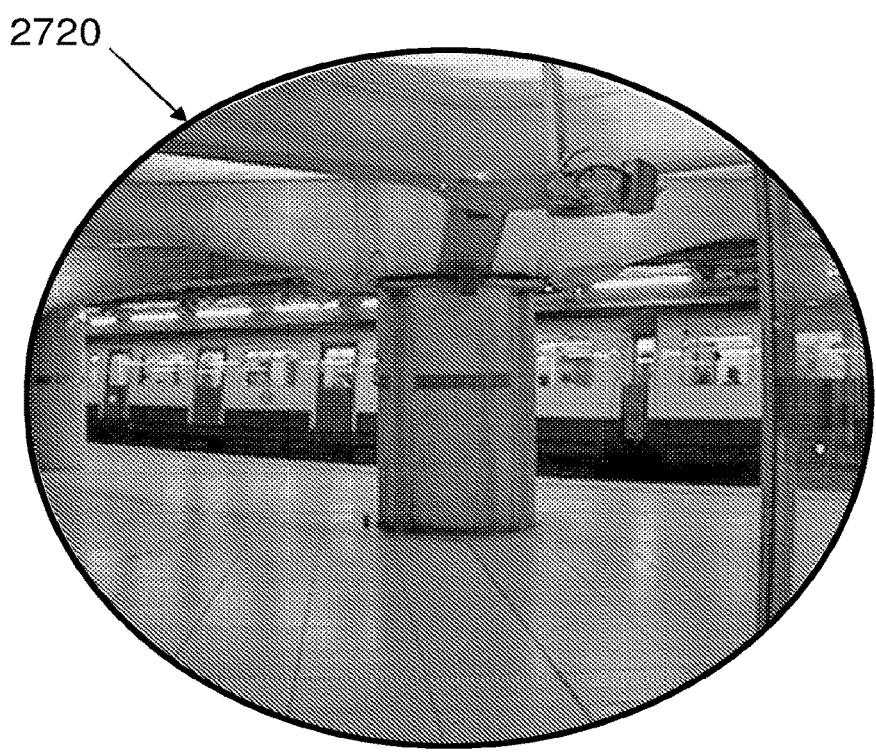

FIG. 31A shows, on the fisheye lens image (2710) the limits of the field of view of a display (2720), while FIG. 31B shows the image as seen in the display (2720), with the distortions of the fisheye lens removed by software.

In some embodiments of the system, image analysis is done so that the system "knows" what is happening outside the displayed image, but within the field of view of the lens. In such embodiments, the operator can be provided with a warning if something of interest has occurred outside the field of view of the display, but within the field of view of the lens.

Items of interest can include, but are not limited to, an article entering the field of view of the lens, an article moving, a likely collision between two articles, the occurrence of bleeding, the edges of an incision moving, activation or deactivation of a tool, articulation of a tool, and any combination thereof.

Non-limiting examples of collisions between two articles are: a collision between two or more tools, and a collision between at least one tool and an organ.

The warning can be visual or aural, with an aural warning selected from a group consisting of a predetermined voice message or a predetermined sound. A visual warning can be selected from a group consisting of a light, either flashing or steady, or a region on the display changing in quality, where the change in quality can include, but is not limited to, changing color, changing brightness, a pop-up appearing, an icon or other symbol ungreying, and any combination thereof.

Figure 32A:
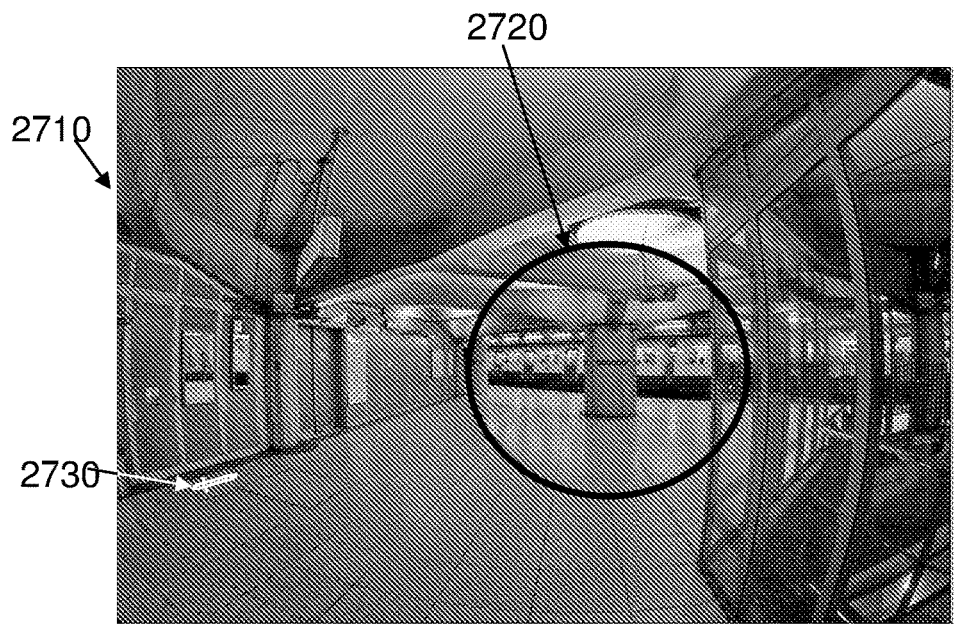

FIG. 32A shows the scene of FIG. 30A, with the addition of an exemplary item of interest (2730), a sword.

Figure 32B:
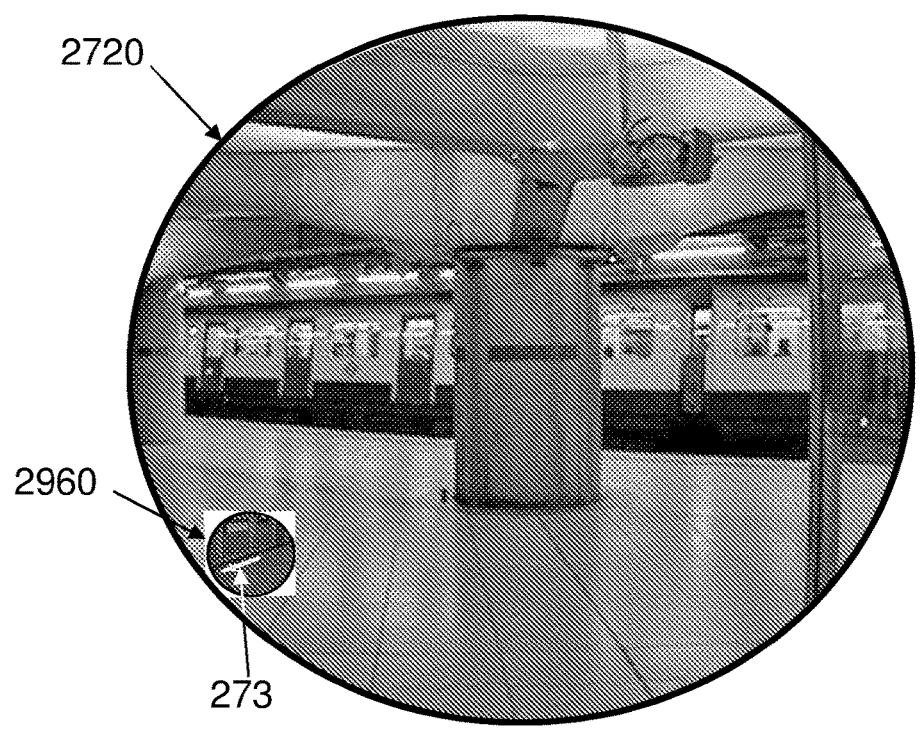

FIG. 32B shows a visual warning, a popup (2960), which shows the item of interest (2730).

Figure 32C:
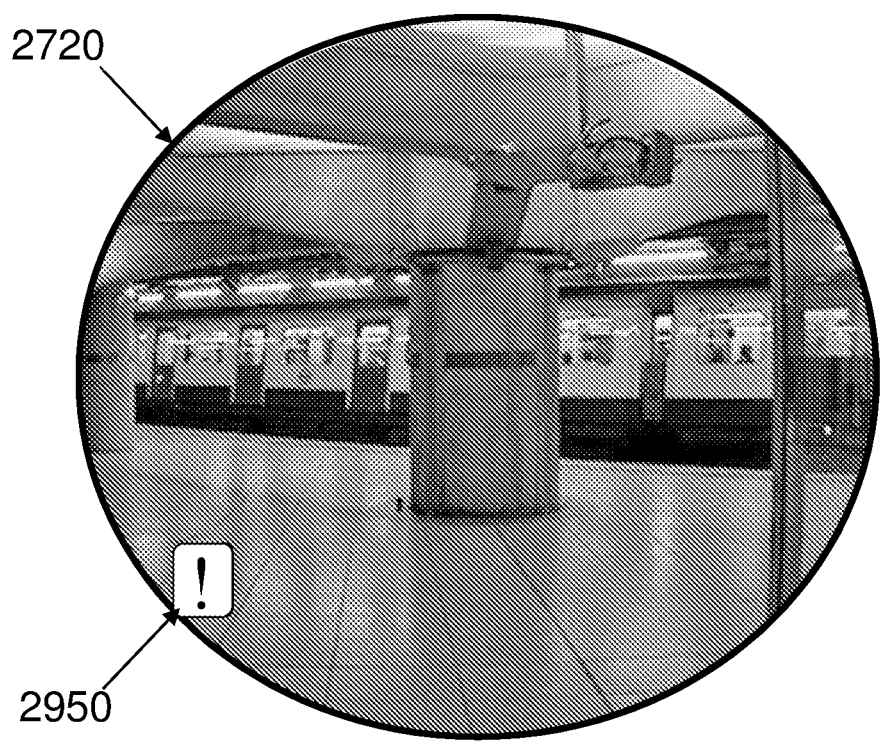

FIG. 32C shows another embodiment of a visual warning, a popup (2950) indicating the existence of an item of interest (2730, not shown) outside the field of view of the display (2720).

In some embodiments, the location of the popup indicates the location of the item of interest. In the embodiments shown, the location of the popup indicates that the item of interest is in the lower left quadrant of the field of view of the fisheye lens (2710).

A popup can be in a fixed position, it can use an arrow or other directional symbol to indicate the direction of the item of interest with respect to the icon or with respect to a fixed position (such as the center of the field of view), it can use different weight or different color symbols to indicate a distance to the item of interest, or a text message indicating direction, distance or both. The text message can be on the warning, or it can form part of a separate warning, which can be any type of visual or aural message as described hereinabove for a warning. Any combination of the above warnings and/or direction indicators and/or distance indicators can be used.

The system can provide preferred responses by means of which an operator can respond quickly to the warning. Such preferred responses can include, but are not limited to, moving the center of the field of view to the region where the item of interest is occurring, with or without zooming to improve the view of the region; zooming outward so that the field of view includes both the original field of view and the region where the item of interest is occurring, and any combination thereof.

A preferred response can be selected by positioning a movable article, preferably a tool, in a predetermined region of the display, such as on an icon or popup; by a predetermined movement of a movable article, preferably a tool; by touching a predetermined location on a screen, such as an icon or popup and any combination thereof.

Figure 32D:
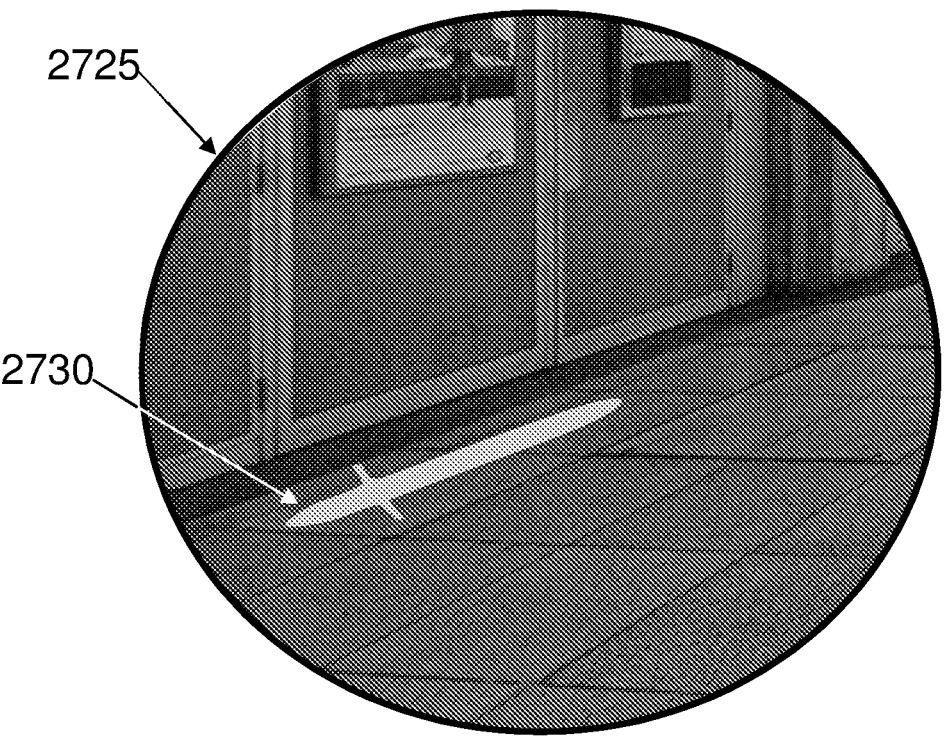

FIG. 32D shows a field of view of the display (2725) which includes the item of interest, as it would appear in some embodiments of the system. In this example, the magnification is the same for the original field of view and the field of view including the sword. In other embodiments, other magnifications can be used.

In the embodiment shown, the field of view of the display (2725) showing the item of interest entirely replaces the previous field of view of the display (2720). In other embodiments, a display field of view which includes the item of interest can appear as a popup or can replace only a portion of the earlier display field of view as in, for non-limiting example, a split screen.

It should also be noted how distorted the camera image is at the location of the item of interest, the sword, since the sword is near the edge of the field of view of the fisheye lens and of the camera.

The embodiments shown hereinabove are merely examples of fixed input protocols leading to fixed output protocols. There are many input protocols, many output protocols and many associations between input command and output command which are possible and have not been shown.

It should be noted that the associations of input and output commands shown above are arbitrary in that any of these input commands can be associated with any output command.

It should further be noted that these fixed input commands can comprise any of a tool movement, an operator movement and an operator brain signal, and that these can be combined in any way.

In some embodiments, the input commands will be chosen so as to make the system operate as intuitively as is practicable.

In preferred embodiments, the system is configured to analyze at least one of: one or more images as observed by an imaging device, the movements of the operator, sound signals, operator thoughts, contacts with a prepared surface and any combination thereof and to determine therefrom, without need for a predetermined fixed association, at least one output surgical procedure.

As discussed above, non-limiting examples of items to which the system can respond include the presence of smoke in the surgical environment, the presence of debris or particulates in the surgical environment, movements indicating surgical procedures such as suturing, blunt dissection, sharp dissection, placing or removal of a surgical tool, bleeding in the surgical environment, movement of tissue in the surgical environment, and any combination thereof.

Example 30—Suturing

Figure 33A:
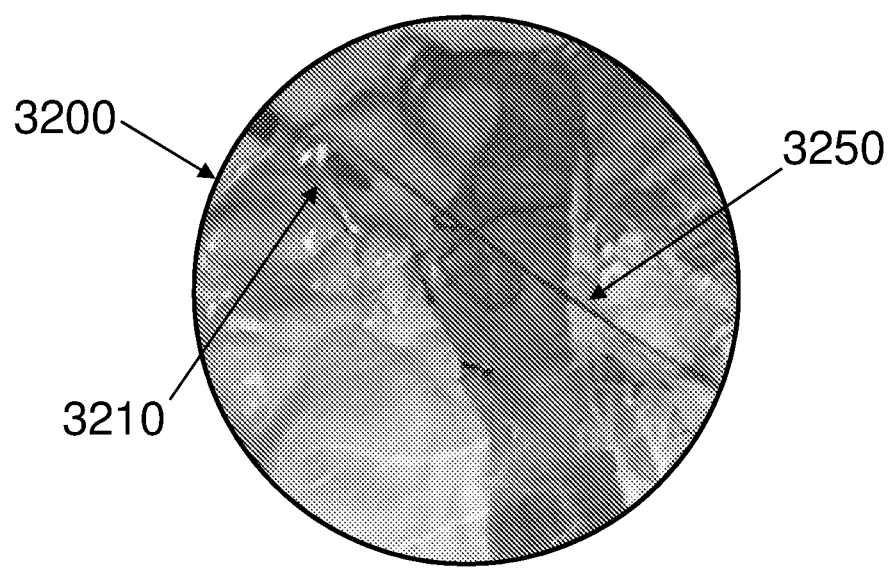
FIG. 33A-C schematically illustrates an interactive output surgical procedure.
Figure 33B:
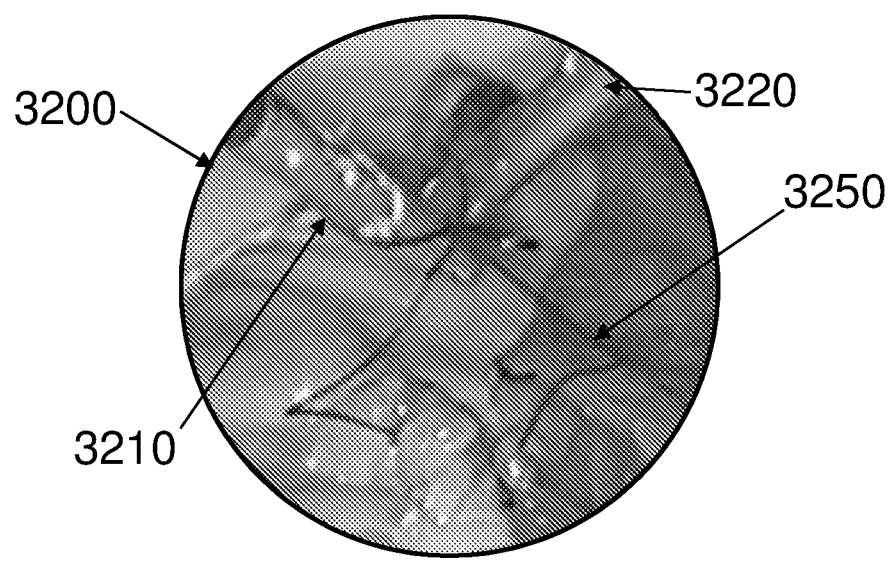
Figure 33C:
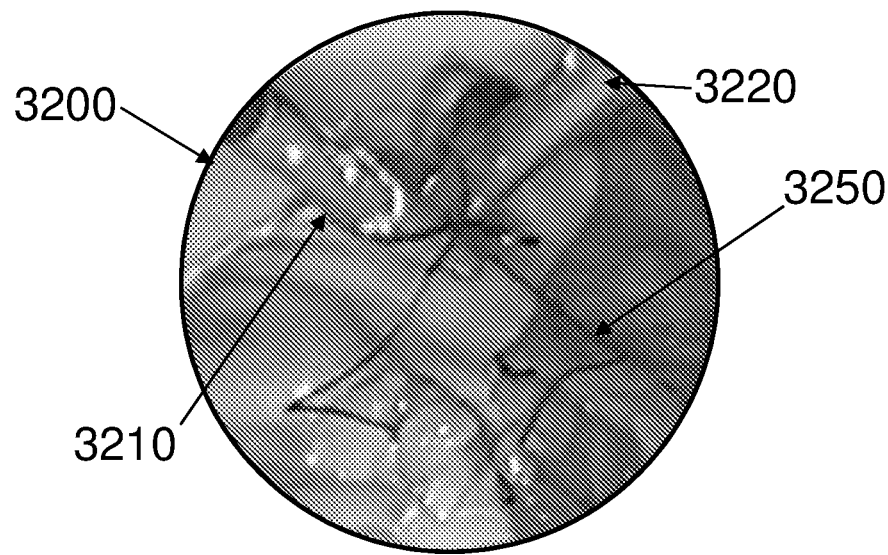

A non-limiting example of a responsive output surgical procedure is shown in FIG. 33A-C, which shows an illustrative field of view (3300) of a surgical field in which suturing is occurring. In FIG. 33A, a grasper (3310) is shown, holding suture thread (3250). The endoscope is zoomed out to give an overview of the start of a suture. FIG. 33B shows two graspers (3310, 3320) tying the suture thread (3250). It can be seen that the endoscope has zoomed in so that the field of view (3300) shows the tying process in close-up. FIG. 33C shows the field of view at the point where a tie in the suture thread is being pulled tight. The endoscope has been zoomed out so that both surgical tools (3310, 3320) remain in the field of view (3300); the entire portion of the surgical thread (3250) being worked on is visible.

Example 31—Recommendation

Figure 34:
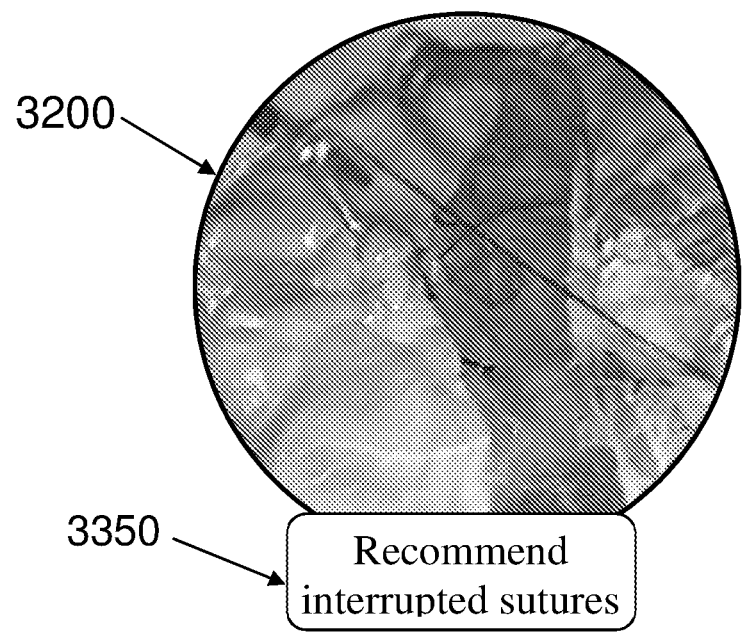
FIG. 34 illustrates an exemplary recommendation.

A non-limiting example of a recommendation is shown in FIG. 34. This non-limiting example is for a recommendation given at the start of a suturing procedure. In this non-limiting example, a popup (3350) is shown at the bottom of the field of view (3200), recommending a type of suture, in this case, an interrupted suture. Other non-limiting examples of recommendations for a suturing procedure can include, but are not limited to: another type of suture; a distance between sutures; or a reminder that, for toddlers, sutures need to be closer together than would be recommended for adults. Many more examples will be obvious to one skilled in the art, both for suturing procedures and for other types of procedures.

Example 32—Suggestion

Figure 35:
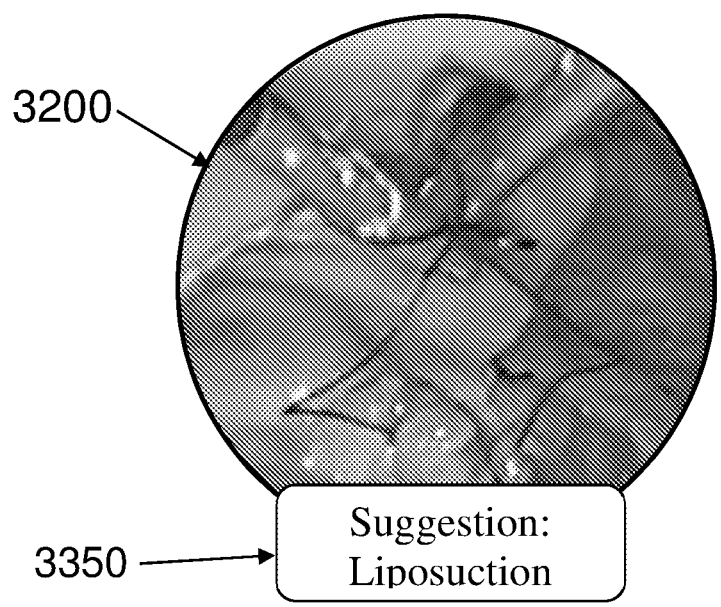
FIG. 35 illustrates an exemplary suggestion.

A non-limiting example of a suggestion is shown in FIG. 35. In this non-limiting example, the system has identified significant amounts of fat in the surgical field, an indication that a fat-removal procedure is likely to improve the out-come of the procedure. In this non-limiting example, a popup (3350) is shown at the bottom of the field of view (3200), suggesting that a fat removal procedure, in this case, liposuction, be carried out. Many more examples will be obvious to one skilled in the art In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An intelligent surgical tool control system, comprising:
    an endoscope;
    at least one tool management system comprising:
        at least one maneuvering mechanism configured to robotically maneuver said endoscope in at least two dimensions, the maneuvering mechanism operable in a physical inward zoom to maneuver the camera towards a region of interest to enlarge a view of the region of interest captured by the camera;
        at least one controller configured to control activation of a virtual zoom function of said endoscope;
    at least one indicating element configured to indicate at least one surgical event during operation of the maneuvering mechanism in physical inward zoom, said at least one surgical event is selected from a group consisting of: movement of the endoscope approaching travel limits of the maneuvering mechanism and movement of the endoscope into restricted space adjacent to an object; and
    at least one processor comprising a computer program in communication with said controller and said at least one tool management system;
    wherein said computer program, when executed, is configured to, in response to detection of said at least one surgical event by said sensor during robotic movement of the endoscope in physical inward zoom towards a region of interest, activate a virtual zoom function of said endoscope.

2. The intelligent system of claim 1, wherein said indicating element is a sensor.

3. The intelligent system of claim 1, wherein said sensor is a sensor of said at least one maneuvering mechanism.

4. The intelligent system of claim 1, wherein said indicating element comprises said at least one controller.

5. The intelligent system of claim 1, wherein said indicating element comprises an imager.

6. The intelligent system of claim 5, wherein said imager comprises an imaging system configured to real-time image said field of view; said computer program, when executed by a data processor, being configured to (i) real time image process said at least one image, and (ii) at least one of: detect said movement of said endoscope; and detect said object.

7. The intelligent system of claim 1, wherein said indicating element comprises an analyzing processor to analyze an image of a field of view.

8. The intelligent system of claim 1, wherein said indicating element comprises a position processor to calculate a 3D position of said endoscope.

9. The intelligent system of claim 1, wherein said computer program, when executed, is further configured to cause activation of the virtual zoom function of said endoscope.

10. A method for intelligent control of a surgical tool control system, comprising steps of:
    positioning a distal end of the endoscope in a body cavity;
    robotically advancing the distal end of the endoscope towards a region within the body cavity, while capturing images of the region using the endoscope and displaying captured images of the region in real time;
    performing a physical inward zoom to further advance the camera towards the region of interest to enlarge a view of the region of interest captured by the camera;
    during the physical inward zoom of the distal end of the endoscope towards the region, detecting at least one surgical event selected from a group consisting of: movement of the endoscope approaching travel limits of the maneuvering mechanism and movement of the endoscope into restricted space adjacent to an object; and
    in response to detection of said at least one surgical event during the physical inward zoom, activating a virtual zoom function of said endoscope.

11. The method of claim 10, wherein detecting said at least one surgical event includes detecting said at least one surgical event using a sensor.

12. The method of claim 11, additionally comprising indicating a current three dimensional position of said moving element, $3D_{current}$ by means of said sensor.

13. The method of claim 11, wherein said sensor is a sensor of said at least one maneuvering mechanism.

14. The method of claim 10, wherein said indicating element comprises said at least one controller.

15. The method of claim 10, wherein said indicating element comprises an imager.

16. The method of claim 15, further wherein said imager comprises an imager of the endoscope, and wherein the method further comprises:
    using the imager to real-time image said field of view; and
    executing said computer program to
        real time image process said at least one image, and detecting from said image at least one of (i) said movement of said endoscope, and (ii) at least one said object.

17. The method of claim 10, wherein said indicating element comprises an analyzing processor to analyze an image of a field of view.

18. The method of claim 10, wherein said indicating element comprises a position processor to calculate a 3D position of said endoscope.

19. The method of claim 10, further comprising, after detecting said at least one surgical event, causing activation of the virtual zoom function of said endoscope.

20. A method for intelligent control of a surgical tool control system, comprising steps of:
    positioning a distal end of the endoscope in a body cavity;
    robotically advancing the distal end of the endoscope towards a region within the body cavity, while capturing images of the region using the endoscope and displaying captured images of the region in real time;
    performing a physical inward zoom to further advance the distal end of the camera camera towards the region of interest to enlarge a view of the region of interest captured by the camera;

during the physical inward zoom, detecting that the endoscope has moved into restricted space adjacent to an object; and in response to detection that the endoscope has moved into restricted space adjacent to an object, activating a virtual zoom function of said endoscope.

* * * * *